US007563866B2

(12) United States Patent
Lamping et al.

(10) Patent No.: US 7,563,866 B2
(45) Date of Patent: Jul. 21, 2009

(54) MODULAR ANTIGEN TRANSPORTER MOLECULES (MAT MOLECULES) FOR MODULATING IMMUNE REACTIONS, ASSOCIATED CONSTRUCTS, METHODS AND USES

(75) Inventors: Norbert Lamping, Hannover (DE); Reto Crameri, Davos-Platz (CH); Sabine Fluckiger, Davos-Platz (CH); Isabelle Daigle, Davos-Platz (CH)

(73) Assignee: ImVisioN GmbH, Hannover (DE)

( * ) Notice: Subject to any disclaimer, the term of this patent is extended or adjusted under 35 U.S.C. 154(b) by 302 days.

(21) Appl. No.: 11/102,883

(22) Filed: Apr. 11, 2005

(65) Prior Publication Data

US 2005/0281816 A1 Dec. 22, 2005

Related U.S. Application Data

(63) Continuation-in-part of application No. PCT/EP03/11190, filed on Oct. 9, 2003.

(30) Foreign Application Priority Data

Oct. 11, 2002 (EP) .................................... 2022774

(51) Int. Cl.
*A61K 38/00* (2006.01)
*A61K 38/16* (2006.01)
*C08H 1/00* (2006.01)
*A61K 39/00* (2006.01)
*A61K 39/35* (2006.01)
*A61K 39/36* (2006.01)
*A61K 39/385* (2006.01)

(52) U.S. Cl. ....................... 530/345; 530/350; 530/379; 530/402; 530/403

(58) Field of Classification Search ....................... None
See application file for complete search history.

(56) References Cited

U.S. PATENT DOCUMENTS 5,804,604 A * 9/1998 Frankel et al. .............. 530/324

FOREIGN PATENT DOCUMENTS

WO WO 2004/094639 A2 * 11/2004

OTHER PUBLICATIONS

Platts-Mills et al (J. Allergy Clin. Immunol. 1998, 102: 335-343).*
Hoffmann-Sommergruber et al (J. Allergy Clin. Immunol. 1999, 104: 478-484).*
Corradin et al (Expert Opin. Biol. Ther. 2004, 4(10): 1629-1639).*
Merck Manual 16$^{th}$ Edition, Berkow, ed. 1992, Rahway, NJ, Merck & Co., Inc, pp. 20-21.*
Bodey et al (Anticancer Research 20: 2665-2676, 2000).*
Boon et al (Ann. Rev. Immunol. 2006, 24: 175-208).*
Fahey et al. Clin. Exp. Immunol. 1992, 88: 1-5.*
Letvin, Science, 1998, 280: 1875-1880.*
Machuca et al. Intervirology 1999, 42: 37-42.*
Tisch et al (PNAS 91: 437-438, 1994).*
Schwartz and Kipnis (The Neuroscientist, 8(5): 405-413, 2002).*
Fujii et al (Human Immunol. 1998, 59: 607-614).*
Encyclopedia Brittanica Online, Mar. 2004, www.search.eb.com/eb/print?eu=76559.*
Marchand et al (Exp. Opin. Biol. Ther. 1(3): 497-510, 2001).*
GenPept Accession No. AAH18726, Jul. 2006, 3 pages.*

* cited by examiner

*Primary Examiner*—G. R Ewoldt
*Assistant Examiner*—DiBrino Marianne
(74) *Attorney, Agent, or Firm*—Whitham, Curtis, Christofferson & Cook, P.C.

(57) ABSTRACT

Modular antigen transporter molecules (MAT molecules), which are used as vaccines and for the treatment of allergies, include three modules: a translocation module which brings about transport of the MAT molecule into the interior of the cell; a targeting module which directs the MAT molecule to intracellular organelles involved in antigen processing and loading; and an antigen module which contains an allergen.

6 Claims, 15 Drawing Sheets

Trans – AG – Target
Trans – Target – AG
AG – Trans – Target
AG – Traget – Trans
Target – Trans – AG
Target – AG – Trans
Tag – Trans – Target – AG
Tag1 – Tag2 – Trans – Target1 – Target2 – AG1 – AG2 – AG3
Trans – Tag1 – Target – Tag2 – AG
Trans – Target – AG1 – AG2
Trans – Target1 – Target2 – AG
Trans1 – Trans2 – Target – AG1 – AG2
Trans1 – Trans2 – Target1 – Target2 – AG1 – AG2
Trans1 – AG – Target1 – Trans2 – Target2 – AG2
Figure 1A
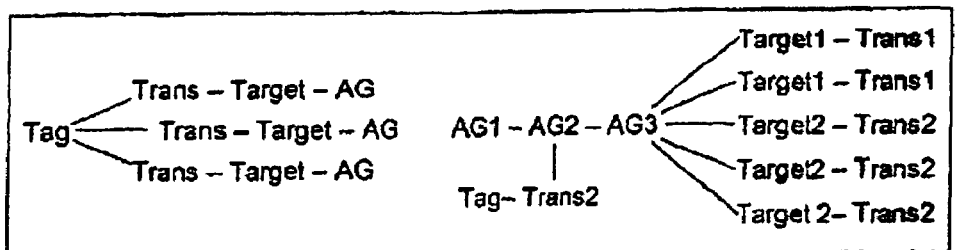
Figure 1B
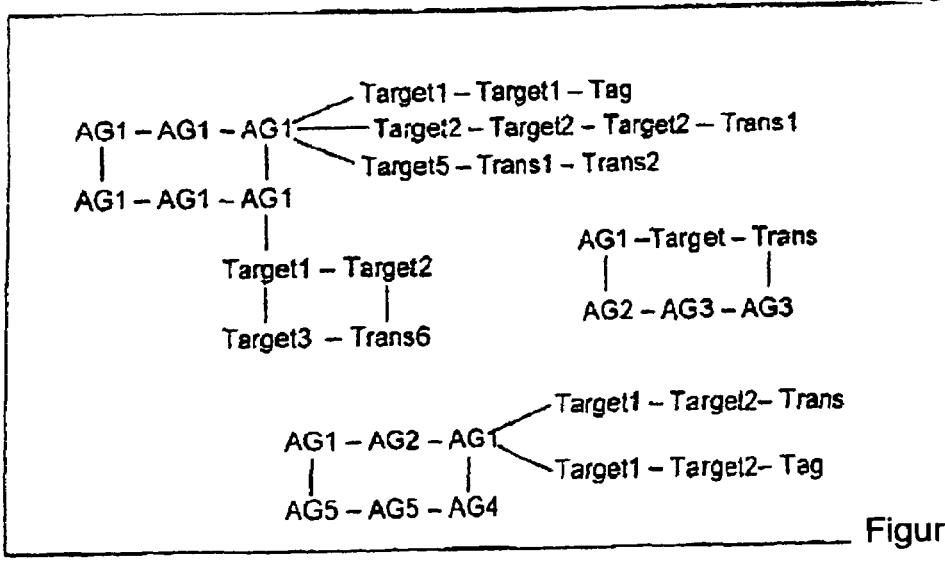
Figure 1C

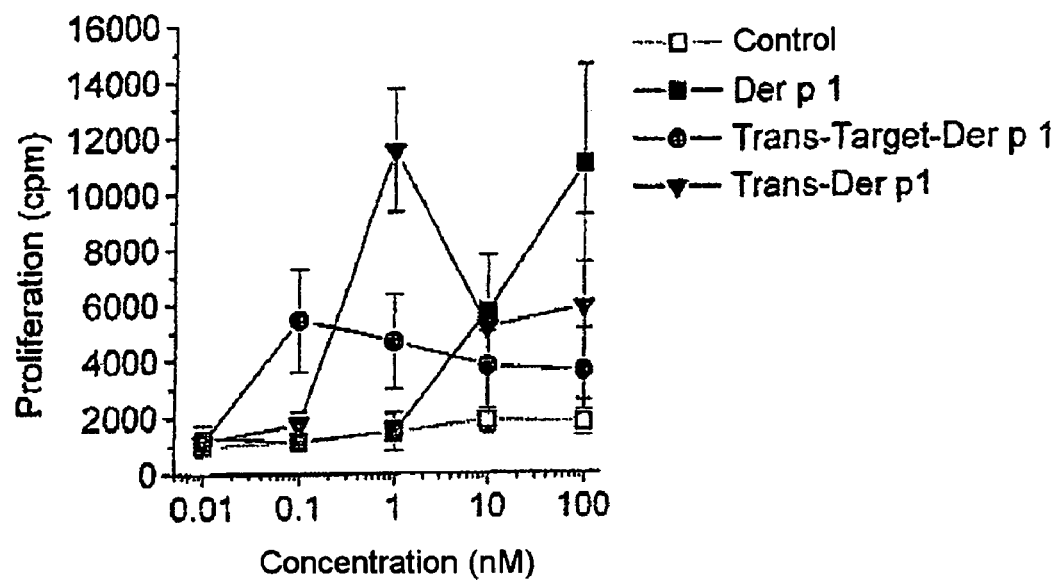
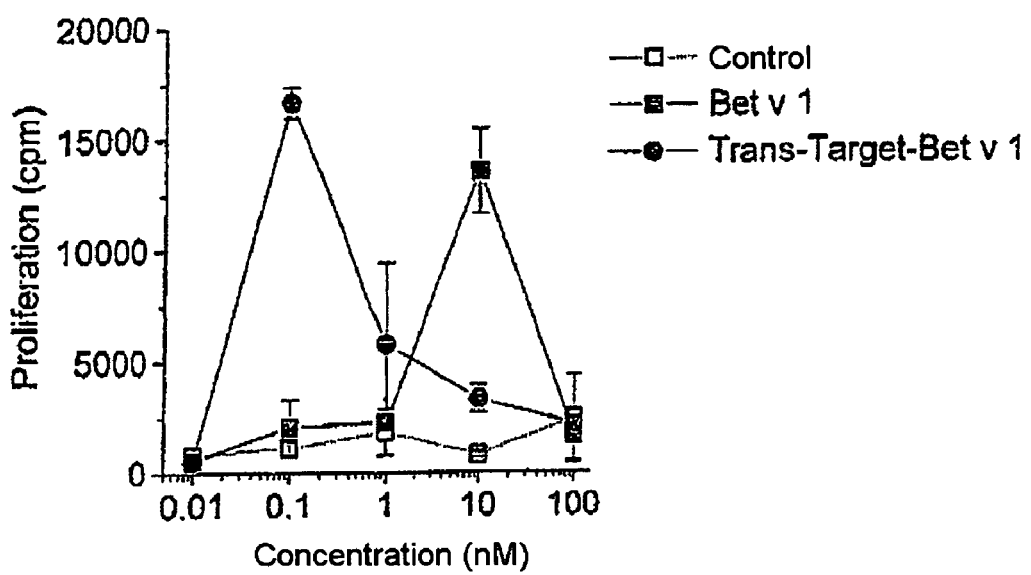
Figure 7A-B

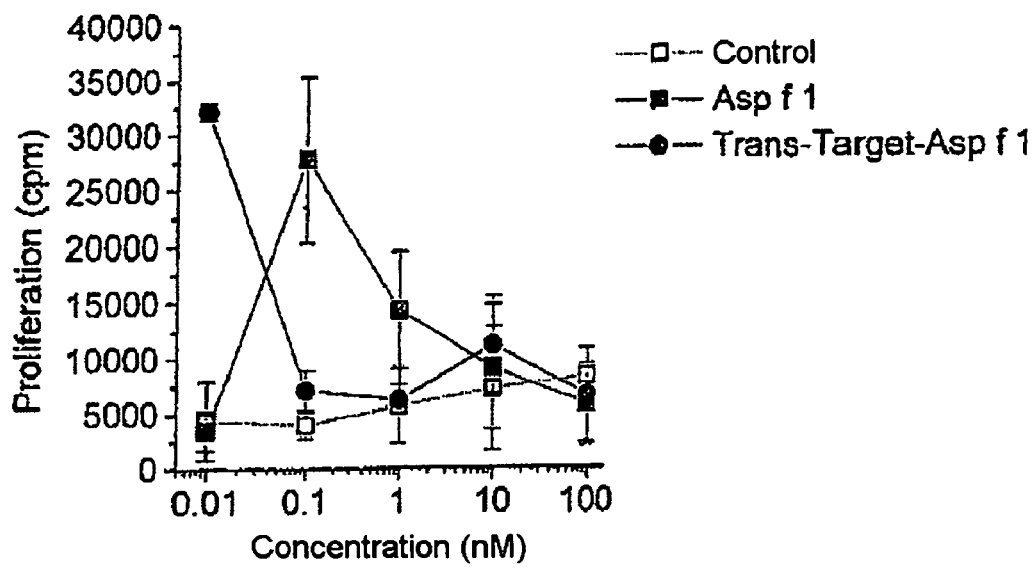
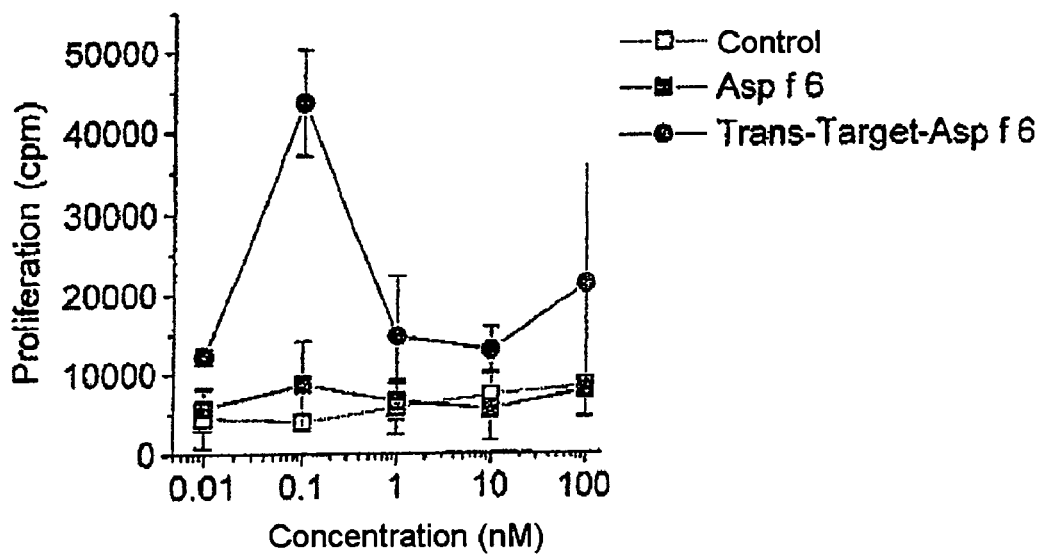
Figure 7C-D

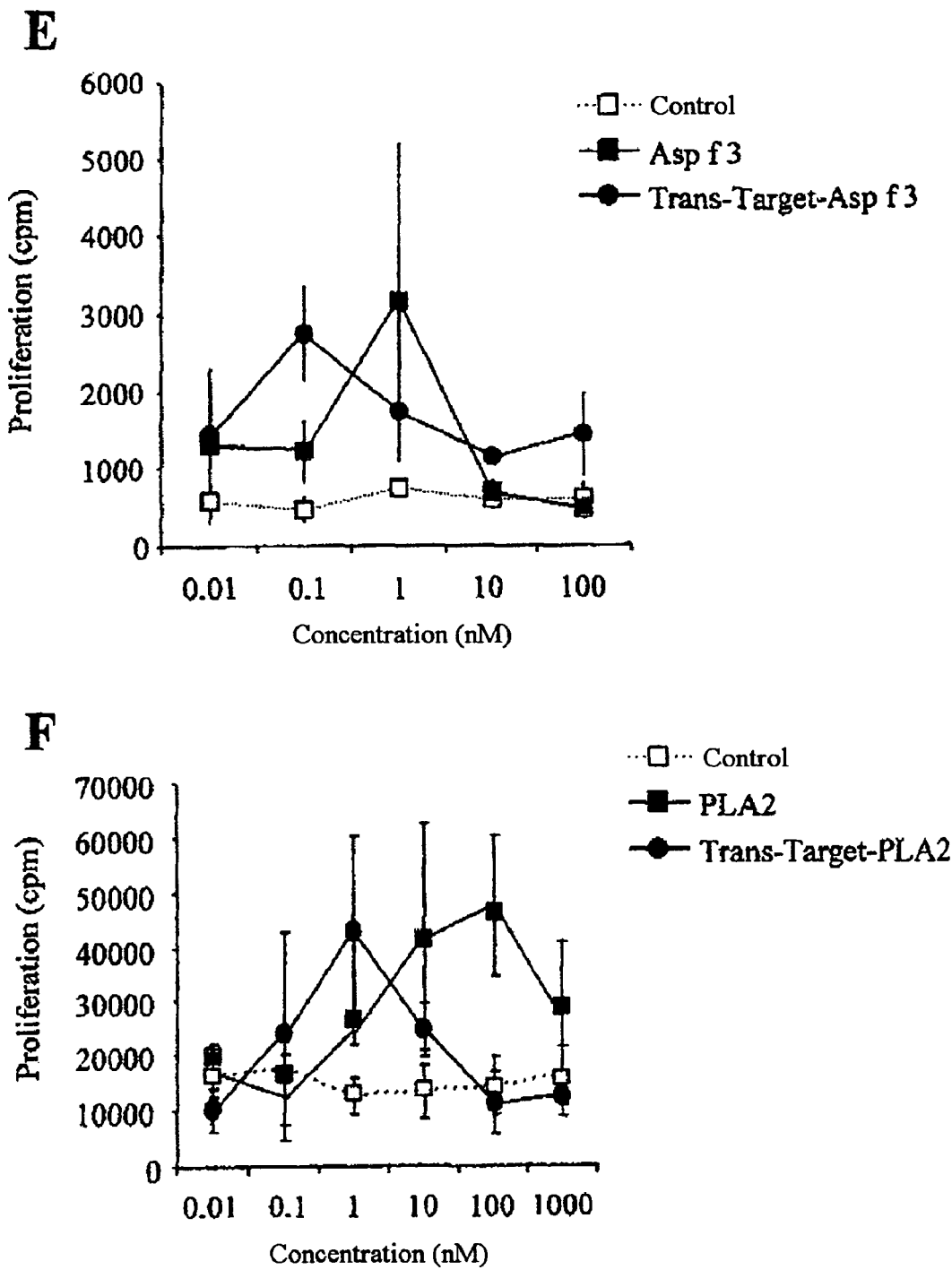
Figure 7E-F

| | | | | |
|---|---|---|---|---|
| MGYGRKKRRQ | RRRGSMDDQH | DLISNNEQLP | MLGRRPGAPE | SKCSRGALYT | 50
| GFSILVTLLL | AGQATTAYFL | YQQQGRLDKL | TVTSQNLQLE | NLRMKLPKPP | 100
| KPVSKMRMAT | PLLMQALPMG | ALPQGTSGSV | KMAETCPIFY | DVFFAVANGN | 150
| ELLLDLSLTK | VNATEPERTA | MKKIQDCYVE | NGLISRVLDG | LVMTTISSSK | 200
| DCMGEAVQNT | VEDLKLNTLG | REICPAVKRD | VDLFLTGTPD | EYVEQVAQYK | 250
| ALPVVLENAR | ILKNCVDAKM | TEEDKENALS | LLDKIYTSPL | C | 291

B

| | | | | |
|---|---|---|---|---|
| atgggttacg | gtcgtaaaaa | gcgtcgccag | cgtcgccgtg | gatctatgga | 50
| tgaccagcac | gaccttatct | ccaacaatga | gcaactgccc | atgctgggcc | 100
| ggcgccctgg | gccccggag | agcaagtgca | gccgcggagc | cctgtacaca | 150
| ggcttttcca | tcctggtgac | tctgctcctc | gctggccagg | ccaccaccgc | 200
| ctacttcctg | taccagcagc | agggccggct | ggacaaactg | acagtcacct | 250
| cccagaactt | gcagctggag | aacctgcgca | tgaaacttcc | caagcctccc | 300
| aagcctgtga | gcaagatgcg | catggccacc | ccgctgctga | tgcaggcgct | 350
| gcccatggga | gccctgcccc | aggggactag | tggatccgtt | aaaatggctg | 400
| aaacctgccc | gatcttctac | gacgtttct | tcgctgttgc | taacggtaac | 450
| gaactgctgc | tggacctgtc | cctgaccaaa | gttaacgcta | ccgaaccgga | 500
| acgtaccgct | atgaaaaaaa | tccaggactg | ctacgttgaa | aacggtctga | 550
| tctcccgtgt | tctggacggt | ctggttatga | ccaccatctc | ctcctccaaa | 600
| gactgcatgg | gtgaagctgt | tcagaacacc | gttgaagacc | tgaaactgaa | 650
| caccctgggt | cgtgaaatct | gcccggctgt | taaacgtgac | gttgacctgt | 700
| tcctgaccgg | taccccggac | gaatacgttg | aacaggttgc | tcagtacaaa | 750
| gctctgccgg | ttgttctgga | aaacgctcgt | atcctgaaaa | actgcgttga | 800
| cgctaaaatg | accgaagaag | acaaagaaaa | cgctctgtcc | ctgctggaca | 850
| aaatctacac | ctccccgctg | tgctaa | | | 876

Figure 10

MODULAR ANTIGEN TRANSPORTER MOLECULES (MAT MOLECULES) FOR MODULATING IMMUNE REACTIONS, ASSOCIATED CONSTRUCTS, METHODS AND USES

CROSS REFERENCE TO RELATED APPLICATIONS

This is a continuation-in-part (CIP) application of International Application PCT/EP2003/011190 with an international filing date of Oct. 9, 2003.

FIELD OF THE INVENTION

The invention is concerned with stimulation and inhibition of the immune system for prophylaxis, therapy or diagnosis of disorders associated with an immune system which is insufficiently stimulated or is excessively stimulated. These disorders include inter alia infectious diseases, neoplastic diseases, allergies, autoimmune diseases, transplant rejection reactions etc. The core of the invention is a novel method with which the immune system is influenced by giving a MAT molecule that consists at least of the three following constituents:
1. a translocation module which has the effect that the MAT molecule can penetrate into cells from the outside,
2. an intracellular targeting module which has the effect that the MAT molecule is processed within the cell in such a way that there is an altered immune response or an altered presentation of the antigen, and
3. an antigen module which determines the specificity of the modulated immune response.

Combination of these three elements to give a MAT molecule makes it possible for the immune system of the treated individual to be modulated in a targeted and specific manner, or makes it possible for the presentation of the antigen by the antigen-presenting cell to be altered.

BACKGROUND OF THE INVENTION

Processing of antigens by antigen-presenting cells The processing of antigens by antigen-presenting cells (APC) takes place by two different routes. Antigens occurring inside the cell are presented by MHC I (major histocompatibility complex class I, MHC class I) molecules on the cell surface, whereas extracellular antigens are presented by MHC II (major histocompatibility complex class II, MHC class II) molecules on the cell surface. Both mechanisms initiate an immune reaction by the host to the antigen. The route taken by the antigen from uptake into the cell until presentation on the cell surface in the form of an MHC II-antigen complex proceeds via various cell organelles, inter alia via the endoplasmic reticulum, the Golgi apparatus, the trans-Golgi network, lysosomes, endosomes and via MHC class II compartments (MIIC). The MIICs play an important part in the MHC II-mediated antigen presentation. In these organelles of the cell, the MHC II molecules are loaded with low molecular weight antigens or with proteolytic fragments of proteins. In this process, the invariant chain (also called MHC II gamma chain or Ii) which is initially bound to the MHC II molecule undergoes proteolytic degradation, and the antigen is bound to the MHC II molecule under the regulation of various proteins which bind directly or indirectly to MHC II [1]. These regulatory molecules include inter alia HLA-DM, HLA-DO, LAMP-1, LAMP-2, CD63, CD83, etc. The exact function of these proteins is in part unexplained as yet, but many of them have signal sequences which promote their transport to the lysosomes, to the endosomes, to the trans-Golgi network, to the MIICs etc. [2-4]. A number of proteases are involved in the proteolytic reactions necessary so that the antigen can be presented on MHC II molecules. The proteases present in MIICs include inter alia various members of the cathepsin family such as, for example, cathepsin S and cathepsin L [1].

SUMMARY OF THE INVENTION

Targeting and Targeting Sequences

Amino acid sequences which have the property of accumulating inside or outside a cell specifically at a particular site or in a particular cell organelle are frequently referred to as targeting sequences. It should be emphasized in this connection that various types of targeting can be distinguished. In particular there is a distinction between intracellular and extracellular targeting. For extracellular targeting, for example antibodies which bind from outside to directly accessible structures on the cell surface, e.g. to the extracellular portion of membrane proteins, are used. An antibody which binds a protein on the cell surface of tumor cells can be coupled for example to a cytotoxin. This antibody then brings about an extracellular targeting of the cytotoxin for the tumor cell, thus making targeted killing of the latter possible. This type of targeting is fundamentally different from intracellular targeting, in which it is often necessary to overcome intracellular membranes or in which the targeting sequence is bound by intracellular receptors and thus penetrates for example into particular cell organelles, or in which the targeting sequence can penetrate the specific channels, formed by specific proteins, into the cell organelle for which the targeting sequence is specific. If a targeting sequence or a targeting module is mentioned below in the present patent application, it is in principle always intracellular targeting and not extracellular targeting which is meant thereby. In addition, in the present patent application, targeting does not mean every type of intracellular targeting, but means only intracellular targeting which serves to transport molecules to organelles or intracellular regions involved in the processing, modification and/or binding of antigens to MHC molecules. Examples of such organelles or intracellular regions are the endoplasmic reticulum, the Golgi apparatus, the trans-Golgi network, endosomes, lysosomes and MIICs. Targeting sequences derived from various proteins are described in the literature [1-5].

Translocation and Translocation Sequences

In addition, numerous amino acid sequences, especially derived from viruses, e.g. HIV tat or the protein VP22 which is derived from herpes simplex virus, which promote the transport of proteins, peptides and other classes of substances, such as, for example, nucleic acids or pharmaceutically active substances, into the interior of cells are known from the literature. For this purpose, these so-called translocation sequences are linked to the molecules to be transported (also called cargo molecules) either via covalent or via non-covalent linkages. Extracellular addition of the resulting compounds of translocation sequence and cargo molecule to cells is then possible. The translocation sequence then brings about entry of the cargo molecule into the interior of the cell. This principle has likewise been described in numerous studies, especially for the HIV Tat sequence [6-8].

Although it was already possible and intended to use an antigen as cargo molecule, it has as yet not been possible with the aid of the known translocation means alone to generate an immune response in an individual in a sufficiently targeted and dosed manner as appears desirable for certain tasks—for example allergy desensitization. Hence there is a need for further methods for targeted immunomodulation.

DETAILED DESCRIPTION OF THE INVENTION

The invention provides a method which makes it possible for antigens to be supplied in a very targeted manner to cells in order to achieve an efficient, specific immune reaction. The method makes it possible firstly to convey antigens efficiently from the extracellular space to the intracellular space of the cell, and makes it possible secondly for the antigens, when they have arrived in the interior of the cell, to reach efficiently the cell organelles in which they are further processed for antigen presentation. This two-stage process can be utilized very generally for the targeted, efficient modulation of the immune reaction of an individual.

Special molecules have been developed as tool for achieving these effects and are referred to below in this patent application as "modular antigen transporter" molecules or MAT molecules. These MAT molecules, associated nucleic acids, vectors, cells, cell lines, vesicles, immunoglobulins, and uses and methods which belong to the invention and which relate to these constituents or operate with them are characterized in detail in the claims.

A previously undescribed combination of at least three modules to give a novel class of molecules, which are referred to as MAT molecules (modular antigen transport molecules), is provided to achieve the object. These three modules include at least one translocation module, at least one targeting module and at least one antigen module. The three different modules are coupled to one another via covalent or noncovalent linkages. The MAT molecule prepared in this way can be administered directly to an individual whose immune reaction to the antigens present in the MAT molecule is to be influenced. Alternatively, it is also possible for cells to be treated with MAT molecules in vitro, and for the cells thus treated subsequently to be administered to the individual. In this method, the translocation modules have the effect that the MAT molecule can penetrate into the cell, the targeting modules have the effect that the MAT molecule undergoes intracellular processing so that there is an immune response, and the identity of the antigens in the antigen modules determines the antigen against which the immune reaction is directed. A substantial advantage of this novel method for modulating the immune response of an individual is in particular its universal applicability, i.e. it can operate with a wide variety of antigens, various translocation modules and various targeting modules. In addition, the use of a translocation module results in the method not being tissue- or cell-specific, but being suitable universally for immunomodulation of virtually all types of cells. A further advantage is the modular structure of the MAT molecule. The modular structure permits the MAT molecule to adapt quickly to the particular medical requirements. It is also possible to vary the exact arrangement of the three constituents of the MAT molecule and the nature of their connection together, as long as at least one module of all three types of modules is present in the MAT molecule. There are no restrictions relating to the antigens on the basis of the method. The method can be used for example for activating the immune system of an individual against pathogens such as, for example, against viruses, bacteria, parasites, etc., i.e. very generally as vaccine. In addition, the method can be used to activate the immune system against degenerate cells such as, for example, tumor cells, etc. However, it can also be used on the other hand for desensitization of the immune system of an individual against allergens such as, for example, pollen, animal hair, house dust mites, insect toxins, etc. or for targeted suppression of the immune system, e.g. if autoimmune reactions are present, such as, for example, arthritis, rheumatism, diabetes, SLE (systemic lupus erythematosus), etc., and for suppressing transplant rejection reactions. Further disorders which are not expressly mentioned and which are associated with an immune reaction which is too strong or too weak can likewise be treated with the MAT molecules of the invention.

It has to date in the prior art frequently been regarded as very disadvantageous that translocation sequences are not specific for particular types of cells, but are equally active in all types of cells [9]. However, in the present invention, the universal functionality of translocation modules is a great advantage which has not been realized in the prior art to date. It has often been attempted in the prior art to date to protect "cargo molecules", which are inserted into cells with the aid of translocation sequences, from proteolytic degradation in the cell [9]. In the present invention it is exactly the opposite which is expressly desired and advantageous for the mode of action of the invention. Proteolytic degradation of the antigen modules in the cell is advantageous for the effect of the invention, i.e. for efficient antigen presentation. The targeting modules therefore employed in the present invention specifically promote the transport of the antigen modules into cell compartments where they undergo proteolytic degradation.

The best-known amino acid sequences which can be used as translocation module for the purposes of the invention are the HIV Tat and the VP22 sequence. It is described for these sequences that they bring about both a translocation through the cell membrane and a transport into the cell nucleus [7]. This transport into the cell nucleus is undesired in connection with the present invention, because no antigen processing takes place in the cell nucleus, and thus efficient antigen presentation does not occur. This previously unsolved problem is solved by the present invention through the use of a targeting module that has the effect that the MAT molecule is not transported intracellularly into the cell nucleus, but is transported specifically into those organelles in which antigen processing or the loading of MHC molecules with antigen take place. The intracellular translocation module of the MAT molecules of the invention therefore eliminates a substantial disadvantage shown by Tat antigen fusion proteins disclosed in the prior art to date.

Also known in the prior art to date are fusion proteins consisting of a targeting sequence, e.g. the invariant chain of the MHC II molecule, and of an antigen. However, these fusion proteins are incapable of efficient penetration into antigen-presenting cells. For this, when they are used for immunizing an individual, additionally an adjuvant that promotes uptake of the fusion protein into the cell is necessary. These adjuvants such as, for example, mineral oil, mycobacterial extracts or Freund's adjuvant have, however, unwanted side effects such as, for example, local inflammatory reactions. The MAT molecules used in the present invention now have the advantage over conventional vaccines that they are coupled directly to a physiologically well-tolerated translocation module that very effectively promotes uptake into cells. It is thereby possible in some circumstances to dispense wholly or partly with additional adjuvants. The result of this is that distinctly fewer unwanted side effects will occur with immunizations using MAT molecules.

It has long been known that extra- or intracellular MHC I presented antigens lead to a cytotoxic immune response, but not to a strong protective humoral immune response. However, it is possible through the use of MAT molecules for the antigens present in the antigen module to be added extracellularly, but they act like intracellular antigens, because the translocation module transports the antigen into the intracellular space, and the targeting module influences intracellular transport of the antigen in such a way that there is a humoral immune response. It is possible through this novel method to achieve the strong induction, which has been desired for many years, of a humoral immune response with antigens added extracellularly (MAT molecules).

For this purpose, in contrast to the prior art to date, two mechanisms known per se are combined in a novel way in this invention, so that immunization with antigens is substantially improved. These mechanisms are in both cases targeted antigen transport mechanisms which overall lead to a very efficient immune response. Each of these two transport mechanisms is brought about by a defined module of the MAT molecule. Those concerned are:

1. transport of the antigen from the extracellular space into the intracellular space (translocation module) in combination with 2. transport of the antigen within the cell specifically to the organelles responsible for antigen processing (targeting module)

This leads to the result: very efficient immunization, only IgG, no IgE This novel combination of 2 known transport mechanisms leads to the possibility of immunization for example with much lower antigen concentrations, and additionally has the very great and surprising advantage that an immune response of the Th1 type mainly occurs, i.e. an immune response in the form of IgG antibodies and not in the form of allergy-causing IgE antibodies.

Translocation Sequences/Translocation Modules

The terms translocation sequence and translocation module are used side by side in the text of the present application as equivalent and having the same meaning. The term translocation module was introduced in order to make it clear that translocation modules are only one part of a MAT molecule for the purposes of the invention. In addition, translocation modules represent not only naturally occurring translocation peptide sequences such as, for example, HIV tat, but also, for example, peptidomimetics or other structures which are able to undertake the same function as the naturally occurring translocation peptide sequences.

The invention includes the use of various translocation modules for preparing MAT molecules which consist at least of one translocation module, at least one targeting module and at least one antigen module. In general, all translocation sequences which are currently known and will be known in future are suitable to be used for the purposes of the present invention. Numerous suitable translocation sequences are described in the literature. These translocation sequences include viral sequences, homeoprotein sequences, leucine zipper sequences, arginine- and lysine-rich sequences, and various other sequences of proteins which are secreted despite the absence of a secretion signal sequence, etc.

Viral Peptide Sequences Suitable as Translocation Modules

The peptide sequences suitable as translocation modules for the purposes of this invention include inter alia viral proteins or partial sequences of viral proteins such as, for example, the protein HIV transcriptional activator protein (HIV tat). The suitable Tat proteins include besides the Tat protein of the HIV-1 virus also the Tat proteins of other lentiviruses [9]. Numerous modified Tat peptides have been described as sequences able to bring about translocation. These include Tat peptides which represent only partial sequences of the Tat protein [10], Tat peptides which comprise point mutations [10], Tat peptides in which the sequence is reversed (inverted) [10], or Tat peptides which comprise unusual amino acids such as, for example, D isomers of amino acids [10], etc. All these variations of peptide sequences are therefore generally suitable as translocation modules. Peptides also suitable for the purposes of the present invention as translocation modules are those derived from other viruses such as, for example, VP22 (herpes simplex virus-1 VP22 tegument protein) [9]. At present, commercial expression vectors comprising a VP22 sequence suitable for translocation are also available. These expression vectors therefore permit VP22 fusion proteins to be prepared (Voyager™ VP22 system, Invitrogen, Breda, the Netherlands). However, no targeting module is present in the fusion protein on use of this expression system. Other viruses, e.g. Marek's disease virus-1, a virus which causes lymphoma in chickens, also express a protein which is related to VP22 and which is likewise suitable as translocation module [11]. These proteins and partial sequences of these proteins are mentioned only as examples, and numerous further peptides are known at present, and will become known in future, which are suitable as translocation modules for the purposes of the invention.

Homeoproteins Suitable as Translocation Modules

A further group of translocation modules suitable for the purposes of the present invention are peptides derived from the drosophila homeotic protein antennapedia (ANTp) [9]. Among others, ANTp peptides suitable as translocation module are those comprising an inverted sequence of ANTp [7], comprising D isomers of amino acids [7], or comprising point mutations in their sequence [7]. It is additionally expected that numerous further ANTp sequence modifications are also possible and will presumably make translocation possible [7]. ANTp peptide variants are also referred to as transport peptides. Further homeoproteins such as, for example, engrailed 1 (En1), engrailed 2 (En2), Hoxa-5, Hoxc-8, Hoxb-4 and KNOTTED-1 [7] likewise comprise sequences which can be used as translocation module for the purposes of the present invention. KNOTTED-1 is in fact a plant protein, but is likewise suitable as translocation module in animal cells. These peptides are mentioned only as examples, and numerous further homeoproteins which comprise peptide sequences which may be suitable as translocation module for the purposes of the invention are known [12]. Further previously undisclosed homeoproteins may also comprise sequences suitable as translocation module.

Leucine Zipper Proteins Suitable as Translocation Module

A further group of sequences suitable as translocation module for the purposes of the present invention are peptides comprising a leucine zipper domain. Examples of proteins whose leucine zipper domains can be used as translocation sequence are, for example, human cFos-(139-164), human cJun-(252-279), or the yeast transcription factor yeast GCN4-(231-252) [8]. Further leucine zipper proteins already known or which will become known in future are likewise suitable as translocation module for the purposes of the invention.

Arginine- or Lysine-Rich Peptides Suitable as Translocation Module

Arginine-rich peptides, frequently derived from RNA- and DNA-binding proteins, represent further peptide sequences which can be used as translocation modules for the purposes of the present invention. Examples of such sequences are HIV-1 rev-(34-50), flock house virus coat protein FHV coat-(35-49), BMV Gag-(7-25), HTLV-II Rex-(4-15), CCMV Gag-(7-25), P22 N-(14-30), lambda N-(1-22), phi 21 N-(12-29) and PRP6-(129-144) from yeast [8]. It is likewise possible to use for the purposes of the invention polyarginine peptides having 4 to 16 [8] or else having more than 16 arginine residues. In addition to polyarginine peptides, peptides which can also be used as translocation modules are those which, besides arginine, also comprise further amino acids, e.g. the W/R peptide (RRWRRWWRRWWRRWRR (SEQ ID NO: 37) [9] or the R9-Tat peptide in which the 9 central amino acid residues of the total of 11 amino acids of a Tat peptide have been replaced by arginine residues (GRRRRRRRRRQ) (SEQ ID NO: 38) [8]. It has additionally been possible to show that peptides which for example consist of nine lysine residues also have the ability to act as translocation module for the purposes of the invention [13]. These peptides are mentioned only as examples and numerous further arginine- or lysine-rich peptides are suitable to be used as translocation module for the purposes of the invention [8, 13]. Further arginine- or lysine-rich peptides currently already known or to become known in future are presumably also suitable as translocation module. Sequences comprising guanidino or amidino groups are also suitable as translocation module for the purposes of the present invention [14].

Proteins without Signal Sequence which are Suitable as Translocation Module

A number of further proteins have the ability, without a secretion signal sequence being present, to penetrate the cell membrane from the inside to the outside, i.e. be secreted. These proteins are frequently also able conversely to penetrate into the interior of the cell from the outside. These proteins or partial sequences of these proteins can thus also be used as translocation modules for the purposes of the present invention. Some exemplary examples of such proteins are fibroblast growth factor 1 (FGF-1), fibroblast growth factor 2 (FGF-2), caveolin-1, lactoferrin, thioredoxin, interleukin 1 beta and ciliary neurotrophic factor (CNTF) [7], or interleukin 1 alpha, vas deferens protein, platelet-derived endothelial cell growth factor (PR-ECGF), thymosin, para-thymosin, 14.5 kDa lectin (L14), transglutaminase, thioredoxin-like protein (ADF), sciatic nerve growth-promoting activity, factor XIIIa, mammary-derived growth inhibitor, galectin, rhodanase [15]. These peptides are mentioned only as examples, and numerous further peptides are known or will become known in future which are suitable as translocation module for the purposes of the invention.

Toxins Suitable as Translocation Module

Many toxins or partial sequences of toxins have the property of acting as translocation module, such as, for example, following toxins: complete abrin, complete ricin, complete modeccin, complete pseudomonas exotoxin A, complete diphtheria toxin, complete pertussis toxin, complete Shiga toxin, the A chain of ricin, the A chain of abrin, the A chain of modeccin, the enzymatically active domain of pseudomonas exotoxin, the A chain of diphtheria toxin A, the enzymatically active domain of pertussis toxin, the enzymatically active domain of Shiga toxin, gelonin, pokeweed antiviral protein, saporin, tritin, barley toxin and snake venom peptides [16]. These toxins mentioned as examples, and many further other toxins not expressly mentioned or toxins to become known in future can be used as translocation module for the purposes of the present invention.

Controlling the Efficiency of Translocation Modules

The efficiency of translocation can be controlled by varying the length of, for example, a poly-arginine chain or by specific selection of, for example, only a partial sequence of the HIV Tat sequence, so that very efficient translocation of the corresponding MAT molecule, or a less efficient translocation takes place, depending on the particular requirements [8, 13]. A very efficient translocation may have the advantage that the efficacy of the MAT molecule is increased and/or that the necessary dose of MAT molecule can be reduced, in turn saving vaccine costs. A reduced dose of MAT molecule in turn has the advantage that fewer side effects occur. On the other hand, a reduced efficiency of translocation makes it possible for the MAT molecules to be distributed widely in the treated individual, e.g. after intravenous injection, because they do not immediately penetrate locally and virtually quantitatively into all cells located in the vicinity.

Examples of Minimal Sequences Acting as Translocation Module

It is not necessary for all the translocation sequences mentioned as examples to be in the form of the complete protein as constituent of the MAT molecule in order to be effective as translocation module for the MAT molecule for the purposes of the invention. On the contrary, a minimal sequence region which can be used as translocation sequence is known for many of said proteins. This sequence region includes for example for HIV Tat for example the following sequence: Tyr-Gly-Arg-Lys-Lys-Arg-Arg-Gln-Arg-Arg-Arg (SEQ ID NO: 39), for VP22 the following sequence: Asp-Ala-Ala-Thr-Ala-Thr-Arg-Gly-Arg-Ser-Ala-Ala-Ser-Arg-Pro-Thr-Glu-Arg-Pro-Arg-Ala-Pro-Ala-Arg-Ser-Ala-Ser-Arg-Pro-Arg-Arg-Pro-Val-Glu (SEQ ID NO: 40) and for antennapedia the following sequence: Arg-Gln-Ile-Lys-Ile-Trp-Phe-Gln-Asn-Arg-Arg-Met-LysTrp-Lys-Lys (SEQ ID NO: 41) [17]. It is additionally possible for the sequences also to be used in the form of fragments which do not correspond to the currently known minimal functional sequence segments, as long as the resulting sequence is still functional for the purpose of the translocation module.

Translocation modules need therefore not be in the form of the complete protein or the complete molecule as constituent of the MAT molecule in order to be effective as translocation module for the MAT molecule for the purposes of the invention. On the contrary, a sequence region which can be used as translocation module is known for example for some of the proteins mentioned. In addition, the protein sequences may also be used in the form of fragments which do not correspond to the previously disclosed functional sequence segments, as long as the resulting sequence is still functional as translocation module. Testing of the functionality of a translocation module can be ascertained for example by using fluorescence-labeled translocation modules or by using enzyme-labeled translocation modules or by using translocation modules labeled with metal particles. The translocation modules labeled in these ways are administered to an experimental animal or to cells cultivated in vitro, and the fate of the translocation modules is followed using methods such as FACS (fluorescence activated cell sorting), microscopy, confocal fluorescence microscopy, electron microscopy etc. These techniques for checking the functionality of translocation modules are described in the literature, and some of them have already been used to ascertain the functionality of sequences for translocation [8, 18].

Targeting Sequences/Targeting Modules

The terms targeting sequence and targeting module are used side by side in the text of the present application as equivalent and having the same meaning. Targeting in principle always means intracellular targeting in this patent application. The term targeting module was introduced in order to make it clear that translocation modules are only one part of a MAT molecule for the purposes of the invention.

The invention includes the use of various sequences as targeting modules for preparing MAT molecules which consist at least of one translocation module, at least one targeting module and at least one antigen module. In general, all amino acid sequences and molecules which are currently known and will become known in future and which are able to mediate targeting are suitable to be used as targeting modules for the purposes of the present invention. Numerous suitable sequences are described in the literature. Sequences included in these sequences suitable as targeting module are all those which have the effect that the MAT molecule is transported intracellularly to the sites or organelles within a cell at which processes involved in the presentation of the antigen modules present in the MAT molecule take place. These sites and organelles within the cell include, in particular, MHC class II compartments (MIICs), endosomes, lysosomes, the Golgi apparatus, the trans-Golgi network and the endoplasmic reticulum. These intracellular organelles are involved in processes such as, for example, the transport or processing of antigens, the preparation and loading of MHC II molecules with antigens or processed antigens, and the transport of the MHC II molecules loaded with antigens to the cell surface etc.

MHC Molecules Comprising Sequences Suitable as Targeting Module

A number of sequences are suitable in particular as targeting modules for the purposes of the invention. The invariant chain of the MHC II molecule (Ii, invariant chain, MHC II gamma chain) is the sequence described most often in the literature as being able to mediate targeting. Various variants of the invariant chain in humans are described and are also referred to as IiP33, IiP41, IiP35 and IiP43 [1] and which are suitable as targeting modules. Further sequences suitable as targeting module for the purposes of the invention are the beta chain of the MHC II molecule [19]. Fragments of said sequences are also suitable as targeting module.

Lysosomal Membrane Proteins Comprising Sequences Suitable as Targeting Module

A number of membrane proteins which occur in lysosomes and are one of the major protein constituents there have sequence motifs which bring about targeting for the lysosome. This group of proteins includes inter alia Lamp 1 (lysosomal-associated membrane protein-1), Lamp 2, Lamp 3, Limp II (lysosomal integrated membrane protein II) and LAP (lysosomal acid phosphatase) [4]. These and other lysosomal proteins which are currently known or are to become known in future and which have targeting sequence motifs can be used as targeting modules for the purposes of the invention, it being possible to use the complete protein sequence or partial sequences thereof as targeting module.

Tetraspan Proteins Comprising Sequences Suitable as Targeting Module

The members of a family of proteins which have four membrane-spanning domains (tetraspan proteins) are likewise suitable as targeting modules for the purposes of the invention, because these proteins enter MIICs very efficiently. The mechanism by which "tetraspan" proteins enter MIICs is unclear because they comprise no known amino acid sequences which make targeting possible. Despite this, there are mechanisms which transport these proteins into the MIICs, meaning that they can be used as targeting modules for the purposes of the present invention. The family of "tetraspan" proteins includes CD37, CD53, CD63 (also known as Limp-I and LAMP-3), CD81, CD82 and CD86 [20]. It is known for CD63 and CD82 that they associate with MHC II, HLA-DO and HLA-DM molecules [20]. "Tetraspan" proteins are likewise present in the membranes of exosomes. Exosomes are vesicles which are formed after fusion of MIICs with the plasma membrane and thus are released by the antigen-presenting cell. Exosomes comprise MHC II molecules and are able to present antigens and thus stimulate T cells [20]. Further proteins which are very similar to the "tetraspan" protein family, and which are therefore likewise suitable as targeting module for the purposes of this invention, are the *Schistosoma mansoni* membrane protein SM23 and the tumor-associated antigen CO-029 [21]. Further tetraspan proteins, or partial sequences of tetraspan proteins, not expressly mentioned or currently as yet unknown may likewise comprise sequences which are suitable as targeting modules.

Further Proteins Having Sequences Suitable as Targeting Modules

Numerous further proteins are to be found in the endosomal/lysosomal compartment of various cell types and therefore reach it via certain mechanisms which are currently known only in part. These proteins or partial sequences of these proteins are accordingly also suitable to be used as targeting modules for the purposes of the present invention. These proteins present in the endosomal/lysosomal compartment include inter alia the low density lipoprotein (LDL), insulin, epidermal growth factor (EGF), polymeric immunoglobulin, transferrin, the cation-dependent mannose 6-phosphate receptor, the cation-independent mannose 6-phosphate receptor, CD3, etc. [21], and CD1b [22], and many further proteins or protein sequences which are currently known or to become known in future and which permit targeting into the endosomal/lysosomal compartment. These sequences can be used as targeting module for the purposes of the invention. Various commercial suppliers supply expression vectors comprising nucleic acid sequences which code for sequences suitable for targeting. For example, both BD Bioscience Clontech (Palo Alto, Calif., USA) and Stratagene (La Jolla, Calif., USA) supply expression vectors with targeting modules which guide the resulting fusion protein to the Golgi apparatus or to the peroxisomes. However, these expression vectors do not allow fusion proteins comprising a translocation module to be prepared, so that they differ from the MAT molecules of the invention. In the Clontech vectors for example a sequence of calreticulin (KDEL "retrieval sequence", SEQ ID NO: 42) is used for targeting the fusion protein to the Golgi apparatus. Further proteins which are not expressly mentioned or are currently as yet unknown may likewise comprise sequences suitable as targeting modules for the purposes of the invention.

Sequence Motifs which Occur in Certain Groups of Targeting Sequences

Certain sequence motifs have been ascertained to be important for the function of various protein sequences as targeting module. For the beta chain of HLA-DM for example the sequence motif tyrosine-threonine-proline-leucine (SEQ ID NO: 43) has been identified as targeting motif, with the tyrosine residue and the leucine residue apparently being of particular functional importance [2]. Tyrosine motifs important for intracellular targeting have been identified for various lysosomal membrane proteins such as LAP (lysosomal acid phosphatase), Lamp 1 (lysosomal associated membrane protein 1), Lamp 2 and Lamp 3 [3, 4] and for CD1b [22]. It was possible to identify a leucine motif important for intracellular targeting for a further lysosomal protein, Limp II (lysosomal integrated membrane protein II) [4]. It was possible to show for Ii that two sequence regions are important independently of one another for the intracellular targeting (amino acid position 1 to 11 and position 12 to 29) [23]. Both targeting sequences are functional even on their own, and the sequence 1 to 11 comprises a functionally essential leucine-isoleucine motif at position 7 and 8 [23]. The beta chain of the MHC II molecule likewise comprises a sequence motif which comprises one or two functionally important leucine residues, and a conserved glycine residue is located N-terminally directly preceding this leucine motif [19]. In summary, accordingly, leucine and tyrosine residues in particular have an important function in targeting sequences and it is therefore possible to design specifically appropriate amino acid sequences as targeting modules. These can be used as targeting modules for the purposes of the invention.

"Non-Amino Acid Structures" which can be Used as Targeting Modules

Molecules which do not correspond to an amino acid sequence or an amino acid can also be employed as targeting modules for MAT molecules for the purposes of the invention. An example which has long been known for a structure suitable for targeting in lysosomes is, for example, mannose 6-phosphate [24]. Proteins which comprise mannose 6-phosphate residues are transported by various mannose 6-phosphate receptors to the lysosomes. This mechanism can be used for the purposes of the invention to transport the MAT molecule into the lysosomes in order thus to achieve efficient presentation of the antigen. For this purpose, mannose 6-phosphate residues can be coupled covalently or noncovalently, alone or as constituent of more complex sugar structures, to the MAT molecule. It is generally possible to use all ligands of mannose 6-phosphate receptors as targeting modules for MAT molecules for the purposes of the present invention. Further currently known structures or structures to become known in future, which make it possible to target MIICs, endosomes, lysosomes, the Golgi apparatus, the trans-Golgi network or the endoplasmic reticulum, can be used as targeting module for the purposes of the invention.

All the targeting modules mentioned by way of example need not be in the form of the complete protein or the complete molecule as constituent of the MAT molecule in order to be effective as targeting module for the MAT molecule for the purposes of the invention. On the contrary, a sequence region which can be used as targeting module is known for example for some of the proteins mentioned. In addition, the protein sequences mentioned by way of example may also be used in the form of fragments which do not correspond to the previously disclosed functional sequence segments, as long as the resulting sequence is still functional as targeting module. Testing of the functionality of a targeting module can be ascertained for example by using fluorescence-labeled targeting modules or by using enzyme-labeled targeting modules or by using targeting modules labeled with metal particles. The targeting modules labeled in these ways are administered to an experimental animal or to cells cultivated in vitro, and the fate of the targeting modules is followed using methods such as FACS (fluorescence activated cell sorting), microscopy, confocal fluorescence microscopy, electron microscopy etc.

Antigen Modules

It is possible to employ as antigen modules for the purposes of the invention in principle all types of antigens able to modulate an immune response. Both antigens currently already known and antigens to be discovered in future are suitable. In some circumstances, the antigens may also be those which do not lead to an immune response with conventional immunization methods known in the art at present but which lead on application of the novel method described in the present patent application to an immune response by the individual. Further, the term antigen encompasses antigenic fragments comprising the antigenic determinant/the antigenic determinants which are also known as epitope/s). Thus, the antigen module may be the whole molecule, e.g. the protein, or is a part of the molecule, i.e. a fragment thereof, like a peptide, encompassing at least one antigenic determinant or epitope. The at least one antigenic determinant or epitop is able to elicit an immune response against the antigen. The epitope can comprise one or more than one amino acid or peptid or other structure capable to elicit an immune response such as sugar structures, phosphorylated amino acids, etc. or combinations thereof. The allergen can be a continuous epitope (=not dependent on conformation=present in for example native and denatured proteins) or a discontinious epitope (=dependent on conformation=only present in native, folded, but not present in denatured proteins). Epitopes comprise preferably at least 4, at least 5, at least 6, at least 8, at least 10, least 15, at least 20 amino acids or other structures suitable as epitope and resulting in structures of about the same physical size. It is possible to use not only proteins and peptides, but also sugar structures, lipids, e.g. lipopolysaccharides, lipoteichoic acids and other constituents of bacterial membranes (CD1b binds, for example, sugar structures and lipids), nucleic acids such as, for example, DNA comprising CpG motifs, organic substances such as, for example, latex or pharmaceutically active substances as antigen for the purposes of the invention. The antigen may be derived from humans, animals, plants, fungi, parasites, unicellular or multicellular microorganisms, viruses and other life forms. The antigens may have been isolated from biological material, have been prepared as recombinant antigens or have been prepared by synthesis, e.g. by peptide synthesis. Synthetically prepared antigens may be substances which occur in nature or which do not occur in nature but are obtainable by chemical synthesis. Examples of non-naturally occurring substances which are, however, suitable as antigen in some circumstances are, for example, synthetically prepared substances which are present in medicaments, or synthetic peptides having amino acid sequences which do not occur in nature, or peptidomimetics, etc. Naturally occurring or synthetic or recombinant antigens can be modified by molecular-biology, enzymatic, chemical and other methods in order to confer on them properties which are more advantageous for the particular application. These advantageous properties may be, inter alia, a higher or lower activity as antigen, a broader or a more specific action as antigen, a better solubility in hydrophilic or hydrophobic solvents, a greater permeability of the antigen modules for cell membranes, for membranes of organelles, for the blood-brain barrier, for the blood-CSF barrier etc., a higher or lower half-life in vivo or in vitro, a lower or higher toxicity, a better detectability of the antigen in vivo or in vitro after application of the antigen in the form of a MAT molecule etc. It is additionally possible for the purposes of the invention to combine a plurality of antigens in an antigen module [25]. For this it is possible for identical antigens to be present in more than one copy in the antigen module, or it is possible for example for different variants of the same antigen to be combined in an antigen module. Combination of antigens, e.g. of antigen 1, and other antigens, e.g. of antigen 2, in an antigen module is also possible, etc. Further combinations such as, for example, antigen 1 in more than one copy and antigen 2 in a single copy may also be combined in an antigen module, etc. It is additionally possible also for one or more different and/or one or more identical antigen modules to be present in a MAT molecule. It is possible in principle for all possible combinations of singly and multiply present identical or altered copies of antigens derived from one or more different antigen to be combined for the purposes of the invention.

Antigens and Allergens which can be Used as Antigen Module

Numerous antigen or fragments thereof comprising the antigenic determinant, in particular allergens, have been described in the literature to date. The allergens or fragments thereof comprising the antigenic determinant or epitope specifically known hereinafter can be used as antigen module for the purposes of the invention. Further allergens and variants of allergens which can likewise be used as antigen module for the purposes of the invention are known in the art [26, 27]. That means, the antigen module according to the present invention preferably comprises at least one epitope, which is potentially capable to trigger an immune response, in particular an allergic response. Preferably the complete molecules or fragments thereof of the allergens Fel d 1, Bet v 1, Api g 1, Der p 1 and PLA2 are used according to the invention as an antigen module within a MAT-molecule. Furthermore certain allergenes may show cross reactivity to each other, such as for example Bet v 1 and Api g 1 (Eur J Biochem, 1995, 233:484-489). Furthermore certain sources of allergens contain not only one major allergen almost exclusively responsible for the allergic reactions, but instead do contain small groups of preferably 2 to 10 different allergy-promoting substances. These allergy-promoting substances can be combined for allergy-treatment in the form of individual MAT-molecules, each MAT-molecule comprising a different allergen as antigen-module. Alternatively these substances can be combined in one or several MAT-molecules which MAT-molecules each contain more than one allergen as an antigen-module within the MAT-molecule. Examples of such sources of multiple allergens among others are *Phleum pratenses, Dermatophagoides pteronissinus, Dermatophagoides farinae, Artemisia vulgaris, Aspergillus fumigatus, Alternaria alternata* and *Cladosporium herbarum*.

The following list of allergens are arranged according to groups such as allergens from plants and grasses, from trees, from mites, from fungi, from insects, from foods and from other allergens such as, for example, latex allergens. The listing in the enumerations is as follows: scientific name of the organism, a commonly used abbreviation of the allergen directly followed by the GeneBank accession No. of the allergen (written in parentheses), where known.

Plant and Grass Allergens:
 *Ambrosia artemisiifolia*, Amb a 1 and Amb a 2; *Mercurialis annua*, Mer a 1 (Y13271); *Parietaria judaica*, Par j 1 (X77414), Par j 2 (X95865; X95866); *Cynodon dactylon*, Cyn d 1 (S83343); *Dactylis glomerata*, Dac g 3 (U25343); *Holcus lanatus*, Hol l 1 (Z27084, Z68893); *Lolium perenne*, Lol p 1 (M57474), Lol p 2 (X73363) Lol p 5 (M59163); *Phalaris aquatica*, Pha a 1 (S80654); *Phleum pratense*, PhI p 1 (X78813), PhI p 2 (X75925), PhI p 3, PhI p 5 (X74735); *Artemisia vulgaris*, Art v 1 (Z48967)

Tree Allergens:
 *Alnus glutinosa*, Aln g 1 (S50892); *Betula verrucosa*, Bet v 1 (X15877), Bet v 2, Bet v 1d; *Carpinus betulus*, Car b 1 (X66932, X66918); *Corylus avellana*, Cor a 1 (X70999, X71000, X70997, X70998, Z72439, Z72440, AF136945, AF323973, AF323974, AF323975); *Ligustrum vulgare*, Lig v 1 (X77787, X77788); *Olea europea*, Ole e 1 (S75766), Ole e 9 (AF249675); *Syringa vulgaris*, Syr v 1 (X76541); *Cryptomeria japonica*, Cry j 1, Cry j 2 (D29772, D37765); *Cupressus arizonica*, Cup a 1 (AJ278498); *Cupressus sempervirens*, Cup s 1 (AF257491); *Juniperus ashei*, Jun a 2 (AJ404653)

Mite Allergens:
 *Blomia tropicalis*, Blo t 5 (U59102); *Dermatophagoides farinae*, Der f 1, Der f 2, Der f 11; *Dermatophagoides pteronyssinus*, Der p 1, Der p 2, Der p 5, Der p 7; *Lepidoglyphus destructor*, Lep d 2 (X81399); *P. americana*, Cra-A; *T. putrescentiae*, Tyr p 2

Animal Allergens:
 *Bos domesticus*, Bos d 2 (L42867); *Equus caballus*, Equ c 1 (U70823); *Felis domesticus*, Fel d 1 (M74952, M74953)

Fungal Allergens:
 *Alternaria alternata*, Alt a 1 (U82633), Alt a 2 (U62442); *Aspergillus flavus*, Asp fl 1 (AF137272); *Aspergillus fumigatus*, Asp f 1 (M83781, S39330), Asp fl/a, Asp f 2 (U56938), Asp f 3 (U20722, U58050), Asp f 4, Asp f 6, Asp f 8; *Aspergillus niger*, Asp n 18; *Aspergillus oryzae*, Asp o 13 (X17561); *C. comatus*, Cop c 1; *Penicillium chrysogenum*, Pen ch 13 (AF193420), Pen ch 20 (S77837); *Penicillium oxalicum*, Pen o 18 (AAG44478); *Malassezia sympodialis*, Mal s 1 (X96486); *Cladosporium herbarum*, Enolase, Cla h1

Insect Allergens:
 *Apis mellifera*, Api m 1 (X16709), Api m 2 (L10710), Api m 4 (X02007); PLA2 (X16709); *Blattella germanica*, Bla g 1 (AF072219, L47595, AF072221, AF072220), Bla g 2 (U28863), Bla g 4 (U40767), Bla g 5 (U92412); *Periplaneta americana*, Per a 1 (AF072222), Per a 3 (L40819); *Dolichovespula maculata*, Dol m 1 (X66869), Dol m 2 (L34548), Dol m 5 (J03601); *Dolichovespula arenaria*, Dol a 5 (M98859); *Polistes annularies*, Pol a 5 (M98857); *Vespula vulgaris*, Ves v 1 (L43561), Ves v 2 (L43562), Ves v 5 (M98858); *Myrmecia pilosula*, Myr p 1 (X70256), Myr p 2 (581785)

Food Allergens:
 *Salmo salar*, Sal s 1 (X97824); *Bos domesticus*, Bos d 4 (M18780), Bos d 5 (X14712); *Gallus domesticus*, Gal d 1 (J00902), Gal d 2 (J00992); *Metapenaeus ensis*, Met s 1 (U08008); *Hordeum vulgare*, Hor v 15 (X63517); *Oryza sativa*, Ory s 1 (U31771); *Apium graveolens*, Api g 1 (Z48967); *Daucus carota*, Dau c 1 (U47087, D88388); *Malus domestica*, Mal d 1 (X83672); *Pyrus communis*, Pyr c 1 (AF057030); *Persea americana*, Pers a 1 (Z78202); *Prunus armeniaca*, Pru ar 1 (U93165); *Prunus avium*, Pru av 1 (U66076); *Arachis hypogaea*, Ara h 1 (L34402), Ara h 2 (L77197); *Bertholletia excelsa*, Ber e 1 (M17146); *Juglans regia*, Jug r 1 (U66866), Jug r 2 (AF066055); *Ricinus communis*, Ric c 1 (X54158); *Sesamum indicum*, Ses i 1 (AF240005); *Apium graveolens*, Api g 1 (Z48967)

Further Allergens (Latex):
 *Hevea brasiliensis*, Hev b 1 (X56535), Hev b 2, Hev b 3, Hev b 5 (U42640), Hev b 6 (M36986), Hev b 7, Hev b 8 These known allergens are mentioned merely by way of example, and further allergens which can likewise be used in antigen modules for the purposes of the invention are known in the art.

In a preferred embodiment, the antigen module comprises the Fel d 1 or fragments thereof. The allergen Fel d 1, i.e. the Fel d 1 antigen, is a protein composed of two chains, chain 1 and chain 2. In nature, these two chains are connected by disulfide bridges and form a heterodimer known as Fel d 1. In a particularly preferred embodiment, the antigen module comprises the Fel d 1 chains 2 and 1 being covalently linked to one another. The order of the two chains is not decisive, however, it is preferred that chain 2 is at the N-terminus of the antigen module and chain 1 is at the C-terminus, as this more accurately resembles the native conformation of Fel d 1 (Grönlund et al., 2003, J Biol Chem, 278:40144-40151; WO 2004/094639 A2). Between these two covalently linked chains spacer modules may be present. Of course, the antigen module may contain only one of these two Fel d 1 chains or only fragments of one or both of these chains. The Fel d 1 antigen module may also comprise more than one copy of at least one fragment or epitope of Fel d 1 and/or the Fel d 1 antigen module may comprise modifications of the Fel d 1 sequence as described elsewhere in this patent application. The sequences of Fel d 1 are disclosed in U.S. Pat. No. 5,328,991 which is incorporated herein by reference.

Besides allergens, there are a number of known pathogens against which no effective or lasting immunization is available at present. Since the method of the invention is based on a novel immunization strategy, it is possible that shows an effect for immunization against these disorders which cannot to date be satisfactorily treated prophylactically by immunizations. These disorders include, in particular, infections with HIV viruses, with hepatitis C viruses, with pathogens of tuberculosis (*Mycobacterium tuberculosis*), leprosy (*Mycobacterium leprae*), plague (*Yersinia pestis*) and with malaria pathogens (Plasmodium species, e.g. *falciparum*).

Further Modules which May be Present in MAT Molecules

Besides the three modules already described—translocation module, targeting module and antigen module—which must be present at least in the MAT molecule, it is also possible for further optional modules to be present in the MAT molecule. These optional modules include, for example, modules which make it possible to isolate or detect the MAT molecules. Such modules are often referred to in the art as "tags" and are therefore referred to as tag modules in this patent application below. Further modules optionally present in the MAT molecules may be spacer modules, i.e. modules which are arranged between the other modules and whose task is to couple these modules to one another. These modules are called spacer modules in this patent application below. It is also possible for certain modules simultaneously to undertake the function of two or more modules. For example, many tag modules can be used simultaneously for isolation and for detection of the MAT molecule, or an antigen module present in a MAT molecule might also be used for detection and/or isolation of the MAT molecule if, for example, an antibody against the antigen module is available, etc.

Tag Modules which May be Present in MAT Molecules

For the purposes of the invention it is possible for one or more different and/or one or more identical tag modules to be constituent of a MAT molecule. Tag modules may be short peptides, frequently consisting of not more than 20 amino acid residues, but may also correspond to complete protein sequences or certain domains of proteins. Tag modules may also be functional groups which are not composed of amino acids, such as, for example, biotin or digoxigenin. Almost all tag modules can be used in two different ways. Firstly, they can be used to isolate the MAT molecule, and secondly they can be used to detect the presence of the MAT molecule. In general, all tag modules currently known and all those to become known in the future are suitable for use for the purposes of the invention. Examples of suitable tag molecules which can be used for the purposes of the present invention are: histidine sequences of 4 to 12 or more, preferably directly consecutive histidine residues, also called His tag, His6 tag, HIS6 tag, penta His™, Tetra His™, RGS His™, etc. (Qiagen, Hilden, Germany), Myc or c-Myc tag, PinPoint™ tag (a signal sequence which has the effect that the corresponding protein is provided with a biotin group by bacteria in vivo), HA tag, 6×HN tag (Promega Biosciences Inc., San Louis Obispo, Calif., USA), Xpress™ tag, myc tag, V5 tag (Invitrogen, Breda, the Netherlands), S tag, CBD tag, GST tag, HSV tag, T7 tag (Novagen Inc., Madison, Wis., USA), FLAG tag, HA tag, c-myc tag, "calmodulin-binding peptide tag (CBP) tag (Stratagene, La Jolla, Calif., USA), His tag, protein A tag, glutathione S-transferase (GST) tag (Amersham Biosciences, Uppsala, Sweden), Strep-tagII (IBA GmbH, Göttingen, Germany), His tag (Roche Applied Science, Rotkreuz, Switzerland), FLAG tag, GST tag, protein A tag (Sigma, St. Louis, Mo., USA), maltose binding protein (MBP), chitin-binding tag (New England Biolabs, Beverly, Mass., USA), His tag (BD Biosciences Clontech, Palo Alto, Calif., USA). Applications in which more than one tag module are used in a molecule have also been described for some of these tag modules. For example, two tag modules can be coupled to the N terminus or to the C terminus of a protein, or one tag module can be coupled to each of the N terminus and C terminus (Qiagen, Hilden, Germany and Stratagene, La Jolla, Calif., USA). Tag modules may also be introduced internally in the sequence of other proteins, e.g. between two domains of a protein (Strep-tagII, IBA, Göttingen, Germany).

Further tag modules are primarily used to detect the molecule to which they are coupled. However, these tag molecules may also be used in principle for isolating proteins, e.g. by use of affinity chromatography. It is possible to use for this purpose for example chromatography materials onto which antibodies against these tag modules are coupled. It is also possible to use for the purposes of the present invention tag modules such as, for example, the green fluorescent protein (GFP), the enhanced green fluorescent protein (EGFP), the enhanced cyan fluorescent protein (ECFP), the enhanced yellow fluorescent protein (EYFP), the red fluorescent protein (DsRed2) (BD Bioscience Clontech, Palo Alto, Calif., USA), the renilla green fluorescent protein (hrGFP) (Stratagene, La Jolla, Calif., USA). These tag modules may be located both at the N terminus and at the C terminus for example of a fusion protein. Besides fluorescent tag modules it is also possible to use enzymes as tag module. Examples of frequently used enzymes are luciferease, beta-galactosidase, alkaline phosphatase, horseradish peroxidase, etc. These enzymes can be detected via their respective enzymic activity, i.e. on the basis of the conversion of substrates of these enzymes. Various types of substrates are suitable for this purpose, such as, for example, substrates which absorb light in the visible region of the spectrum, fluorescent substrates, substrates whose conversion leads to the emission of light, or substrates whose enzymatic conversion can be determined through the decrease in the concentration of the substrate or the increase in the product by use of various detection methods, etc.

A further possible use of tag modules for the purposes of the present invention is the use of, for example, peptide sequences which are suitable as kinase substrates. These peptide sequences can then be radiolabeled by addition of radioactive phosphorus and addition of kinases. Examples of tag modules which can be used in this way for the present invention are: the kemptide tag (a peptide which can be phosphorylated by protein kinase A), the calmodulin-binding peptide tag (CBP), which can likewise be phosphorylated with protein kinase A (Stratagene, La Jolla, Calif., USA), etc.

A further possible use of tag modules for the purposes of the present invention is the use of, for example, proteins, protein domains, or peptide sequences which specifically bind other proteins or other structures. Examples of such tag modules known from the literature are: protein A, protein G, protein A/G, protein L, all these proteins binding to antibody structures (Pierce, Rockford, Ill., USA), glutathione S-transferase, which binds to glutathione, the maltose binding protein (MBP), that binds to amylose, streptavidin or avidin, both of which bind to biotin, the calmodulin-binding peptide, which binds to calmodulin, the chitin-binding tag, which binds to chitin, etc. It is possible in general to use all types of molecules which in each case bind specifically to other molecules as tag module for the purposes of the invention, i.e. receptor-ligand, antibody-antigen, lectin-sugar structure, protein-lipid, protein-nucleic acid, protein-protein, etc., and numerous further examples described in the literature [28].

Spacer Modules

Spacer modules which can be used for the purposes of the invention are all types of molecules suitable for coupling other modules, which are component of the MAT molecule, to one another. The coupling can take place both by covalent and by noncovalent linkages. The spacer modules have the task inter alia of separating the various modules of the MAT molecule from one another in space so that they do not have mutual adverse effects on their functionality. Modules of the MAT molecule for the purposes of the invention can be coupled by spacer modules which can be cleaved again at a later time by chemical or enzymatic reactions, e.g. by proteases. It is thus possible to separate the modules of the MAT molecule, which are connected by the spacer modules, from one another again as required.

It is possible to use for this purpose in general all proteases currently known or to become known in future [29, 30]. Proteases frequently used at present are thrombin, factor Xa, enterokinase or the TAGZyme system (Qiagen, Hilden, Germany) etc. Various chemical reactions suitable for cleaving spacer modules are known to the skilled worker or can be found in the information from manufacturers of spacer molecules, e.g. from Pierce.

The spacer modules may be in particular peptide sequences or organic molecules. Numerous spacer molecules which can be used for the purposes of the invention are known in the art. In addition, it is also possible to use spacer molecules which will be developed or discovered in future for the purposes of the invention. Suitable spacer modules are, inter alia, peptide spacers, crosslinkers, natural or synthetic polymers such as, for example, nucleic acids, substituted or unsubstituted hydrocarbons, etc. It is additionally possible to use combinations of molecules as spacer modules which are able to form complexes with one another via noncovalent interactions, and thus able to join together two or more modules to give a MAT molecule. A known example of such a combination of molecules which bind to one another is biotin/streptavidin.

Peptide Sequences as Spacer Modules

Many proteins consisting of a plurality of domains have in their amino acid sequence short sequence regions which are also referred to as spacers in the literature. These spacers have the task of separating the various domains of the protein spatially from one another in such a way that they do not have mutual adverse effects on their functionality. It is necessary for this purpose in particular to ensure that the spacer sequence is so flexible that the two domains do not impede one another sterically in their function.

Peptide sequences of this type can be used as spacer modules for the purposes of the present invention. A large number of different spacer peptide sequences are described in the literature. These spacers preferably have a length of between 2 and 60 amino acids, but may also have longer sequences. Spacers may also consist of only one amino acid. Many commercially available expression vectors already comprise sequence regions which code for peptide spacers which, for example, connect a tag sequence to the protein sequence to be introduced into the expression vector. Very short peptide spacers consisting of only two amino acids such as, for example, leucine-glycine, glycine-alanine or serine-alanine (IBA GmbH, Göttingen, Germany) are often used, or short amino acid sequences from 4 to 6 amino acids in length consisting of glycine and/or alanine (Qbiogene Inc., Carlsbad, Calif., USA). Numerous further spacer sequences are described in the literature and can be used as spacer modules for the purposes of the present invention. It is possible in principle to employ all currently known spacer molecules and spacer molecules which will become known in future as spacer module in the MAT molecules of the invention. A method for identifying amino acid sequences suitable as spacer module is the use of databases which screen amino acid sequences for protein domains. Short amino acid sequences preferably with a length of from 2 to 60 amino acids, which are present between two protein domains identified in this way in an amino acid sequence, can be used as spacer module for the purposes of the invention. One of the currently available databases for identifying protein domains and thus also peptide sequences suitable as spacer module is the "SBASE protein domain library" [31].

Crosslinkers as Spacer Modules

Spacer modules also in the form of crosslinkers can be introduced into the MAT molecule for the purposes of the invention. For this purpose, the individual modules of the MAT molecule are prepared and then covalently coupled to one another by chemical reactions with crosslinkers. Numerous crosslinkers are commercially available for this purpose. For example, Pierce (Pierce Biotechnology, Inc., Rockford, Ill., USA) supplies numerous different crosslinkers. It is possible at present to select for example from Pierce between crosslinkers which react with amino groups, sulfhydrol groups, sugar structures, carboxyl groups, hydroxyl groups or non-selectively with the modules which are to be combined to give a MAT molecule. Also currently available, e.g. from Pierce Biotechnology Inc. for preparing MAT molecules are crosslinkers which can be separated again by particular chemical reactions, e.g. by thiols, bases, periodate, hydroxylamine, by the action of light or by nonspecific reactions. It is additionally possible by targeted selection of crosslinkers to specifically fix the distance between the individual modules of the MAT molecule. For example, Pierce currently supply crosslinkers which introduce a distance of 1.4 Angström (N-succinimidyl iodoacetate) to 34.7 Angström (bis(beta-(4-azidosalicylamido)ethyl) disulfide), depending on which crosslinker is used. A further possible variation in the use of crosslinkers for coupling various modules to give MAT molecules for the purposes of the present invention is the possibility of using the crosslinker sulfo-SBED from Pierce Biotechnology Inc. Sulfo-SBED couples on the one hand two modules by covalent reaction and additionally comprises a biotin group on the introduced spacer molecule. It is then possible to attach a further module of the MAT molecule by noncovalent linkages to this biotin group. For this purpose, the module to be introduced can be coupled for example to avidin or streptavidin. The streptavidin-coupled module produced in this way can then be coupled via the biotin group present in the crosslinker to the other modules. It is possible in principle to use all currently known crosslinkers and crosslinkers which will become known in future for linking modules to give a MAT molecule for the purposes of the invention.

Further Spacer Modules

Spacer modules for the purposes of the invention may consist for example of L isomers or of D isomers of amino acids, of unusual amino acids, of amino acids with postranslational modifications, of nucleic acids, of PNAs (peptide nucleic acids), of lipids, of sugar structures, or other natural or synthetic polymers such as, for example, substituted or unsubstituted hydrocarbons, polyacetate, polyethylene glycol, cyclodextrin, polymethacrylate, gelatin, oligourea etc., or of other substances or of combinations of the substances mentioned or others. It is possible in principle to use all currently known substances suitable for joining modules together to give a MAT molecule, and molecules which will become known in future and have corresponding properties, as spacer module for linking modules to give a MAT molecule for the purposes of the invention.

Spacer Modules which are Linked Together by Noncovalent Interactions

There is a large number of examples of this class of spacer molecules in the literature. Examples of such combinations of molecules which are linked together via noncovalent interactions and which are commercially available are: biotin/streptavidin or avidin or Strep-tagII (IBA GmbH, Göttingen, Germany) or PinPoint™ tag (Stratagene, La Jolla, Calif., USA), glutathione S-transferase/glutathione and protein A/constant portion of antibodies (FC part) (Pharmacia Amersham Biosciences, Uppsala, Sweden, Sigma, St. Louis, Mo., USA), maltose-binding protein (MBP)/amylose (New England Biolabs, Beverly, Mass., USA), histidine tag/Ni chelate (Qiagen, Hilden, Germany, BD Bioscience Clontech, Palo Alto, Calif., USA, Invitrogen, Breda, the Netherlands, Novagen Inc., Madison, Wis., USA, Roche Applied Science, Rotkreutz, Switzerland), chitin-binding tag/chitin (New England Biolabs, Beverly, Mass., USA), calmodulin-binding protein/calmodulin (Stratagene, La Jolla, Calif., USA). There is also in addition a number of further molecule combinations such as, for example, receptor/ligand combinations, antibody/antigen combinations, lectin/sugar structure combinations, etc. Numerous currently known protein-protein interactions are to be found in databases and can be used as spacer modules for the purposes of the invention [28]. All combinations which are currently known and will become known in future of molecules able to enter into noncovalent linkages with one another can in principle be used as spacer module for the purposes of the invention. A further method for introducing spacer modules into MAT molecules is the use of bispecific molecules which combine two different binding sites in one molecule. Examples of such molecules would be biotin-labeled lectins (Pierce Biotechnology, Inc., Rockford, Ill., USA) which are able to link together for example a streptavidin-labeled module and a further module which has a sugar structure which is bound by the lectin. A further example of a possibility for coupling in this way are bispecific antibodies which recognize two different epitopes, etc.

A further variant for introducing spacer modules into MAT molecules is as follows: firstly, at least two modules are coupled to one another via a noncovalently linking spacer module, and then the complex is treated with chemical crosslinkers which introduce covalent bonds between modules which are in spatial proximity. This has the advantage that, in the first step, particular modules are coupled to one another in a targeted and defined manner and then the noncovalent coupling is converted into a more stable covalent coupling. If the modules are treated directly with crosslinkers which produce covalent bonds, the manner in which the modules are coupled to one another is usually random and not specific.

Structure of the MAT Molecules

Any desired arrangement of the individual modules of the MAT molecule is possible in general. Each module may be present one or more times in the MAT molecule. The minimum requirement is the need for the presence of at least one translocation module, at least one targeting module and at least one antigen module. Additional modules such as tag modules, spacer modules, etc. may optionally be present but need not be present. All modules may be present one or more times in the MAT molecule. If modules are present more than once, they may be present in the form of identical copies, or different versions of a module may be present in each case in a single copy or in more than one copy. It is also possible for entirely different modules of the same class of modules, e.g. a His tag module and a biotin tag module, to be present in a MAT molecule. Both modules undertake functionally the same task (tag module) in the MAT molecule, but need have nothing in common in terms of their molecular structure.

Two or more identical copies of an antigen module in a MAT molecule may serve for example to bring about an enhanced immune response to the relevant antigen. Two or more different antigen modules may for example be combined in one MAT molecule in order to modulate simultaneously the immune reaction to two or more different antigens. Two or more different translocation modules be used in a MAT molecule. For example, a Tat sequence and a VP22 sequence can serve to make translocation more efficient since the translocation of the MAT molecule then takes place efficiently in a broader spectrum of different cell types or tissue types. It is also possible for example to use two or more tag modules in a MAT molecule, e.g. a His tag and a FLAG tag, in which case for example the His tag is used to isolate the MAT molecule and for example the FLAG tag serves to detect the MAT molecule. It is possible to use two or more different targeting modules in a MAT molecule, e.g. a sequence from the invariant chain of the MHC II molecule and as further targeting module a mannose 6-phosphate group, of which for example the invariant chain acts as targeting module into the MIICs, and the mannose 6-phosphate group brings about a targeting into the lysosome, it thus being possible overall to increase the efficiency of antigen presentation or the number of different epitopes of the antigen presented by the antigen-presenting cells.

The position of the individual modules within the MAT molecule can also be varied as desired as long as at least one translocation module, at least one targeting module and at least one antigen module is present. It is also possible for all or some of the modules of the MAT molecule for example to be present not in the form of a linear sequential arrangement of modules but as circular or as branched module structure or else in the form of dendrimers, or as a combination of linear and/or branched and/or circular and/or dendrimeric molecule portions. Circular module structures of the MAT molecule can be generated for example by reacting two cysteine residues with one another or by reacting one cysteine residue with a thiol ester group within a chain of modules which originally had a linear structure. There are commercial suppliers of expression vectors which supply specific vectors which make it possible to prepare circular fusion proteins by these mechanisms, such as, for example, the IMPACT™-TWIN system from New England Biolabs, Beverly, Mass., USA. Branched modules might be prepared for example by synthesizing peptides in which, starting from poly L-lysine, a new lysine residue is attached to both free amino groups of each of the subsequent lysine residues. It is possible in this way to create a peptide structure with virtually any extent of branching. It is then possible for example for translocation modules and/or targeting modules subsequently to be synthesized onto the branched peptide basic structure [32]. Further modules can also be coupled onto a linear, circular or branched peptide basic structure by protein ligation [33, 34]. It is additionally possible to introduce for example biotin groups into the peptide basic structure during the peptide synthesis, and modules can then be attached to these biotin groups via, for example, streptavidin, the Strep tag system or via the PinPoint™ system (respectively IBA GmbH, Göttingen, Germany and Promega Biosciences Inc., San Louis Obispo, Calif., USA) onto the peptide basic structure. Modules attached in this way are then coupled via noncovalent linkages to the peptide basic structure.

FIG. 1 shows by way of example some examples of possible structures for MAT molecules in terms of their composition from various modules and in terms of the arrangement of the modules within the MAT molecule.

Preferred embodiments of the MAT molecules according to the present invention are molecules comprising as a translocation module the HIV-tat sequence, preferably the amino acids 47 to 57 of the HIV-tat sequence. In addition, preferred embodiments of the intracellular targeting module are the human invariant chain peptide, more preferably, the complete amino acid sequence of the human invariant chain protein. Further, the antigen module is preferably an amino acid sequence coding for an allergen or a fragment thereof. In a more preferred embodiment, the antigen module is an allergen selected from the group of Fel d 1 (cat dander allergen), Bet v 2 (birch pollen allergen), and PLA2 (phospholipase A2 allergen from bee venom). In an even more preferred embodiment, the antigen module comprises the coding amino acid sequence of the Fel d 1 antigen which consist of two chains, chain 1 and chain 2 forming a heterodimer. The order of said two chains may be chain 1 followed by chain 2 or chain 2 followed by chain 1 when starting from the N-terminus. Of course it is possible that more than one sequence of each chain is present in the antigen module. The chains are directly covalently linked to one another or are separated by spacer molecules. Further, the different modules of a MAT molecule may be directly linked to one another, e.g. covalently linked, or may be linked via spacer molecules to one another. Preferably short spacer molecules are present between the translocation module and the targeting module, between the targeting module and the antigen module, and, optionally, between a tag module, if present, and the translocation module. Preferably the spacer modules are short peptides comprising 2 to 10 amino acids, preferably a Glycin-Serine peptide or a Threonin-Serine-Glycine-Serine peptide. If a tag module is present in the MAT molecule, said tag module is preferably a HIS-tag.

Particularly preferred embodiments are shown in FIG. 10 and Seq-ID No. 21 to 36. The embodiment outlined in FIG. 10 contains the HIV-tat amino acids 47 to 57, a spacer, the complete amino acid sequence of the human invariant chain, a spacer, chain 2 of Fel d 1, chain 1 of Fel d 1 when starting from the N-terminus. Optionally, a HIS-tag may be present N-terminal of the HIV-tat sequence separated by a spacer sequence.

Structure of the Modules of MAT Molecules

Peptides, proteins, amino acids, unusual amino acids, pos-translational modifications etc.

The terms peptide and protein are used side by side as equivalent in the present patent application. A peptide or a protein means for the purposes of the invention a covalent connection of at least two amino acids via a peptide linkage. The term "amino acid" and the term "amino acid residue" are used as equivalent in the present application, i.e. the meaning of the two terms is identical. The terms amino acid/amino acid residue and peptide/protein are used in the present application in the form of the widest possible definition.

Amino acids mean for the purposes of the invention besides the 20 amino acids determined by the genetic code also the amino acids which can be encoded by stop codons, such as, for example, seleno-cysteine or pyrro-lysine. Additionally included are all known amino acid and peptide derivatives such as, for example, glycosylated, phosphorylated, sulfated amino acids/peptides, and L-isomeric and D-isomeric amino acids, and amino acid and peptide derivatives which will be known in future. Amino acid and peptide derivatives can arise, or be prepared specifically, by post-translational modifications, by chemical modifications, by enzymatic modifications or on the basis of other mechanisms. The resulting peptides may comprise modifications which may occur in all regions of the peptide molecule. For example, modifications may occur in the peptide backbone, in the amino acid side chains, at N-terminal ends of the peptide or at C-terminal ends of the peptide. The modifications may be present in single amino acids, in a plurality of amino acids or in all amino acids, and it is possible for no, one or a plurality of types of modifications to be present in any combinations in a peptide. The peptides may be branched, the peptides may be in cyclic form, and any combinations of branched and cyclic peptides are possible. Branched and/or cyclic peptides may arise through natural biological processes or be prepared by synthesis. Examples of unusual amino acids which may be mentioned by way of example are, inter alia: alpha-aminobutyric acid, beta-aminobutyric acid, beta-aminoisobutyric acid, beta-alanine, gamma-aminobutyric acid, alpha-aminoadipic acid, 4-aminobenzoic acid, aminoethylcysteine, alpha-aminopenicillanic acid, allysine, 4-carboxyglutamic acid, cystathionine, carboxyglutamic acid, carboxyamidomethylcysteine, carboxymethylcysteine, cysteic acid, citroline, dehydroalanine, diaminobutyric acid, dehydroamino-2-butyric acid, ethionine, glycine-proline dipeptide, 4-hydroxyproline, hydroxylysine, hydroxyproline, homoserine, homocysteine, histamine, isovaline, lysinoalanine, lanthionine, norvaline, norleucine, ornithine, 2-piperidinecarboxylic acid, pyroglutamic acid, pyrrolysine, proline-hydroxyproline dipeptide, sarcosine, 4-selenocysteine, syndesines, thioproline, etc. All said amino acids can be present in the form of their L isomers or in the form of their D isomers as long as this is permitted by their structure. In general, all currently known amino acids and amino acid derivatives which occur naturally or are formed or can be prepared enzymatically or chemically or in another way, and modifications of amino acids to become known in future, are included in the term "amino acid" and may be constituent of MAT molecules for the purposes of the invention.

Examples of postranslational or chemical modifications which may be present in one or more modules of the MAT molecule for the purposes of the invention and which are mentioned are, inter alia, modifications of the amino acid sequences by the following structures: binding of free cysteine to a cysteine in the peptide sequence, formation of disulfide linkages between two cysteine residues, methylations, acetylations, acylations, farnesylations, formylations, geranylgeranylations, biotinylations, stearoylations, palmitylations, lipoylations, C-mannosylations, myristoylations, phosphorylations, sulfatylations, N-glycosilations, O-glycosilations, amidations, deamidations, demethylations, cysteinylations, carboxylations, hydroxylations, iodinations, oxidations, pegylations, prenylations, ADP-ribosylations, 5'-adenosylations, 4'-phosphopan-theinations, glutathionylations, covalent bonding: of flavin, of heme groups (or other porphyrins), of nucleic acids or of nucleic acid derivatives, of lipids or of lipid derivatives, of phosphatidylinosistol, of glycosylphosphatidylinositol anchors (GPI anchors), of pyridoxal phosphate, of mannose 6-phosphate, modifications of cysteine to carboxyamidomethylcysteine or carboxymethylcysteine or pyridylethylcysteine, modification of lysine to lipoic acid, modification of glutamine to pyroglutamic acid, addition of amino acids onto peptides by tRNAs, ubiquitin labeling of peptides, branchings of peptides, e.g. in the form of poly-L-lysine, cyclizations of peptides, e.g. by forming disulfide linkages between 2 cystenine residues, etc., possible. Numerous further modifications of proteins which are, inter alia, also archived in databases are described in the literature [35]. In general, all currently known modifications of peptides which occur naturally or are formed or can be prepared enzymatically or chemically or in another way, and modifications of peptides which will be known in future, are included in the term "peptide" and may be constituent of MAT molecules for the purposes of the invention.

Peptidomimetics

It is additionally possible for the purposes of the invention for one or more amino acids of modules or the complete module or all modules of the MAT molecule to be replaced by structures consisting of peptidomimetics. The term peptidomimetic is used in the present application in the form of the widest possible definition. A peptidomimetic is a substance which comprises non-peptide structural elements and is able to imitate or to antagonize the biological effect of the natural parent molecule. Numerous studies dealing in detail with possibilities for using peptidomimetics as replacement for conventional peptide structures are known in the art. It is generally possible for one or more modules of the MAT molecule to be composed entirely or partly of peptidomimetics [36-38]. This may have various advantages. Translocation modules may possibly penetrate more efficiently into cells thereby, targeting modules may transport the MAT molecule more efficiently or less efficient and/or more specifically into the desired intracellular organelle, antigen modules may lead to an enhanced or reduced immune response relative to the immune response to the conventional antigen, or tag modules may have better physicochemical properties, improving their suitability for the isolation and/or detection of the MAT molecule, etc. It is additionally possible through the use of peptidomimetics in some circumstances to reduce or increase the in vivo stability of the MAT molecule, to reduce or increase its toxicity, to improve its solubility in hydrophilic or hydrophobic media, and to prolong its in vitro stability and possibly to reduce the costs for synthesizing the peptidomimetic relative to the cost for synthesizing the corresponding conventional peptide. One example of peptidomimetics are Spiegelmers® supplied by NOXXON Pharma AG, Berlin, Germany. This type of peptidomimetics has the advantage for example that they do not elicit an immune response and therefore could be employed in a worthwhile manner for example in translocation modules, targeting modules, tag modules, spacer modules, etc. of MAT molecules. Spiegelmers® would, however, not be suitable as antigen module.

Preparation and Isolation of MAT Molecules

A further embodiment of the invention is the isolation of MAT molecules using recombinant expression systems, chromatography methods and chemical synthesis protocols known to the skilled worker. The MAT molecules isolated in this way can be used inter alia for producing medicaments and diagnostic aids and for producing antibodies in experimental animals and in in vitro systems.

Preparation of MAT Molecules

Methods known to the skilled worker for preparing MAT molecules include recombinant expression of peptides. It is possible to use for expression of the peptides inter alia cell systems such as, for example, bacteria such as *Escherichia coli*, yeast cells such as *Saccharomyces cerevisiae*, insect cells such as, for example, *Spodoptera frugiperda* (Sf-9) cells, or mammalian cells such as Chinese hamster ovary (CHO) cells. These cells are obtainable from the American Tissue Culture Collection (ATCC). For recombinant expression of peptides, for example nucleic acid sequences which code for entire MAT molecules or for individual molecules of MAT molecules are introduced into an expression vector in combination with suitable regulatory nucleic acid sequences such as, for example, selection markers, promoters, etc. using methods of molecular biology. Suitable selection markers are, for example, resistances to antibiotics such as ampicillin, kanamycin, neomycin, puromycin or metabolic defects, e.g. yeast cells unable to produce alanine, leucine, tryptophan etc., or mammalian cells lacking the enzyme hypoxanthine-guanine phosphoribosyltransferase and therefore unable to survive in HAT medium (hypoxantines, aminopetrin, thymidine medium), etc. Suitable promoters are, for example, the cytomegalovirus immediate early promoter (CMV promoter), the SP1 minimal promoter or the thymidine kinase promoter (TK promoter). In the selection of the promoters it is necessary to select promoters suitable for the particular cell system. For example, the T7 or the T7/lacO promoter is suitable for bacteria while, for example, the nmt1 promoter is suitable for yeast cells. If MAT molecules or modules of MAT molecules are toxic it may be advantageous or necessary to use expression vectors which make it possible to control the expression of these molecules from outside, e.g. through the Tet-On™ and the Tet-Off™ expression system (Promega Biosciences, San Louis, Calif., USA). In this system, the activity of the promoter of the expression vectors is regulated by addition of tetracycline to the growth medium of the cells. Further examples of methods which can be used for external regulation of the expression of MAT molecules or of modules of MAT molecules is the induction of T7 polymerase by IPTG or the use of ecdysone-inducible expression systems such as, for example, the Complete Control® Inducible Mammalian Expression System (Stratagene, La Jolla, Mo., USA). On use of vectors which comprise an IRES (internal ribosome entry site) sequence it is also possible for a plurality of molecules to be prepared simultaneously through the use of only one expression vector (e.g. pLP-IRESneo vector, Promega Biosciences, San Louis; CA, USA). It is thus possible in this way for example for two or more modules of a MAT molecule which are intended to interact with one another by noncovalent linkages to be expressed in parallel with one another in appropriate stoichiometric ratios of amounts, and possibly also purified in parallel. Various companies supply commercially available expression vectors for various cell systems, e.g. Invitrogen, Qiagen, Stratagene, Clontech, Novagen, New England Biolabs, Pharmingen, Promega, Pharmacia, etc. The expression vectors isolated in this way can then be introduced into suitable cells, e.g. by electroporation, calcium phosphate coprecipitation, liposome-mediated transfection, etc., in a manner known to the skilled worker. Alternatively, it is also possible to use recombinant viruses produced by methods of molecular biology, which then in turn infect cells and bring about the expression of MAT molecules or modules of MAT molecules by the infected cells. Suitable viral expression systems are, for example, the bacculovirus system, e.g. BacculoGold (BD Bioscience Pharmingen, Palo Alto, Calif., USA), adenoviral expression systems such as, for example, ViraPort™ (Stratagene, La Jolla, Calif., USA), retroviral expression systems such as, for example, AdEasy (Stratagene, La Jolla, Calif., USA) etc.

It is also possible as alternative to transfection of expression vectors and to viral expression systems to use in vitro translation systems in which, for example, rabbit reticulocyte lysates or *E. coli* S30 extracts or wheatgerm extracts are used for the synthesis of MAT molecules or for the in vitro synthesis of modules of MAT molecules without living cells being necessary for the expression.

Cell Systems for Preparing MAT Molecules

Cell lysates or cell culture supernatants can be used as starting material for preparing MAT molecules or for preparing individual modules of MAT molecules. Cell systems may be obtained for example from bacteria such as, for example, *E. coli, bacillus*, caulobacter, pseudomonas or streptomycetes or yeasts such as, for example, *saccharomyces, pichia* or *hansenula*, or insect cells such as, for example, Sf-9, Sf-21 or High Five, or mammalian cells such as, for example, CHO cells, COS cells, 3T3 cells, BHK cells, 293 cells, etc. It is possible through the use of signal sequences which bring about the export of proteins from the interior of the cell into the extracellular space for the protein to be expressed to accumulate specifically in the cell culture medium or in the periplasmic space of, for example, bacteria. A further source of starting material for preparing MAT molecules or modules of MAT molecules may be transgenic animals, transgenic plants, transgenic fungi or transgenic microorganisms into which nucleic acids which code for MAT molecules or modules of MAT molecules have been introduced stably or transiently. The corresponding nucleic acids may in this case both be integrated directly into the genome of the particular organism and be introduced for example in the form of plasmids or in the form of other DNA or RNA molecules into the organisms. The corresponding MAT molecules or modules of MAT molecules can then be isolated for example from the milk, the eggs, from serum, from urine, from tissue etc. of the transgenic animals, from, for example, storage tubers, seeds, leaves etc. of transgenic plants, from, for example, the mycelium, the fruiting body etc. of the transgenic fungi or from cells or other organisms cultivated in vitro, or from the corresponding cell culture media. All types of organisms are generally suitable for use as expression system for preparing MAT molecules or modules of MAT molecules.

Isolation of MAT Molecules

The MAT molecules or modules of MAT molecules prepared in this way can be isolated using techniques known to the skilled worker. Numerous methods known to the skilled worker for isolating proteins can be used for this purpose, such as, for example, precipitation methods, liquid phase separation methods, chromatographic methods etc. Suitable precipitation methods include inter alia immunoprecipitation, ammonium sulfate precipitation, polyethylene glycol precipitation, ethanol precipitation, trichloroacetic acid precipitation (TCA precipitation), thermal precipitation, etc. The liquid phase separation methods include for example extraction with organic solvents such as, for example, alcohols, acetone, chloroform, acetonitrile, etc., and the chromatographic methods include for example cation exchanger chromatography, anion exchanger chromatography, isoelectric focussing, reverse phase chromatography, gel filtration, immobilized metal ion affinity chromatography (IMAC), it being possible to use various metal ions such as, for example, nickel, zinc, cobalt etc., hydroxyapatite chromatography, numerous different affinity chromatography methods such as, for example, immunoaffinity chromatography, affinity chromatography using immobilized nucleic acids, or immobilized protease inhibitors, etc. The chromatographic media used may have structures based on an agarose matrix, based on magnetic particles, in the form of membranes, in the form of hollow fibers, based on various polymers such as, for example, polystyrene etc. Chromatographic methods can generally be carried out on a wide variety of scales starting from chromatography columns with a volume of a few µl up to large chromatography columns with a volume of several hundred liters. In addition, chromatographies can be carried out under normal atmospheric pressure, under medium pressures in the range from 1 to 50 bar (e.g. the FPLC system, Pharmacia Amersham Biosciences, Uppsala, Sweden) and under very high pressures in the range up to about 400 bar and possibly even greater pressures (HPLC systems). Chromatographies can be carried out under conditions which have native and denaturing effects on the MAT molecules. Various interactions between matrix material and a MAT molecule or module of a MAT molecule to be isolated can be used in affinity chromatography. These include numerous tag molecules which have already been mentioned elsewhere in the present patent application and which interact with certain functional groups or ligands and thus allow isolation of MAT molecules or modules of MAT molecules. However, it is possible in principle to use all types of interaction such as, for example, protein-protein interactions, nucleic acid-protein interactions, nucleic acid-nucleic acid interactions, sugar-lectin interactions, sugar-protein interactions, receptor-ligand interactions, antibody-antigen interactions (e.g. anti-FLAG, anti-HA, anti-myc tag antibodies), hapten-antibody interactions, Spiegelmer interactions (NOXXON Pharma AG, Berlin, Germany) etc.

Affinity Chromatography

Methods which can be used for the affinity chromatography are in particular those based on selective binding of a tag module to a matrix. Suitable combinations of tag modules and relevant matrix for isolating a MAT molecule are, inter alia: histidine tag and nickel chelate matrix (Qiagen, Hilden, Germany), GST tag and glutathione-Sepharose (Amersham Biosciences, Uppsala, Sweden), maltose-binding protein tag and amylose matrix (New England Biolabs, Beverly, Mass., USA), biotin tag and streptavidin or avidin matrix (IBA GmbH, Göttingen, Germany), chitin-binding protein tag and chitin matrix (New England Biolabs, Beverly, Mass., USA), calmodulin-binding peptide tag and calmodulin matrix (Stratagene, La Jolla, Calif., USA), protein A or protein G or protein A/G or protein L and particular regions, recognized by the respective proteins, of antibody molecules, such as, for example, the Fc portion of antibodies (Amersham Biosciences, Uppsala, Sweden), FLAG tag, HA tag, myc tag, histidine tag, etc. and a matrix to which an antibody against the particular tag is coupled (many different companies, including Promega Biosciences Inc., San Louis Obispo, Calif., USA, Invitrogen, Breda, the Netherlands, Qiagen, Hilden, Germany) etc.

Protease Recognition Sequences

The MAT molecules or modules of MAT molecules isolated in this way can be separated where appropriate from their tag module and/or other modules. It is possible for this purpose to introduce for example a protease recognition sequence at suitable positions into the particular expression vector. Numerous suitable protease recognition sequences are known to the skilled worker, including the recognition sequences of proteases such as, for example, thrombin, factor Xa, enterokinase or the TAGZyme system (Qiagen, Hilden, Germany). The added proteases can be removed again for example through immobilized protease inhibitors such as, for example, EK-AWAY for enterokinase (Invitrogen, Breda, The Netherlands), Xa Removal Resin (Qiagen Hilden, Germany), benzamidine-Sepharose for removing thrombin, etc. A further possibility for isolating MAT molecules or modules of MAT molecules is the use of inteins, i.e. of proteases which are constituent of the MAT molecule and which then, under suitable experimental conditions, eliminate themselves proteolytically from the remainder of the MAT molecule or a module of a MAT molecule (Genease™, New England Biolabs, Beverly, Mass., USA). In general, all protease recognition sequences currently known [29, 30] and to become known in future are suitable for removing constituents of MAT molecules for the purposes of the invention. The protease recognition sequences may moreover either be naturally occurring or have been designed specifically, and may be composed entirely or partly of natural amino acids, unusual amino acids, peptidomimetics etc.

Inclusion Bodies

A further embodiment of the invention is the preparation of MAT molecules or of modules of MAT molecules in the form of incorrectly folded protein aggregates, which are also referred to as inclusion bodies. Inclusion bodies can be prepared as molecules which comprise translocation modules which make transport possible from the extracellular space through the cell membrane into the interior of the cell. This translocation leads to the originally incorrectly folded molecules becoming correctly folded and then acting inside the cell like a MAT molecule correctly folded from the outset. This procedure has the advantage that unfolded proteins can be isolated under denaturing conditions, which is often associated with less technical complexity and thus financial cost. In addition, inclusion bodies are relatively stable structures. This has advantages in some circumstances for the storage and stability of MAT molecules which are kept for later medical use. It is also possible by this method to use unfolded or incorrectly folded MAT molecules or modules of MAT molecules for the purposes of the invention. Certain translocation modules bring about both translocation from the extracellular space into the cell and the reverse transport. Transformation of an as yet incorrectly folded MAT molecule can take place directly in vivo in the individual to be treated with the MAT molecule, or the folding of the MAT molecule can be carried out in a cell system in vitro. In addition, translocation of the unfolded MAT molecule into the interior of the cell, and the subsequent translocation of the then correctly folded MAT molecule into the extracellular space, can in some circumstances be brought about by the same translocation module. A mechanism of this type has been described for some sequences suitable as translocation module for the purposes of this invention, such as, for example, the VP22 sequence [39].

Modification of MAT Molecules

MAT molecules or modules of MAT molecules can be modified enzymatically, chemically or by other methods by numerous methods known to the skilled worker. For example, peptides can be provided with phosphorus groups by using kinases, phosphorus groups can be removed using phosphatases, sugar structures can be removed using glycosidases, etc. Appropriate kinases, phosphatases and glycosidases etc., and the appropriate protocols, are obtainable from various manufacturers such as, for example, New England Biolabs, Beverly, Mass., USA. Phosphorylation of MAT molecules or of modules of MAT molecules can additionally be used to label MAT molecules or modules of MAT molecules with radioactive phosphorus, thus making them easily detectable in vitro and/or in vivo. It is also possible to modify MAT molecules or modules of MAT molecules by chemical reactions. For example, disulfide bridges can be destroyed by reduction, thioester groups can react covalently with cysteine residues, or two cysteine residues can react to give a disulfide bridge, making it possible to prepare circular or branched MAT molecules or modules of MAT molecules (e.g. IMPACT™-TWIN Protein Fusion and Purification System, New England Biolabs, Beverly, Mass., USA). It is also possible to have a specific influence on modifications of the MAT molecule or of modules of MAT molecules through the selection of the expression system. For example, no glycosylation takes place in bacteria, and insect cells synthesize only particular types of glycosylations, whereas mammalian cells produce complete glycosylations. It is also possible to use for the expression cell lines which have been modified in such a way, or have been selected in such a way, that they are able specifically to produce, or unable specifically to produce, particular postranslational modifications. These advantageous properties may be inter alia a better solubility in hydrophilic or hydrophobic solvents, a longer stability of the MAT molecule at, for example, at room temperature, at 37° C., at 4° C., at −20° C., at −70° C. or at other temperatures, a longer molecular stability of the MAT molecules if they are present alone or mixed with other solid, liquid or gaseous substances, e.g. in the form of preparations as medicament or diagnostic aid, a higher penetrability of the MAT molecules for cell membranes, for membranes of organelles, for the blood-brain barrier, for the blood-CSF barrier and for other biological membranes and barriers, etc., a higher or lower in vivo or in vitro half-life, a lower or higher toxicity, a better in vivo or in vitro detectability of the MAT molecule etc.

Protein Ligation

A further possibility for preparing MAT molecules or modules of MAT molecules is protein ligation. By this is meant for example a chemical reaction in which two ends of peptides are linked together covalently by one or more chemical reactions. One example would be the reaction of a thiol ester with a cysteine side chain (e.g. IMPACT™-TWIN Protein Fusion and Purification System, New England Biolabs, Beverly, Mass., USA). It is possible in this way to prepare for example cyclic peptides. Branched MAT molecules can be prepared for example by chemical synthesis of polylysine peptides in which two further lysine residues (one lysine on each amino group of the lysine) are attached to each lysine, and thus a branched polylysine peptide is formed. It is then possible subsequently to synthesize on each terminal lysine a peptide chain, or to attach a peptide covalently by peptide ligation. Other branched polymers can also be used as carrier structure for MAT molecules or modules of MAT molecules for the purposes of the invention. One example thereof are, for example, PEG star molecules, which can be prepared by polymerizing ethylene oxide with crosslinked divinylbenzene.

Peptidomimetics

A further possibility for preparing MAT molecules or modules of MAT molecules is chemical synthesis of peptides or peptidomimetics [40] or of combinations of peptides and peptidomimetics. The preparation of MAT molecules or of modules of MAT molecules by chemical synthesis can take place for example by the Merrifield solid-phase synthesis protocol using automatic synthesizers and synthetic chemicals which are obtainable from various manufacturers. An example of a company which supplies syntheses of peptidomimetics is The Peptide Laboratory™, Benicia, Calif., USA. Numerous synthons for conventional peptides and for peptidomimetics can be purchased, for example, from Sigma-Aldrich Co, St. Louis, Mo., USA.

Composition of Medicaments and Diagnostic Aids

The peptide portions, amino acid portions, amino acid derivative portions, peptidomimetic portions etc., present in the medicaments and diagnostic aids, of the MAT molecules may also be in the form of their salts as long as these salts are pharmacologically acceptable salts. Medicaments or diagnostic aids intended for injection may be for example sterile aqueous or oily solutions which are mixed according to the prior art with suitable excipients such as, for example, dispersants, humectants and agents which stabilize suspensions. The sterile solutions for injection may be produced using pharmacologically acceptable diluents or solvents such as, for example, 1,3-butanediol. Among the acceptable solvents and buffers which can be used are, inter alia, water, Ringer's solution, isotonic sodium chloride solutions etc. In addition, sterile oils, including synthetic mono- or diglycerides, can be used. It is possible in addition to employ fatty acids such as, for example, oleic acid to prepare the solutions for injection. It is furthermore possible to use dimethylacetamide, detergents, including ionic and nonionic detergents, polyethylene glycols, etc. Mixtures of the abovementioned substances are likewise possible. It is additionally possible for medicaments also to be produced in the form of mixtures with biodegradable polymers which release the medicaments continuously. One example of such a system is, for example, the Atrigel system (Atrix Labs, Fort Collins, Colo., USA).

Preparations which can be used for rectal administrations are those consisting of mixtures consisting of MAT molecules and, where appropriate, further substances with a suitable, nonirritant ointment base or filler such as, for example, cocoa butter, synthetic mono-, di- or triglycerides, fatty acids or polyethylene glycol. It is additionally possible for colorants, preservatives and odorants to be present. These and further suitable substances are solid at room temperature and melt at body temperature, so that they release the contained substances.

It is possible to use for oral administration inter alia capsules, tablets, pills, powders, granules etc. In such dosage forms, the active substances of the medicaments and diagnostic aids are often combined with adjuvants suitable for the particular dosage form. The substances may be processed with lactose, sucrose, starch powder, cellulose esters, alkanoic acids, cellulose alkyl esters, stearic acid, magnesium stearate, magnesium oxide, sodium or calcium salts of phosphorous or sulfurous acid, gelatin, gum arabic, sodium alginate, polyvinylpyrrolidones, polyvinyl alcohol etc. to, for example, tablets, capsules etc. Such capsules, tablets etc. may additionally comprise substances which enable or promote controlled release of the active substances such as, for example, hydroxypropylmethylcellulose. It is additionally possible for buffer substances such as sodium citrate, magnesium or calcium carbonates or bicarbonates, etc. to be present. Further constituents may be colorants, fragrances, flavorings, preservatives and sweeteners. Tablets, pills, capsules etc. may additionally receive coatings which, on the one hand, make them resistant to gastric acid but, on the other hand, have the effect that they dissolve in the alkaline environment of the intestine.

It is also possible to use liquid, pharmaceutically acceptable emulsions, solutions, syrups and gel-like preparations for oral administration. These preparations may comprise solvents used in medicine, such as, for example, water, ethanol, etc. These preparations may also comprise adjuvants, humectants, emulsifiers and suspending agents, etc., and sweeteners, flavorings, colorants, preservatives and odorants.

Liquid preparations intended for injection purposes can be produced from sterile powders or from granules by dissolving in aqueous or nonaqueous solvents. The powders and granules on which these solutions are based may comprise one or more of the substances mentioned for medicaments which can be administered orally. Suitable solvents are, inter alia, water, polyethylene glycol, polypropylene glycol, ethanol, corn oil, cottonseed oil, coconut oil, benzyl alcohol, sodium chloride solutions or various other buffers. Further possible ingredients are colorants, preservatives etc.

The amount of MAT molecules and further ingredients of the medicaments depends on the dosage form, dosage frequency, the chosen administration route, the age, sex, weight and the state of health of the patient, etc. An additional factor to be taken into account is whether the treatment is carried out for diagnosis, therapy or for prophylaxis, and whether the aim of the treatment is to enhance the immune reaction or to depress the immune reaction. Numerous works on the formulation and dosage of medicaments are known to the skilled worker [41, 42].

Obtaining Antibodies by Use of MAT Molecules

A further embodiment of the invention is the obtaining of monoclonal, oligoclonal or polyclonal antibodies by use of MAT molecules. The antibodies are obtained in the usual manner familiar to the skilled worker. Such antibodies obtained by use of MAT molecules enable the specific immunological detection of the antigens present in the antigen modules of the MAT molecules. The antibodies recognize exactly the antigens present in the antigen modules, and/or antigens which are similar to the antigens in the antigen modules, and/or one or more epitopes of the antigens in the antigen modules, and/or one or more neo-epitopes of the antigens in the antigen modules, and/or the corresponding complete antigens, although only parts of these antigens were present in the antigen modules, etc. Polyclonal antibodies can be produced by immunizations of suitable experimental animals such as, for example, mice, rats, guinea pigs, hamsters, rabbits, goats, sheep, cats, dogs, monkeys, cattle, horses, donkeys, chickens or other experimental animals. Monoclonal antibodies can be produced for example by immunizations of experimental animals such as, for example, mice or rats and subsequent application of hybridoma techniques which are known to the skilled worker. Monoclonal antibodies may also be produced by recombinant experimental approaches in which, for example, nucleic acids which code for the particular monoclonal antibody are isolated from hybridoma cell lines which have been produced by immunization of experimental animals with MAT molecules. These nucleic acids can be used in recombinant expression systems or by use of in vitro translation systems to produce the corresponding antibodies. The antibodies produced in this way can be produced and used in the form of complete antibody molecules, as protein consisting of the complete antibody or parts of the antibody fused to other amino acid sequences, as F(ab) fragments, as F(ab)2 fragments, as single-chain variable fragments (ScFv) or as other antibody fragments.

Administration Routes for Medicaments and Diagnostic Aids of the Invention

The medicaments and diagnostic aids of the invention can be administered to the patient or to an experimental animal to be immunized by various routes. These methods include inter alia oral and sublingual dosage, e.g. in the form of tablets, coated tablets, capsules, granules, liquid solutions, powders to be dissolved in liquids, etc., possible compositions for example of coated tablets, tablets, granules and capsules where appropriate being such that, without being exposed to the acidic environment of the stomach, the medicaments reach the intestine, and the ingredients of the medicaments are released only there. It is additionally possible to administer the medicaments by topical application to the skin or to mucous membranes for example in the form of ointments, sprays, dusting powders, tinctures etc. or inhaled as aerosol via the mucous membranes, e.g. of the respiratory tract. Rectal administration in the form of suppositories, enemas, etc. is also possible. On transdermal administration of the medicaments it is also possible to use aids such as, for example, patches or iontoporesis appliances (transdermal administration with the assistance of electric currents). Other forms which are suitable for the purposes of the invention for administering the medicaments and diagnostic aids are injections, infusions or administration via medicinal pump systems. Injections, infusions and administration via pump systems may take place inter alia intravenously, intramuscularly, subcutaneously, intracutaneously, intraarticularly, intrasternally, intrathecally, intraperitoneally, etc. Direct injection of the MAT molecules into lymph nodes such as, for example, inguinal lymph nodes is also possible. A further possible type of administration of MAT molecules is the in vitro treatment of patients' cells, in particular cells specialized for antigen presentation, such as, for example, dendritic cells, B lymphocytes, macrophages, further macrophage-like cells, etc. As a further example, cells of experimental animals, or cell lines can be treated with MAT molecules. The treated cells can then subsequently be administered to the patient or the experimental animal. The cells can be administered as living cells, as inactivated cells no longer capable of division, or as killed cells to the patient or to the experimental animal. Inactivated or killed cells can be obtained for example by treatment with suitable substances or by irradiation, e.g. with radioactive or ultraviolet radiation. A further possibility for administering the medicaments, in particular the MAT molecules of the invention, is stable or transient transfection of animal, human or plant cells with a vector which leads to expression of a MAT molecule. The cells modified in this way can where appropriate be entrapped in a matrix which firstly fixes them locally and secondly protects them from the patient's or the experimental animal's immune system but which, on the other hand, allows the MAT molecules released from the cells to escape into the patient's or experimental animal's body. In some circumstances it is also possible for transfected cells to be administered directly to the patient or experimental animal, in which case the cells are treated where appropriate in such a way that they are no longer able to divide, e.g. by irradiation or by treatment with suitable chemicals. The medicaments may additionally be administered packaged in liposomes or other vesicles such as, for example, exosomes, or deoxosomes, or the medicaments can be administered in the form of mixtures with biodegradable polymers which release the medicaments continuously. One example of such a system is, for example, the Atrigel system (Atrix Labs, Fort Collins, Colo., USA). It is additionally possible for further substances to be administered by the same or by one or more other administration routes simultaneously or sequentially to the dosage of the medicament or diagnostic aid of the invention. These further substances may inter alia improve, via their immunostimulating properties, the effect of the medicaments or diagnostic aids of the invention. Such substances given simultaneously or sequentially may be inter alia adjuvants, mineral oil, Freund's adjuvant, immunostimulating proteins or mediators such as, for example, cytokines, other vaccines etc. It is additionally worthwhile where appropriate for immunosuppressant substances to be administered simultaneously or sequentially in order for example to reduce or suppress unwanted local immune reactions, while systemic immune reactions are retained. Simultaneous or sequential administration of immunosuppressant substances may, however, also conversely be used to prevent systemic immune reactions, while at the same time the local immune reaction are retained.

A preferred embodiment of the invention is the intranodal injection of MAT-molecules. Intranodal injections are injections directly into lymph nodes, which bring the antigen directly to a region within the body, which region is responsible to a large extend for antigen processing and presentation, thereby further improving the effectiveness of the MAT-molecules (WO 02/028429 A3). Preferred lymph nodes for intranodal injections of MAT molecules are the major lymph nodes located in the regions of the groin, the underarm and the neck, most preferably the lymph nodes located in the region of the groin.

Possibilities for Examining the Efficacy of MAT Molecules

Various in vitro and in vivo experiments can be carried out to examine the efficacy of MAT molecules in relation to modulation of the immune response of an individual.

Suitable as in vitro model are, for example, peripheral blood mononuclear cells (PBMCs), e.g. obtained from the blood of patients suffering from allergic disorders. The advantage of such cells is that the exact antigen against which the particular patient has an allergic response is often known. This knowledge makes it possible for example to simulate a desensitization of the patient in vitro, before clinical studies are carried out on the patient or in experimental animals. For this purpose, for example, the PBMCs from allergic people can be treated with the particular antigen against which the allergic person reacts, or with a MAT molecule which comprises the particular allergen in the antigen module. Thus, the immunological reaction of the primary patient's cells to various dosage forms (complete MAT molecule, molecules with/without translocation module, molecules with/without targeting module etc.) of the allergen can be investigated. Suitable measurement parameters are inter alia cytokine determinations in the cell culture supernatant. Various types of T cells are involved in the immune response to an antigen, such as, for example, T-helper cells of type 1 (Th1 cells) or of type 2 (Th2 cells) or of type 0 (Th0 cells). The type of T cells involved in each case has a great effect on whether the immune response induced against the antigen primarily consists of immunoglobulins of class E (IgE) or of immunoglobulins of class G (IgG). It is known from the literature that, in particular, IgE immune responses are responsible for allergic reactions and asthma, whereas IgG immune responses are usually associated with a tolerance to the antigen. The particular T cell type activated by the treatment of the PBMCs with an antigen can be determined for example also by determining the expression of surface antigens on the cell surface or by determining messengers such as, for example, cytokines which are released by the PBMCs. Markers of a Th1 immune response which can be determined are, for example, interferon gamma (INF-g) or interleukin-1 (IL-1) in the cell culture medium, whereas IL-4, IL-5, IL-6, IL-10 and IL-13 indicate a Th2 immune response. These cytokines can be detected by standard methods known to the skilled worker, such as, for example, ELISA determinations from, for example, the cell culture supernatants or FACS analyses of the messengers present on the surface or inside the cells of the PBMCs, or by Western blots of cell culture supernatants or cell lysates etc. Numerous other methods suitable for detecting these or other messengers are disclosed in the literature [43, 44]. Besides the messengers released by the PBMCs, it is also possible to use intracellular or membrane-associated messengers or further proteins for immunological characterization of the T cells in PBMCs. Numerous antibodies suitable for such investigations are supplied inter alia by Pharmingen, San Diego, Calif., USA, Beckmann Coulter Inc., Fullerton, Calif., USA, Santa Cruz Biotechnology Inc., Santa Cruz, Calif., USA, etc. Corresponding investigations can, however, be carried out not only with patients' primary cells but also with cells obtained from appropriately treated experimental animals, e.g. mice, rats, guinea pigs, etc. Experiments with experimental animals have the advantage that not only can the cells of these animals be studied in vitro, but that the immune system can be investigated in vivo in the context of an intact organism. It is thus also possible to investigate the effect of the dosage, composition and administration form of the MAT molecules and of corresponding controls such as, for example, molecules which consist only of an antigen or which consist only of a translocation module and an antigen module or which consist only of a targeting module and of an antigen module. It is possible to investigate inter alia whether there are differences in the nature of the immune response if MAT molecules or corresponding controls are injected subcutaneously in a conventional way or if the injection takes place for example directly into lymph nodes. It is also possible to investigate the effect of noninvasive administrations such as, for example, orally or sublingual administration of the MAT molecules and of corresponding controls. A further investigation which can be carried out in experimental animals is administration of MAT molecules or corresponding controls with and without simultaneous administration of adjuvants such as, for example, mineral oil, mycobacterial extracts or Freund's adjuvant. It is also possible to ascertain the most effective or best-tolerated time schedule for the immunizations to be carried out, and the dose and number of immunizations. Different antigen modules can moreover be tested for their efficacy. It is possible in this way to ascertain the best immunization strategy for later studies on human patients.

Besides messengers, intracellular proteins and surface proteins, also suitable in particular for characterizing the immune reaction of cells cultivated in vitro or for characterizing the immune reaction of experimental animals or of human patients in clinical studies are immunoglobulins. It is possible for example by using ELISAs to investigate and quantify whether the antibodies released owing to the administration of the allergen or antigen are of the IgE type or of the IgG type. This information would indicate the type of immune reaction involved.

Since the messengers released by the T cells also inter alia have an effect on the proliferation of cells of the immune system which are present inter alia in PBMC preparations, it is also possible to characterize the immune response by determining the proliferation of cells such as, for example, PBMCs. It is possible for this purpose to carry out for example in vitro investigations such as, for example, DNA incorporation studies with tritium-labeled thymidine to detect cell growth. Numerous other methods known to the skilled worker for determining cell proliferation can likewise be used in these investigations. Proliferation of certain cells of the immune system can also be determined in vivo by for example carrying out FACS investigations with blood samples from experimental animals or human patients taking part in studies. It is possible by selecting suitable antibodies to quantify for example different subpopulations of cell types present in the blood. The effect of a treatment with MAT molecules or corresponding controls can be investigated in this way.

For evaluation of MAT molecules in clinical studies exposure test to determine the patient's response to allergens can be used. Examples for such exposure tests known in the art are skin prick tests, conjunctival provocation tests, rhinomanometry, antigen capture tests, pulmonary function test or metacholin tests. These exposure tests can be done in comparison between patients treated with conventional commercial allergen preparations such as cat dander extracts, patients treated with recombinant or native proteins such as Fel d 1 and patients treated with recombinant MAT molecules such as for example MAT molecules with the complete Fel d 1, or MAT molecules with fragments of Fel d 1. Similar comparisons can be done with other antigens such as Bet v 1, Api g 1, Der p 1 or PLA2. The patient groups tested for example can be patients with a single allergy to the specific allergen tested, control patients with a single allergy to another allergen different to the tested allergen and control patients without any allergy. It is also possible to include groups of patients having allergies towards multiple allergens of which one allergen is the allergen to be tested, or of which no allergen is the allergen to be tested (=control group). It is also possible to include groups of patients, which patients were treated with conventional anti-allergy therapies in the past without success towards the allergen to be tested in the clinical study. The clinical study can be done in different groups of the population regarding age (adolescent versus adult), sex (male versus female), ethnic groups (African Americans, Asian Americans, Caucasian Americans, etc.). The studies are preferably done as double-blind placebo-controlled, prospective single or multiple center studies. To ensure the "double-blinded" status of the study the placebo group can be treated with substances mimicking the effects of an immunization by provoking local reactions by injection of histamine dihydrochloride as placebo. This ensures that the medical doctors conducting the blinded study can not distinguish the placebo— from the test-group. The success of the treatment can be determined by various methods known in the art, such as "quality of life" questionnaires, reduction of medication needed to treat allergy symptoms (e.g. reduction of use of anti-histamine or cortisone), reduction in drop out rate in the course of the study (the more successful the treatment, the more likely it is, that the patients freely stay in the study), etc. In addition the success of the study can be determined by measuring laboratory parameters such as Interferon gamma (IFNg), Interleukin (IL)-4, IL-5, IL-2, IL-10, etc. measuring allergen-specific antibodies such as IgG1 or IgG4 titers.

EXEMPLARY EMBODIMENTS

The following exemplary embodiments are intended to illustrate the invention by way of example but are by no means intended to restrict the range of protection of the invention.

Example 1

Cloning of Expression Vectors for MAT Molecules

All the molecular-biology methods described below were carried out in accordance with standard methods known to the skilled worker [43]. The vector pQE-30 (Qiagen, Hilden, Germany) was used for cloning a vector for expression of MAT molecules (modular antigen transport molecules).

In a first step, a nucleic acid sequence which codes for a translocation module was introduced into a bacterial expression vector. The DNA sequence which codes for the amino acids GYGRKKRRQRRR (SEQ ID NO: 44) of HIV Tat was introduced via synthetic oligonucleotides into the vector pQE-30. The oligonucleotides comprised in addition to the HIV Tat sequence at the 5' end a recognition sequence of the restriction endonuclease Bgl II and at the 3' end recognition sequences for BamH I, Spe I, Pst I and Hind III. The synthetically prepared HIV Tat sequence was subsequently cut with Bgl II and Hind III and the vector pQE-30 was cut with the restriction endonucleases Bam HI and Hind III. The Tat sequence and the vector pQE-30 were then isolated using NucleoSpin extract 2 in 1 (Macherey-Nagel, Oensingen, Switzerland), joined together using ligase, transformed into competent bacteria by electroporation, and plated out on ampizilin-containing agar plates. Some of the resulting bacterial colonies were selected, and vector DNA was isolated therefrom. The vectors obtained in this way were sequenced using standard methods to confirm the nucleic acid sequence. Bacterial clones which comprised vectors having the correct sequence were used for further studies. In a second step, a targeting module was introduced into the vector. For this purpose, mRNA from human peripheral mononuclear cells (PBMCs) was isolated using standard methods known to the skilled worker and transcribed via reverse transcriptase PCR into complementary DNA (cDNA). The nucleic acid sequence of the human invariant chain of the MHC II molecule which codes for amino acids 1 to 110 of the invariant chain of MHC II was obtained by using the cDNA obtained in this way and by using various PCR primers which introduced a Bgl II recognition sequence at the 5' end of the PCR product and introduced Spe I, Bam HI, Pst I and Hind III recognition sequences at the 3' end of the PCR products. This sequence region of the invariant chain of MHC II was introduced in accordance with the first step behind the 3' end of the Tat sequence already introduced into the pQE-30 vector. The sequence of the resulting vector was confirmed by sequencing. Standard methods of site-directed mutagenesis known to the skilled worker were used to replace cytosine by thymidine at position 292 and guanine by adenine at position 318. The two point mutations do not lead to changes in the amino acid sequence of the corresponding protein, but merely remove unwanted recognition sequences of restriction endonucleases. In a third step, finally, an antigen module was introduced into the vector. Nucleic acid sequences of various antigens were obtained by using the pQE-30 vector into which the coding sequence of the particular antigen had previously been introduced and by using PCR primers which introduce an Spe I and/or BamH I recognition sequence at the 5' end of the PCR product and a stop codon and a Pst I or a Hind III recognition sequence at the 3' end of the PCR product. Inter alia, the nucleic acid sequence which codes for amino acids 1 to 222 of the antigen Der p 1 (based on the amino acid sequence of the mature Der p 1 protein) was obtained as antigen module. This sequence region of the antigen Der p 1 was introduced in accordance with the first two steps behind the 3' end of the sequence of the invariant chain of MHC II which had already been introduced into the pQE-30 vector. The correct sequences of the resulting vectors were confirmed by sequencings. For subsequent studies, the expression vectors were isolated using QIAfilter plasmid midi kits (Qiagen, Hilden, Germany) in accordance with the manufacturer's protocol.

Example 2

Obtaining the Coding Sequences of the Antigens Bet v 1, Asp f 1, Asp f 6 and Der p 1

The coding sequences of the various antigens in the antigen modules were isolated by various methods known to the skilled worker [43]. The Bet v 1 sequence was obtained via synthetic oligonucleotides, the Asp f1 and Asp f6 sequences were obtained in earlier studies and isolated from the vectors used in these studies [45, 46] and subsequently introduced into the pQE-30 vector, and the Der p 1 sequence was isolated by reverse transcriptase PCR using mRNA obtained from house dust mites (*Dermatophagoides pteronyssinus*).

Example 3

Expression and Isolation of MAT Molecules in Bacteria

The expression and isolation of MAT molecules was carried out in accordance with the manufacturer's information (Qiagen, Hilden, Germany). In detail, a preculture of *E. coli* M15 bacteria transfected with the particular expression vector (pQE-30-MAT molecule) was set up in 20 ml of medium (2×YT medium, 100 μg/ml ampicillin, 25 μg/ml kanamycin) in a bacterial shaker at 37° C. overnight. The preculture was then cultivated in 2000 ml of medium (2×YT medium, 100 μg/ml ampicillin, 25 μg/ml kanamycin) at 37° C. in a bacterial shaker until it reached an optical density of 0.6 at a wavelength of 600 nm. After addition of IPTG in a final concentration of 1 mM and a renewed growth phase of from 4 to 15 h, the bacteria were separated from the culture medium by centrifugation at 2000 g for 20 minutes, and the bacterial pellet was stored at −20° C. Cell lysates were produced by thawing the bacterial pellet, resuspending in 8 M urea solution (5 ml of urea solution per gram wet weight of the bacterial pellets), cautiously stirring for 1 to 2 h and subsequently centrifuging at 48 000 g for 30 min. The clear supernatant was used for preparative nickel chelate chromatography of the MAT molecules. The MAT molecules were isolated by using 49 or 18 ml columns (Bio-Rad Laboratories Inc., Hercules, Calif., USA), packed with 5 to 10 ml of Ni-NTA Superflow matrix (Qiagen) and a chromatography system from Bio-Rad (Econo pump and UV monitor). The chromatography column is initially washed with 5 column volumes of buffer A (100 mM NaH2PO4, 10 mM Tris/HCl, 6 M guanidine HCl, pH adjusted to 8.0 with HCl) and then the bacterial lysate is loaded onto the column at a flow rate of 1.4 ml/min. Then 5 to 10 column volumes each of buffer A and buffer B (buffer B: 100 mM NaH2PO4, mM Tris/HCl, 8 M urea, pH 8.0) are pumped onto the column at a flow rate of 1.4 ml/min, and the absorption of the flow-through at a wavelength of 280 nm (A280) is observed. As soon as the flow-through has reached a stable A280 of less than about 0.01, the column is washed with 5 to 10 column volumes of buffer C (100 mM NaH2PO4, 10 mM Tris/HCl, 8 M urea, pH adjusted to 6.3 with HCl) until finally a stable A280 of less than about 0.01 is reached. The MAT molecule is then eluted with buffer E (100 mM NaH2PO4, 10 mM Tris/HCl, 8 M urea, pH adjusted to 4.5 with HCl) and collected.

Example 4

Detection of MAT Molecules with SDS Polyacrylamide Gels, Coomassie Staining and with Anti-his Western Blotting SDS Polyacrylamide Gel Electrophoresis Buffer, NuPAGE® gels and an Xcell SureLock™ electrophoresis chamber from Invitrogen (Invitrogen Life Technologies, Breda, The Netherlands) were used for the electrophoresis in accordance with the manufacturer's information. 5 or 10 μg of the isolated MAT molecules per lane underwent electrophoretic separation in 12% NuPAGE® Novex bis-Tris gels (Invitrogen) at a constant voltage of 200 V using 1× concentrated NuPAGE® SDS sample buffer under reducing conditions over the course of 35 to 50 min. The running buffer used was MES or MOPS buffer (MES buffer: 50 mM MES (morpholinoethanesulfonic acid), 50 mM Tris/HCl, 3.5 mM SDS, 1 mM EDTA, pH 7.3, MOPS buffer: 50 mM MOPS (3-(N-morpholino)propanesulfonic acid), 50 mM Tris/HCl, 3.5 mM SDS, 1 mM EDTA, pH 7.7).

Coomassie Blue Staining:

The gels are stained by incubating them in staining solution (200 ml of methanol, 50 ml of acetic acid, 250 ml of water, 0.5 g of Coomassie blue R-250) for 1 h and then destaining with multiple changes of the destaining solution (200 ml of methanol, 50 ml of acetic acid, 250 ml of water) until the background of the gels is clear. The Xcell II® blot module (Invitrogen) is used for electrotransfer of the proteins from the NuPAGE® gel onto a blotting membrane in accordance with the manufacturer's information. The blotting apparatus is set up in accordance with the manufacturer's information using 1× NuPAGE® transfer buffer with 10 or 20% methanol. PVDF membranes were used as blotting membrane, and the electrotransfer took place at a constant voltage of 30 V for 1 h.

Immunological Detection of MAT Molecules:

Immunological detection of MAT molecules took place using anti-His antibodies in accordance with the manufacturer's instructions (anti-RGS(His)4 antibodies, Qiagen, Hilden, Germany). All the experimental steps take place at room temperature. The PVDF membrane is initially dried and then incubated directly, without previous blocking of free protein-binding sites, with the anti-His antibody (Qiagen) in a dilution of from 1:1000 to 1:2000 in TBS (50 mM Tris/HCl, 150 mM NaCl, pH 7.5) with 3% BSA (bovine serum albumin) for 1 h. The membrane is then washed 3× with TBS, 0.05% Tween 20, 0.2% Triton X-100 for 10 min each time and subsequently washed once with TBS without further additions. The secondary antibody used is anti-mouse Ig-HRP conjugate (Amersham, Buckinghamshire, England) in a dilution of from 1:10 000 to 1:20 000 in TBS with 10% milk powder, incubating for 1 h. Finally, the blot is washed 4× with TBS, 0.05% Tween 20, 0.2% Triton X-100 for 10 min each time. The conjugate is detected using the ECL™ system (Amersham) in accordance with the manufacturer's information. The chemiluminescence signal is detected using autoradiography films, which are developed in accordance with standard protocols.

Example 5

Translocation of MAT Molecules into Cell Lines and Primary Human Cells

PBMCs (peripheral blood mononuclear cells) were obtained from fresh, heparin-treated human blood from volunteer subjects by standard methods of density gradient centrifugation known to the skilled worker using Ficoll-Paque (Pharmacia, Uppsala, Sweden). The Jurkat cell line was obtained from the ATCC (American Type Culture Collection, Manassas, Va., USA). The cells were cultivated in RPMI-1640 medium containing the following additions: 10% fetal calf serum, 200 units/ml penicillin, 200 μg/ml streptomycin, MEM vitamins, MEM nonessential amino acids, 1 mM sodium pyruvate, 2 mM L-glutamine and 0.001% 2-mercaptoethanol. To determine the translocation, the cells were resuspended in a concentration of 1×10Exp6/ml RPMI medium with all additions. The cells were incubated in accordance with the respective information in the explanations for the figures with concentrations of from 0.01 to 5 mM of the recombinant molecules or MAT molecules over a period of 5 min at 4, 22 or 37° C. The cells were then centrifuged, and the cell pellet was incubated in 40 μl of lysis buffer (8 M urea, 100 mM sodium phosphate, 10 mM Tris/HCl, 100 mM ammonium chloride) at room temperature for 5 min. Insoluble cell constituents were removed by centrifugation (15 000 g, 15 min) and the clear lysate was further investigated by Western blotting in accordance with example 4. An anti-His antibody was used to detect the proteins.

Example 6

Stimulation of Peripheral Blood Mononuclear Cells (PBMC) from Patients with Allergies The methods described below for stimulating PBMCs and for determining the proliferation of the stimulated PBMCs are described in the literature [44]. PBMCs were isolated from fresh, heparin-treated blood from volunteer subjects by density gradient centrifugation using Ficoll-Paque (Pharmacia, Uppsala, Sweden). The volunteer subjects were patients with an allergy against an allergen known for the individual patient. The patients were informed in accordance with Swiss laws about the experiments carried out on their blood samples and gave their consent to take part in this study. After the PBMCs had been obtained they were taken up in RPMI medium with the additions according to example 5, and in each case from 0.01 to 100 nM of the recombinant antigen against which the particular patient shows an allergic reaction were added. In each case, the unmodified antigen and the antigen coupled to a translocation module and a targeting module (MAT molecule) were investigated. Experimental approaches in which no targeting module but only a translocation module and the antigen module were coupled were also carried out in some experiments (FIG. 7A). The controls also used in some experiments were only the translocation module or a construct consisting of translocation module and targeting module but without antigen module. After an incubation time of 5 days, 10 μCi/ml tritium-labeled thymidine was added to the medium. The thymidine incorporation of the PBMCs was ascertained as a measure of the efficiency of antigen presentation and the proliferation, associated therewith, of the treated cells. For this purpose, the radioactive cell culture medium was removed after 8 to 10 h, the cells were washed and the amount of incorporated radioactive thymidine was determined by measuring the radioactivity. A 1205 Betaplate liquid scintillation counter from Wallac ADL AG, Hünenberg, Switzerland, was used for this. As control, cells not stimulated with antigen were likewise incubated with tritium-labeled thymidine and then analyzed in the same way. The result obtained is a measurement of the incorporation of radioactive thymidine as a measure of the proliferation and thus as a measure of the efficiency of antigen presentation. A higher measured thymidine incorporation means a more efficient antigen presentation. Since antigen concentrations of from 0.01 nM to 100 nM were investigated in each experiment, it is additionally possible to determine the antigen concentration at which maximum antigen presentation takes place. A lower concentration means that the antigen is more effective as modulator of an immune response. As a further control, cells were treated with 0.5 μg/ml each of an anti-CD3 and of an anti-CD28 antibody, which treatment represents a very strong proliferation stimulus. It was thus possible to determine the maximum possible thymidine incorporation due to the proliferation of PBMCs for each experiment.

Example 7

MAT molecule-stimulated cytokine release PBMCs were isolated from the blood of allergic people as described in example 5 and diluted 10Exp6/ml of medium. 100 µl portions of this cell suspension were seeded in 96-well plates and treated with from 0.01 to 1000 nM of the isolated antigens for 5 days. The cell culture medium was not replaced in this time. After centrifugation of the 96-well plates, the supernatants were removed and stored at −20° C. until the cytokines were analyzed. The PBMCs were treated in each case with the antigen against which the patient from whom the PBMCs were isolated shows an allergic reaction. The following cytokines were investigated in the supernatants obtained in this way: interferon gamma (INFg), interleukin-10 (IL-10) and interleukin-5 (IL-5). FIGS. 8A and 8B show results obtained with PBMCs from patients showing an allergic reaction to Bet v 1. The INFg, IL-10 and IL-5 immunoassays (ELISAs=enzyme-linked immunosorbent assays) were carried out by methods known to the skilled worker using DuoSet® ELISA Development Systems from R & D Systems Inc., Minneapolis, USA.

In parallel with the obtaining of the supernatants for the cytokine determinations, stimulation experiments were also carried out with PBMCs from the same donors in accordance with example 6. The results of these cell proliferation assays are likewise depicted in FIGS. 8A and 8B.

Example 8

In Vivo Effect of Unmodified Antigens and Antigens Present in the Antigen Module of MAT Molecules Immunization of Mice In order to test the efficacy of MAT molecules, CBA/2 mice were immunized 3× at an interval of 2 weeks each time with recombinant MAT molecules together with aluminum hydroxide as adjuvant in a manner known to the skilled worker. The recombinant MAT molecules were produced as described in example 3. 3 different routes were used for the immunization. A series of experiments was carried out in each case with subcutaneous, intraperitoneal and intranodal injection of the antigens or of the controls. In the case of intranodal injection, the tissue was exposed surgically so that direct injection was possible. The MAT molecule used was a protein consisting of the HIV Tat sequence as translocation module, the human invariant chain as targeting module and the PLA2 (phospholipase A2 from bee venom) peptide as antigen module (designation: trans-target-PLA2). PLA2 (designation: PLA2) was used as control, and 0.9% strength saline solution (designation: control) was used as further control. The intranodal immunization took place with 0.1 µg, the subcutaneous and intraperitoneal immunization took place with 10 µg of MAT molecule or corresponding amounts of control protein or control buffer together with aluminum hydroxide as adjuvant. 3 animals were immunized in each experimental group, so that in each case 9 animals were used per experiment. 3 series of experiments were carried out, and a different immunization route (subcutaneous, intraperitoneal, intranodal) was tested in each series of experiments. Blood was taken from the tail vein of each experimental animal before the first immunization and subsequently after 2, 4 and 6 weeks. The blood coagulated at room temperature, and then the serum was obtained after centrifugation and stored at −20° C. until analyzed. The sera produced in this way were used to determine the PLA2-specific IgG and IgE titers.

Determination of the PLA2-Specific IgG2a Titers in Mouse Sera

For determination of the PLA2-specific IgG2a titer, microtiter plates (96 cavities) were coated with 100 µl/cavity of a solution of 5 µg/ml PLA2 (Sigma-Aldrich, Buchs DG, Switzerland) in carbonate buffer at 4° C. overnight. After washing 2× with phosphate-buffered sodium chloride solution (PBS), 0.05% Tween, free protein-binding sites were blocked by incubation with blocking buffer (PBS, 2.5% skim milk powder), 200 µl/cavity, at room temperature for 1 to 2 h. Washing 2× was repeated, and then serial 1:2 dilution series in blocking buffer (50 µl/cavity) of the serum samples to be tested (1:2 to 1:64 dilutions) were incubated at room temperature for 3 h or at 4° C. overnight. Incubations without serum or with serum from untreated animals were carried out as negative controls. This was followed by washing 5× and incubating with a 1:500 dilution in blocking buffer of a biotin-labeled anti-mouse IgG2a (PharMingen GmbH, Hamburg, Germany) at room temperature (100 µl/cavity) for 2 h, and again washing 5×. Finally, 100 µl/cavity of a horseradish peroxidase diluted 1:1000 in blocking buffer were incubated at room temperature for 1 h and then washed 6×. The color reaction was carried out with 100 µl/cavity of a solution of ABTS (2,2'-azinodi-(3-ethylbenzothiazolinesulfonic acid) in ABTS buffer in accordance with the manufacturer's information with 0.1% (v/v) of a 30% strength hydrogen peroxide solution. After about 30 minutes, the absorption at a wavelength of 405 nm (reference filter: 595 nm) was measured. The results of these tests are depicted in FIG. 9.

Determination of the PLA2-Specific IgE Titers in Mouse Sera

The PLA2 IgE ELISA is carried out in accordance with the protocol for the PLA2 IgG2a ELISA. The deviations occurring from the protocol described above are as follows: the microtiter plates are coated with 5 µg/ml of an anti-mouse IgE antibody. After the serum samples have been incubated and the plates have been washed, a 1:333 dilution of biotin-labeled PLA2 (Pierce Biotechnology Inc., Rockford, USA) is incubated. The development of color with ABTS takes about 1 h. The results of these tests are depicted in FIG. 9.

DESCRIPTION OF THE DRAWINGS

FIG. 1

Theoretical Structure of MAT Molecules

FIG. 1 shows by way of example how the individual modules of a MAT molecule of the invention may be constructed diagrammatically. Therein "Trans" stands for a translocation module, "Target" stands for a targeting module, "AG" stands for an antigen module, "Tag" stands for a tag module and a dash (-) stands for a linker module. The linker module may connect the other modules together by covalent and/or non-covalent linkages. FIG. 1 A depicts a number of examples of linear arrangements of the various modules. FIG. 1 B depicts various examples of arrangements of branched MAT molecules, with dendrimeric structures also being included, and FIG. 1 C depicts some examples of arrangements of circular MAT molecules, it being possible to combine circular arrangements with linear and/or branched arrangements. In general, all the depicted arrangements are only examples intended to illustrate the fact that a wide variety of arrangements is possible. The diagrammatically depicted MAT molecule examples are by no means to be understood as limiting the scope of protection of the present invention.

FIG. 2

Expression, Purification and Detection of Fusion Proteins

Figure 2:
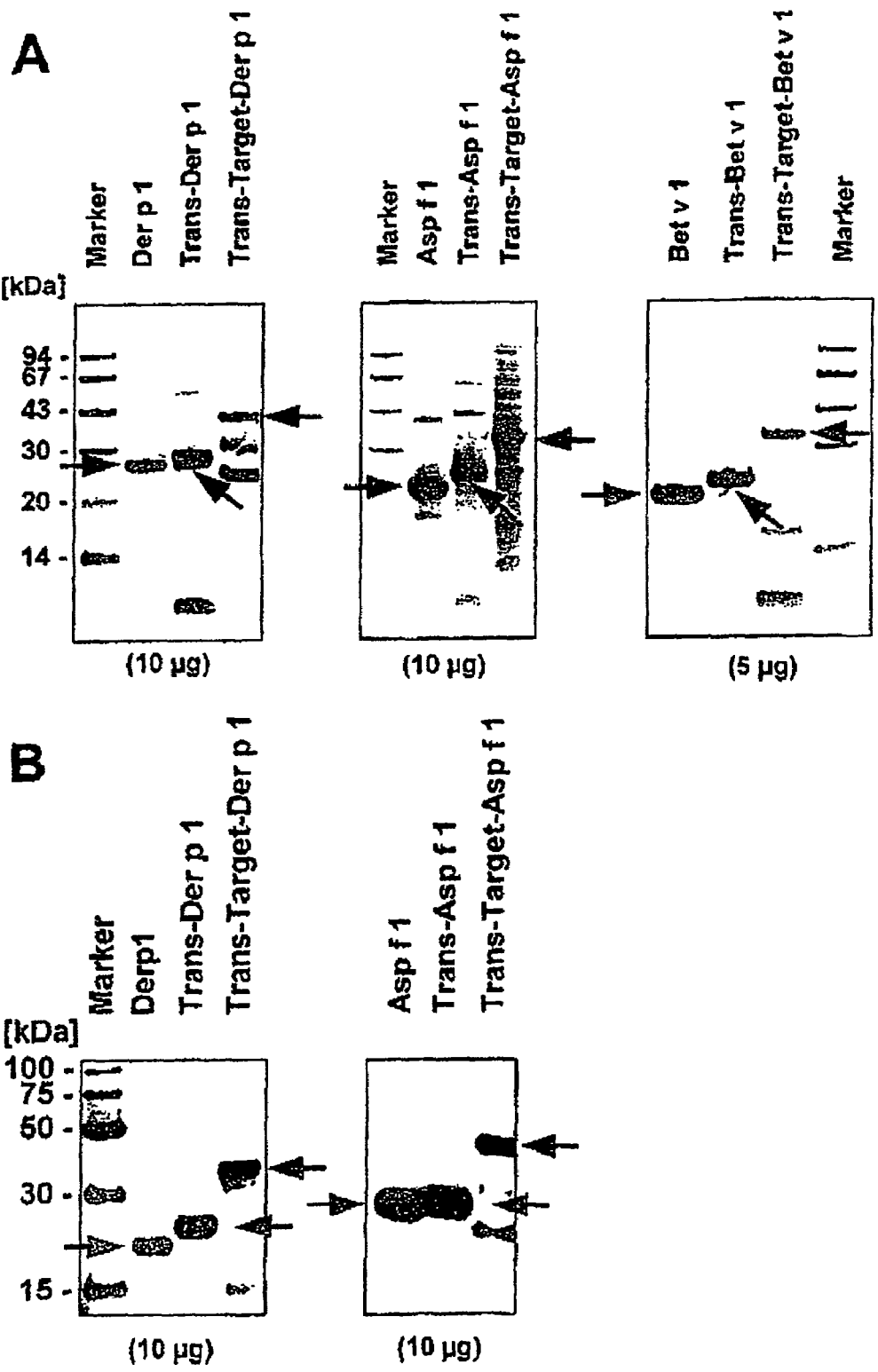

Various MAT molecules consisting of tag module (His6 tag), translocation module (Tat sequence), targeting module (human invariant chain of MHC II) and antigen module (Asp f1=*Aspergillus fumigatus* antigen 1) were expressed in *E. coli* and isolated under denaturing conditions using immobilized metal ion affinity chromatography. The steps were carried out in accordance with the information from the manufacturer of the expression system (Qiagen, Hilden, Germany) [47, 48]. 10 µg or 5 µg samples of the isolated proteins were fractionated by electrophoresis in SDS polyacrylamide gels and then either stained with Coomassie blue (FIG. 2 A) or analyzed in a Western blot using antibodies which recognize the tag module (FIG. 2 B). The positions of the expressed proteins are marked by arrows.

FIG. 3

Temperature-Independent Translocation of Proteins and MAT Molecules

Primary human peripheral mononuclear cells (PBMCs) were incubated with the particular proteins or MAT molecules in a concentration of 1 µM at 4, 22 or 37° C. for 5 minutes, washed, taken up in urea-containing sample buffer and lyzed. The lysates were then fractionated by electrophoresis in SDS polyacrylamide gels and electrotransferred to PVDF membranes, and the proteins or MAT molecules were detected using a specific antibody (anti-RGS(His)4 antibodies). The arrows show the position of the proteins or MAT molecules. The fusion proteins were detectable in the lysates of the cells at all temperatures, indicating successful translocation to the interior of the cells.

FIG. 4

Translocation of MAT Molecules in Cell Lines and Primary Cells

Figure 3:
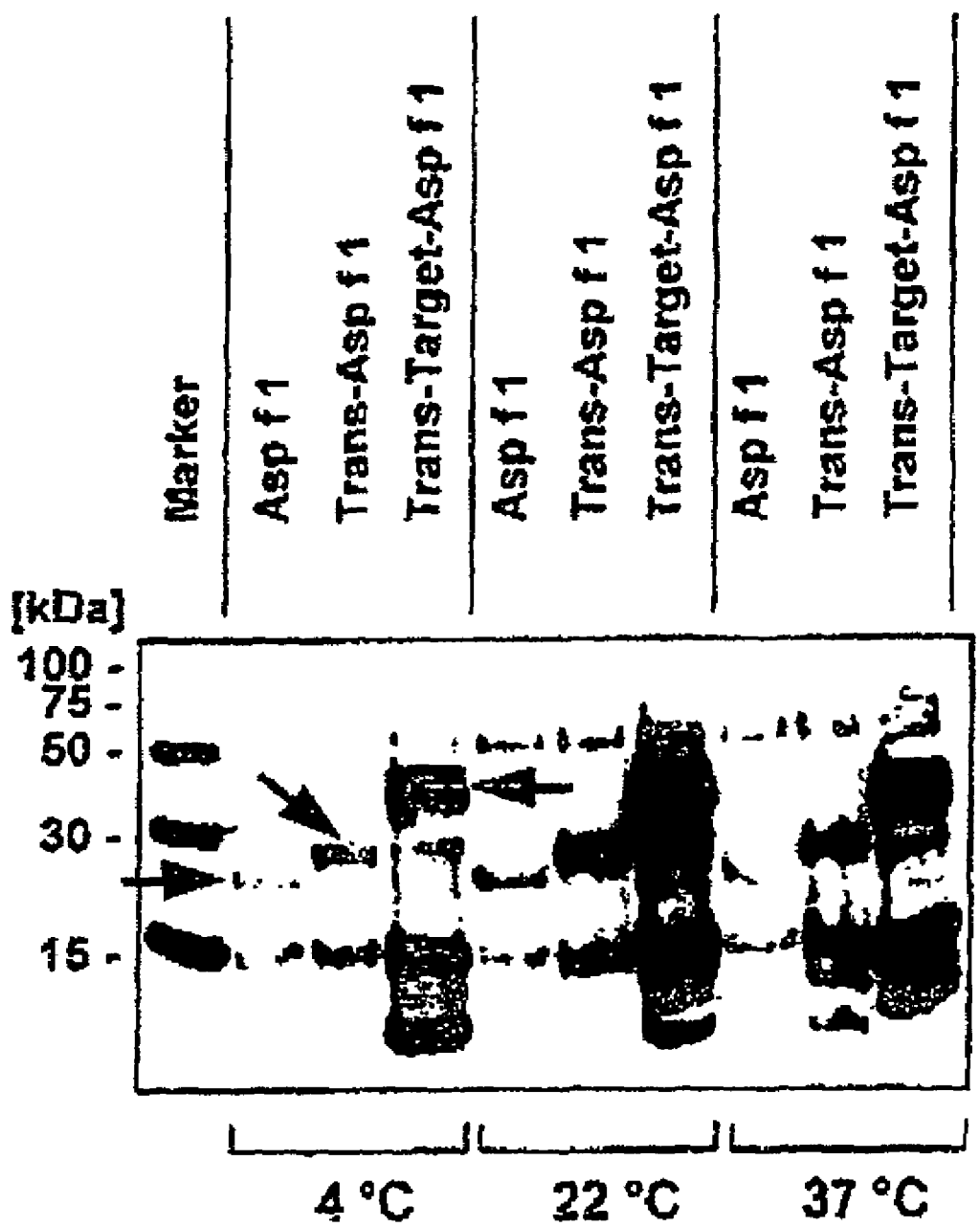
Figure 4A:
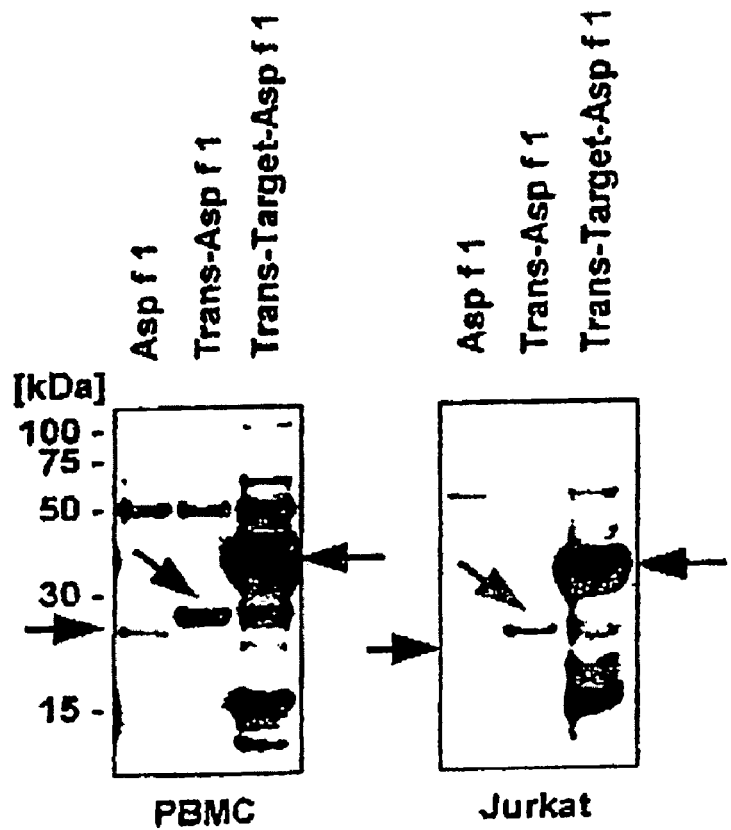
Figure 4B:
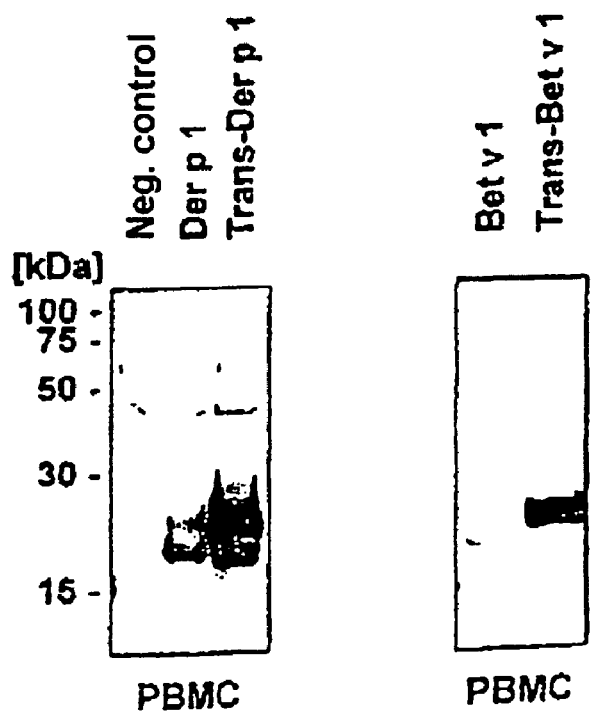
Figure 5A:
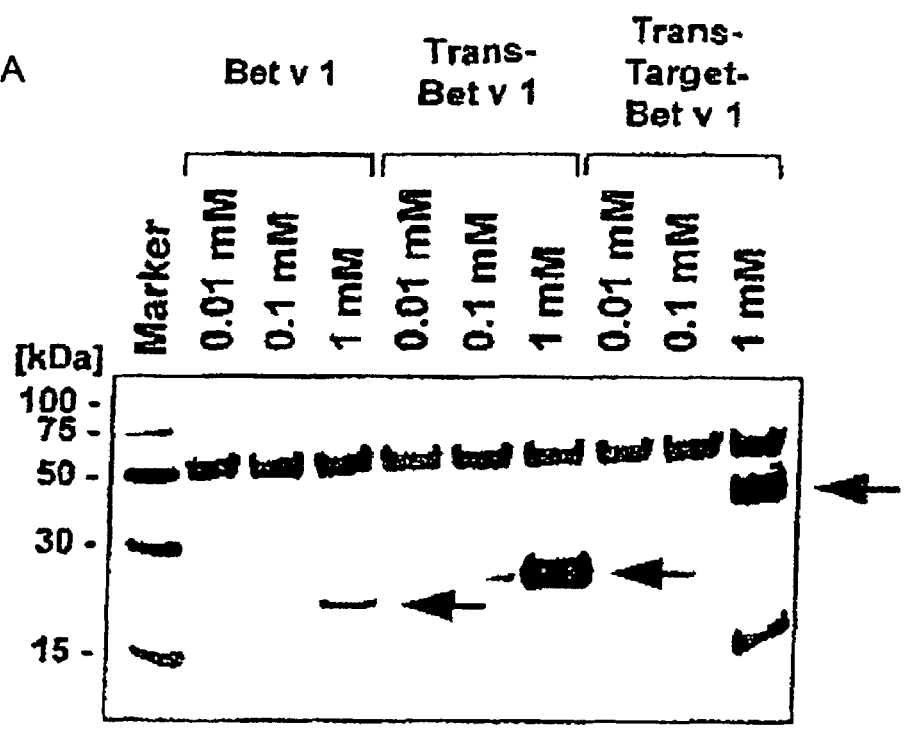
Figure 5B:
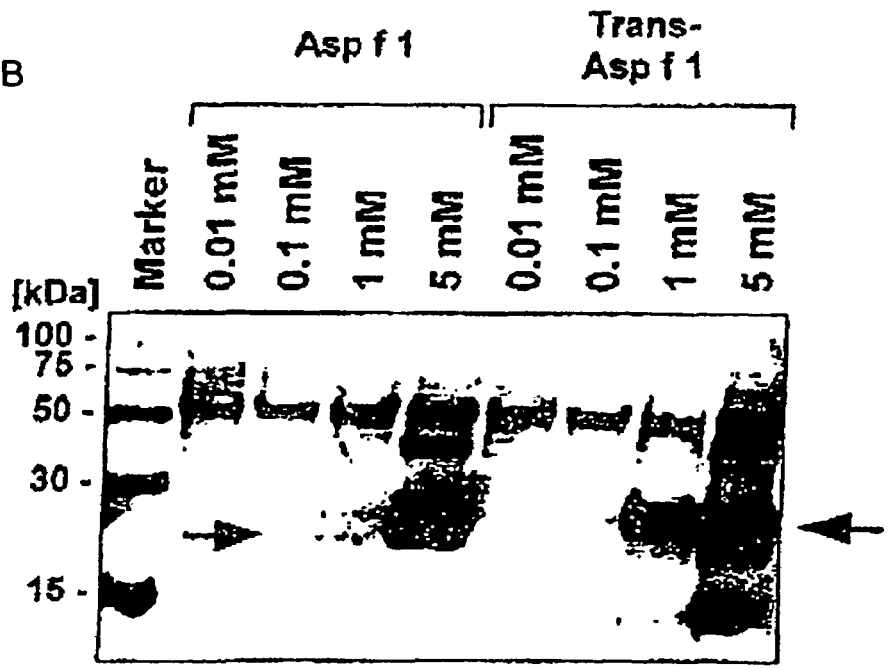
Figure 6:
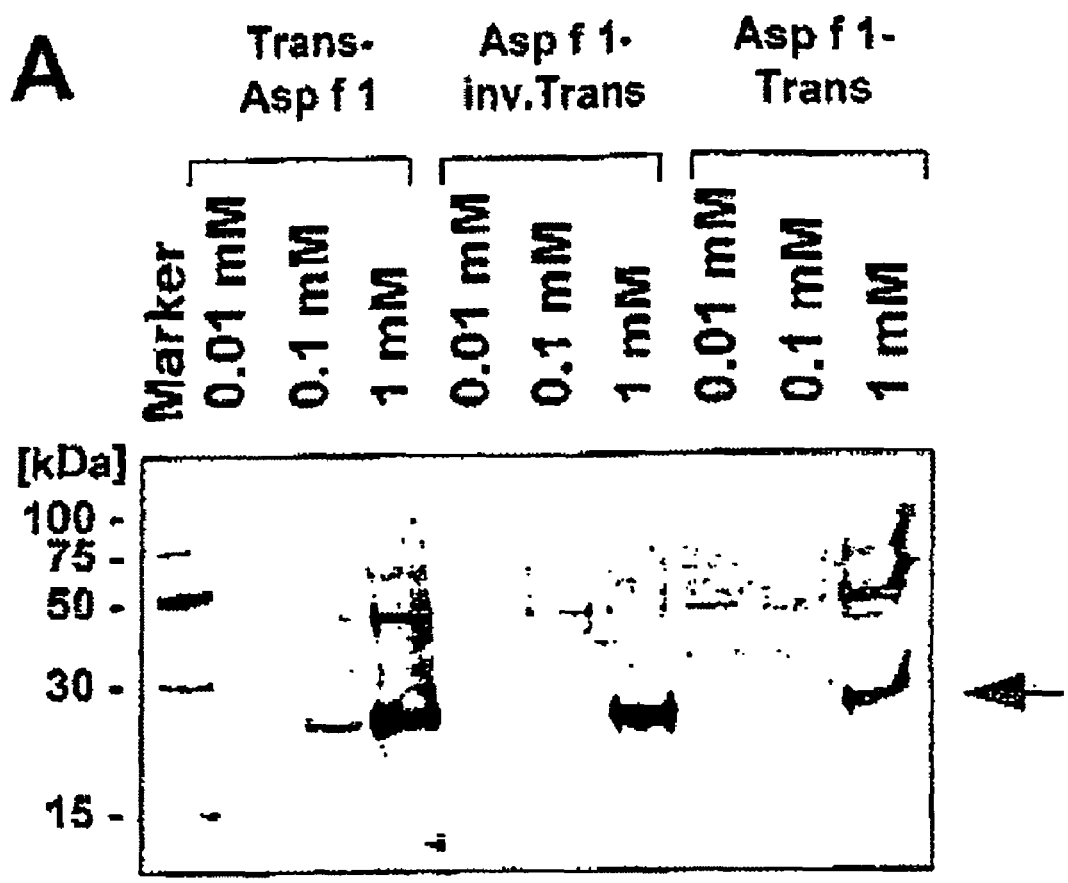
Figure 6:
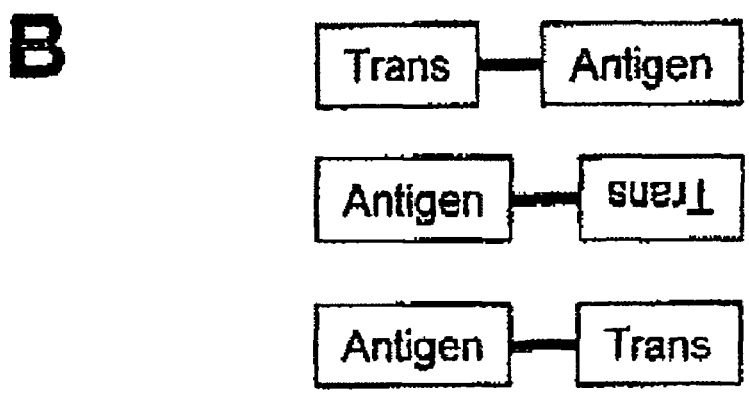
Figure 7G:
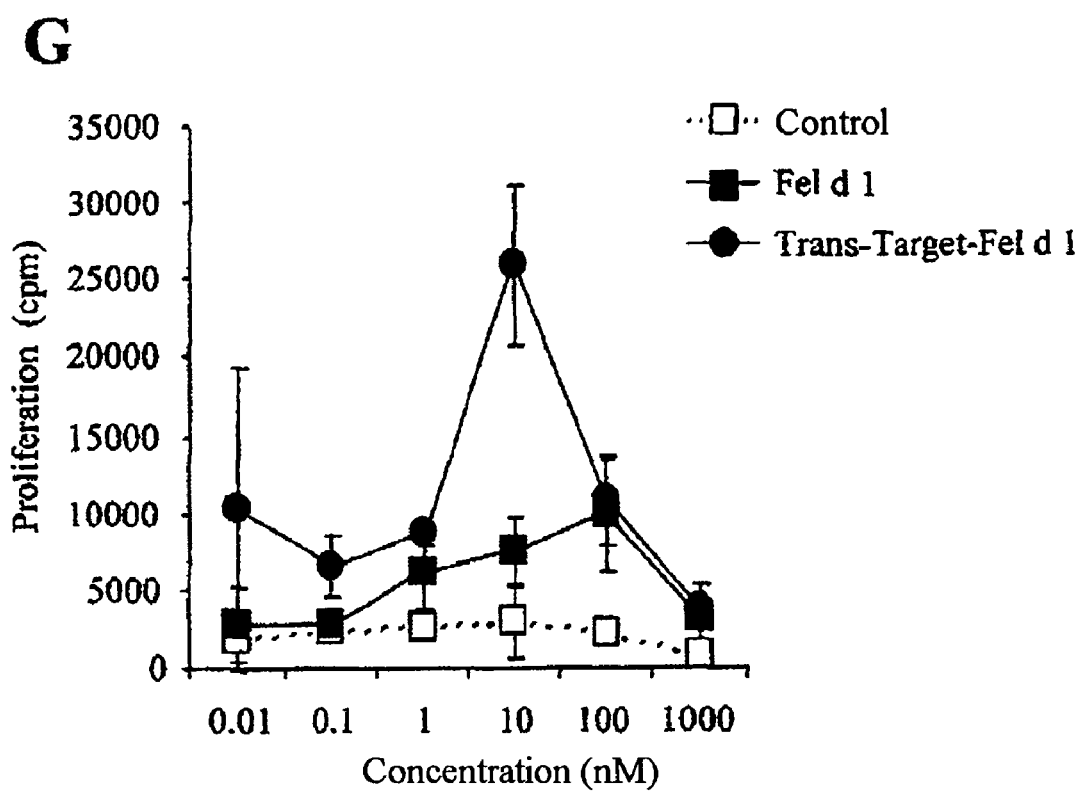
Figure 7H:
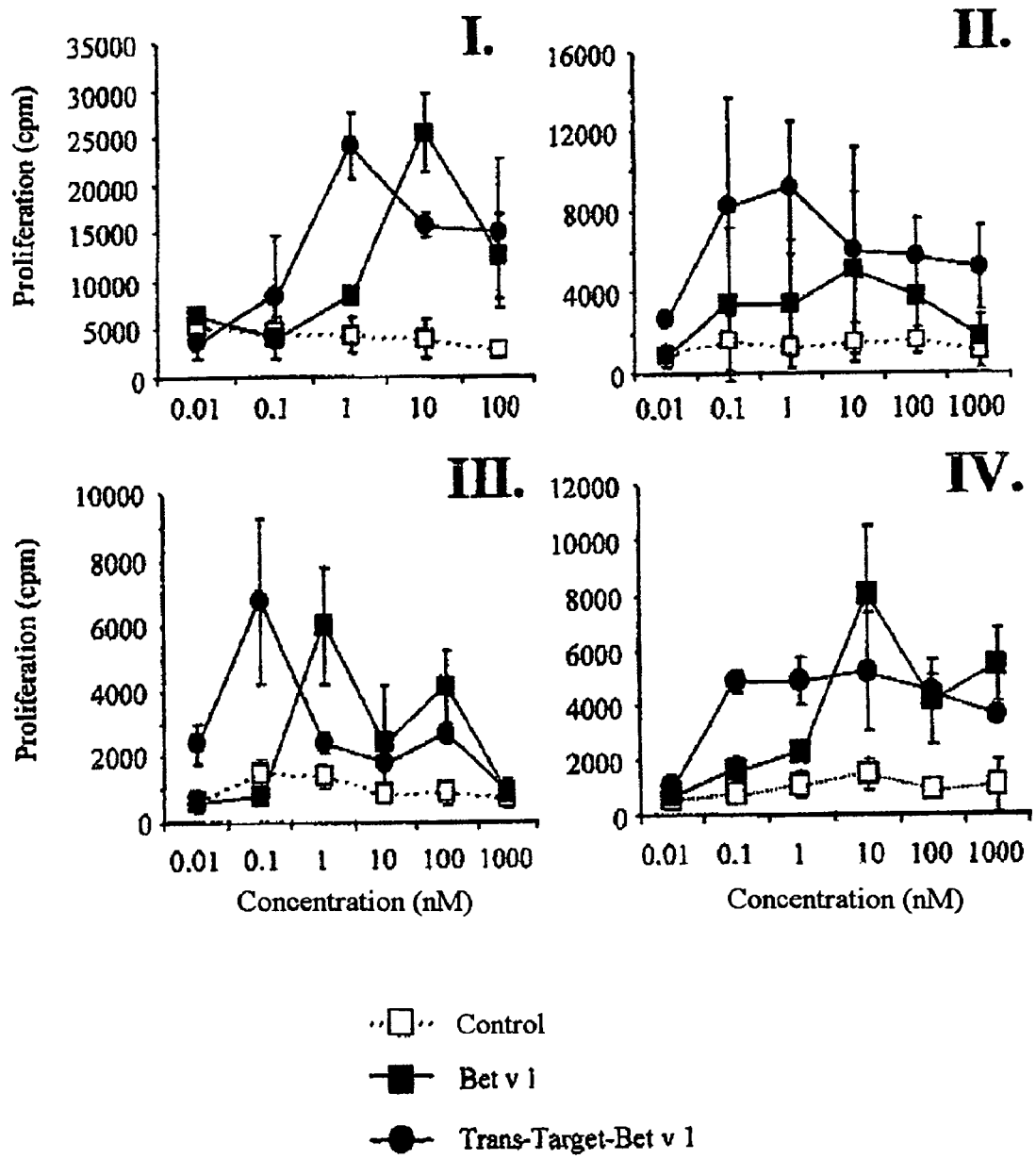
Figure 8A:
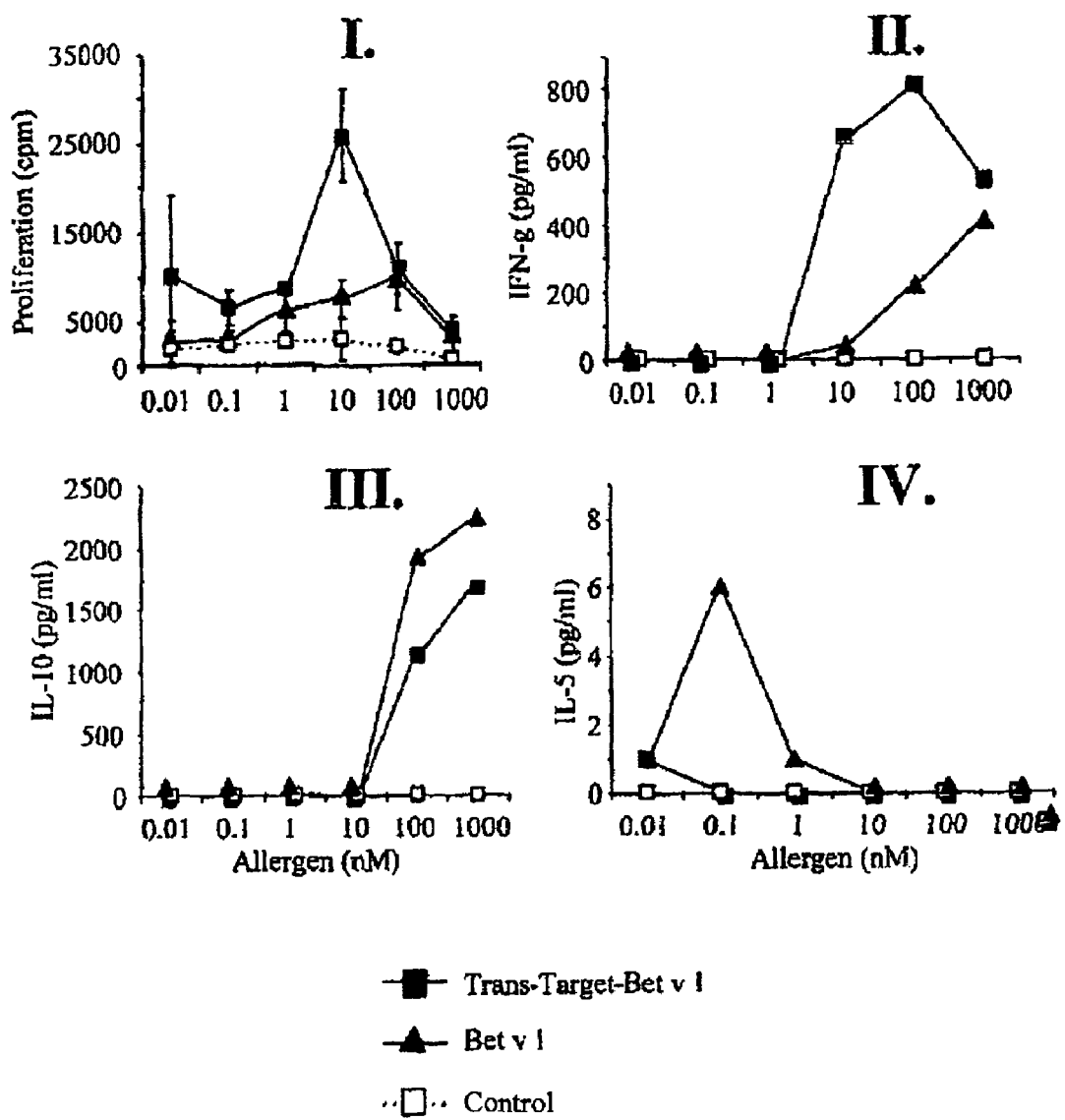

The result depicted in FIG. 4 was carried out with virtually the same methods as the experiment in FIG. 3, but with two deviations: FIG. 4 A shows that translocation of the MAT molecules was successful both in primary human cells (PBMCs) and in human tumor cell lines (Jurkat cells). The arrows show the position on the Western blot at which the protein or the MAT molecule was detected. FIGS. 4 A and 4 B additionally show that various antigen modules (Asp f 1=*Aspergillus fumigatus* allergen, Der p 1=house dust mite allergen, Bet v 1=birch pollen allergen) can enter primary human PBMC cells by translocation.

FIG. 5

Dose Kinetics of the Translocation of MAT Molecules

The result depicted in FIG. 5 was obtained with virtually the same methods as the experiment in FIG. 3, but in this case three or four different concentrations of proteins or MAT molecules were used (0.01 mM, 0.1 mM, 1 mM and 5 mM). It was possible to show a clear dose dependency for the translocation reaction. Larger amounts of the particular molecule were detected in the interior of the cells as the concentration of added MAT molecules increased. The positions of the respective molecules are marked with arrows.

FIG. 6

Various Functional Structures of MAT Molecules

The result depicted in FIG. 6 was obtained with virtually the same methods as the experiment in FIG. 3, but in this case three different arrangements of translocation module (Tat sequence) and antigen module (Asp f 1=*Aspergillus fumigatus* allergen) were investigated. The arrow in FIG. 6 A indicates the position at which the fusion protein was detected in the Western blot. FIG. 6 B depicts the structure of the three different fusion proteins. Fusion proteins with N-terminal, inverted C-terminal and with C-terminal translocation module were investigated. All three fusion proteins were transported successfully by translocation into the interior of the cells.

FIG. 7

Antigen/MAT Molecule Mediated In Vitro Cell Proliferation of PBMCs of Allergic People FIG. 7 depicts investigations on PBMCs (peripheral blood mononuclear cells) from allergic people which were put together with a MAT molecule in vitro. The MAT molecule comprised as antigen module the particular allergen against which the allergy patient shows an allergic reaction. An antigen presentation of the antigen-presenting cells of the allergic person which is more efficient owing to addition of the MAT molecule leads to stimulation of growth of the PBMCs. The cell proliferation resulting therefrom was quantified via the incorporation of radiolabeled DNA building blocks (thymidine) (y axis). The x axis indicates the MAT molecule concentration used in the particular cell-stimulation test, or the antigen molecule concentration, in nM. On use of MAT molecules at relatively low concentrations there is a cell proliferation (=immunostimulation=increase in thymidine incorporation=increase in radioactivity) in all the patients investigated with all the antigen modules investigated (as part of the MAT molecule). As control, in each case the same PBMCs were treated only with water containing no MAT molecules or antigens (=control in the legend). In addition, the thymidine incorporation by cells treated with a strong growth stimulus (anti-CD3 and anti-CD28 antibodies, 0.5 μg/ml each) for 5 days was measured as positive control for each experiment. The growth obtained by this stimulus represents a check of the quality of the prepared PBMCs in relation to their ability to proliferate. The value resulting therefrom in the experiment in FIG. 7A was 77 864±5347 cpm, the value resulting in the experiment in FIG. 7B was 100 374±11 678 cpm and the value resulting in the experiments in FIGS. 7C and D was 112 205±5958 cpm.

FIGS. 7 A to 7 G show that with all 7 tested antigens incorporation of the antigen into the antigen module of a MAT molecule leads to the onset of proliferation of the PBMCs of the allergic person even at relatively low concentrations. The antigens tested were Der p 1 (house dust mite allergen; FIG. 7 A), Bet v 2 (birch pollen allergen, FIG. 7 B), Asp f 1 (*Aspergillus fumigatus* allergen 1, FIG. 7 C), Asp f 6 (*Aspergillus fumigatus* allergen 6, FIG. 7 D), Asp f 3 (*Aspergillus fumigatus* allergen 3, FIG. 7 E), PLA2 (phospholipase A2 allergen from bee venom, FIG. 7F) and Fel d 1 (*Felis domesticus*, FIG. 7G). FIG. 7 H shows in addition for the antigen Bet v 1, on use of MAT molecules with Bet v 1 in the antigen module with 4 different patients (I. to IV.) with allergy to Bet v 1, that a proliferation of the PBMCs of the individual patients occurs in all 4 cases at lower concentrations than on use of Bet v 1 as antigen.

FIG. 8

Antigen/MAT Molecule Mediated In Vitro Cytokine Secretion by PBMCs from Allergic People FIGS. 8A and 8B show for two independent patients showing an allergic reaction to Bet v 1 that PBMCs cultivated in vitro and stimulated with the Bet v 1 antigen (Bet v 1 alone or as module of a MAT molecule) display a defined cytokine secretion pattern. I. shows in each case the result of a cell proliferation test (as in FIG. 7), II. shows the interferon gamma (INFg) levels, III. shows the interleukin-10 (IL-10) values and IV. shows the interleukin-5 (IL-5) levels in the cell culture supernatants. With a PBMC stimulation having the desensitizing effect, the PBMC proliferation and an increase in INFg release should take place even with lower antigen doses. In addition, the IL-5 production should be lower. This cytokine secretion pattern indicates a desensitization of the immune cells of the allergic people (Th1 instead of Th2 immune response). The increase in the IL-10 concentration explains why the cell proliferation (fig. I.) falls at higher antigen doses. This cytokine secretion pattern occurs in both cases (FIG. 8A and FIG. 8B).

FIG. 9

Antigen/MAT Molecule Mediated In Vivo Immune Response in Mice

Figure 9:
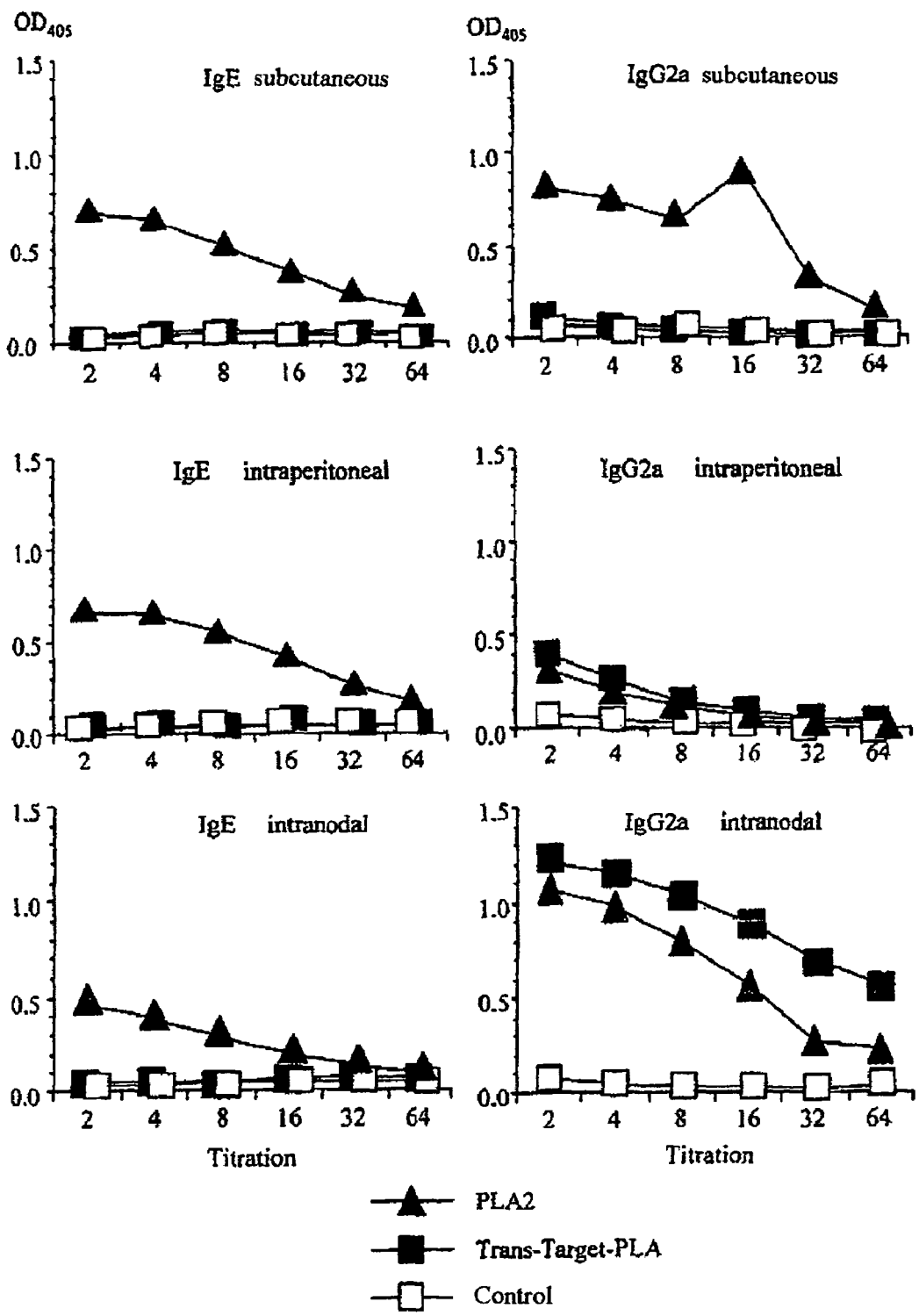

CBA/2 mice were immunized with isolated PLA2, with MAT molecules having PLA2 in the antigen module or with control buffer 3× at intervals of 2 weeks and then the PLA2-specific serum titers of IgG2a and IgE antibodies were measured. If there is desensitization, only PLA2-specific IgG, but not PLA2-specific IgE, antibodies should appear. IgE antibodies are responsible for allergic reactions. 3 different immunization routes were investigated, subcutaneous, intraperitoneal and intranodal injection of the antigens. It is found with all three immunization routes that immunization with PLA2 leads to a distinct IgE immune response (allergy) (FIG. 9, left-hand column). On immunization with a MAT molecule which comprises PLA2 as antigen module, however, there is no IgE immune response (no allergy). By contrast, both immunization with PLA2 and with MAT molecules which comprise PLA2 in the antigen module lead to a desired IgG immune response which does not induce allergic reactions.

FIG. 10

Structure of a Preferred Embodiment of the Present Invention

FIG. 10 depicts the amino acid (SEQ ID NO: 22) and nucleic acid (SEQ ID NO: 21) sequence of a preferred embodiment of the present invention. In particular, a MAT molecule is shown containing the amino acids 47 to 57 of HIV-tat representing the translocation module, a spacer, residues 1-110 of the amino acid sequence of the human invariant chain representing the targeting module, a spacer, chain 2 and chain 1 of the Fel d 1 allergen representing the antigen module (A). Below the corresponding nucleic acid sequence is shown (B).

All the examples and enumerations in the present patent application are intended in principle to explain the subject matter but not to restrict the claims. In particular, the examples of translocation modules, targeting modules, antigen modules, spacer modules and tag modules are to be understood to be only examples, but not an exhaustive list of all possible constituents of the MAT molecule. The basic idea of the invention does not consist of a particular combination of particular translocation modules, particular targeting modules and particular antigen modules. The basic idea of the present invention is, on the contrary, to use a combination of at least these three modules to give a MAT molecule for immunization. The specifically used example in each individual one of the modules is therefore immaterial for the concept of the invention, and it is consequently also possible to use other examples, including those not currently known, for the respective modules for the purposes of the invention.

If a term is not unambiguously defined in this patent, or is not known to the skilled worker in the particular art, or a term cannot be unambiguously defined from the context, then the definition mentioned for the respective term in the following standard works applies in each case. If a term is mentioned in more than one of the works cited below with different definitions, the definition which applies in each case is that mentioned in the first work mentioned in the following list. The following publications are cited for this purpose:

The Merck Manual [49]
Molecular Cloning—A Laboratory Manual [43]
Current Protocols in Immunology [44]
Current Protocols in Protein Science [50]
Current Protocols in Pharmacology [51]
Current Protocols in Cell Biology [52]

REFERENCES

1. Pieters, J. 2000. MHC class II-restricted antigen processing and presentation. *Adv. Immunol.* 76:159-208,
2. Marks, M. S., P. A. Roche, E. van Donselaar, L. Woodruff, P. J. Peters, and J. S. Bonifacino. 1995. A lysosomal targeting signal in the cytoplasmic tail of the beta chain directs HLA-DM to MHC class II compartments. *J Cell Slot* 131:351-69.
3. Karlsson, K., and S. R. Carlsson. 1998. Sorting of lysosomal membrane glycoproteins lamp-1 and lamp-2 into vesicles distinct from mannose 6-phosphate receptor/gamma-adaptin vesicles at the trans-Golgi network. *J Biol Chem.* 273:18966-73,
4. Obermüller, S., C. Kiecke, K. von Figura, and S. Honing. 2002. The tyrosine motifs of Lamp 1 and LAP determine their direct and indirect targeting to lysosomes. *J Cell Sci.* 115:185-94.
5. Chervonsky, A. V., L. Gordon, and A. J. Sant. 1994. A segment of the MHC class II beta chain plays a critical role in targeting class II molecules to the endocytic pathway, *Int Immunol.* 6:973-82.
6. Frankel, A., C. Pabo, J. G. Barsoum, S. E. Fawell, and R. B. Pepinsky. 1995. Tat-derived transport polypeptides and fusions proteins, U.S. Pat. No. 5,804,604.
7. Prochiantz, A. 2000. Messenger proteins: homeoproteins, TAT and others. *Curr Opin Cell Biol.* 12:400-6.
8. Futaki, S., T. Suzuki, W. Ohashi, T. Yagami, S. Tanaka, K, Ueda, and Y. Sugiura. 2001. Arginine-rich peptides. An abundant source of membrane-permeable peptides having potential as carriers for intracellular protein delivery. *J Biol Chem.* 276.5836-40.
9. Schwartz, J. J., and S. Zhang. 2000. Peptide-mediated cellular delivery. *Curr Opin Mol Ther.* 2.162-7.
10. Wender, P. A., D. J. Mitchell, K. Pattabiraman, E. T. Pelkey, L. Steinman, and J. B. Rothbard, 2000. The design, synthesis, and evaluation of molecules that enable or enhance cellular uptake: peptoid molecular transporters. *Proc Natl Acad Sci USA.* 97; 13003-8.
11, Dorange, F., S. El Mehdaoui, C, Pichon, P. Coursaget, and J. F. Vautherot. 2000. Marek's disease virus (MDV) homologues of herpes simplex virus type 1 UL49 (VP22) and UL48 (VP16) genes: high-level expression and characterization of MDV-1 VP22 and VP16. *J Gen Virol.* 81:2219-30.
12. Banerjee-Basu, S, D. W. Sink, and A. D. Baxevanis. 2001. The Homeodomain Resource: sequences, structures, DNA binding sites and genomic information, *Nucleic Acids Res.* 29:291-3,
13. Park, J., J. Ryu, K. A. Kim, H. J. Lee, J. H. Bahn, K. Han, E. Y. Choi, K. S. Lee, H. Y. Kwon, and S. Y. Choi, 2002.

Mutational analysis of a human immunodeficiency virus type 1 Tat protein transduction domain which is required for delivery of an exogenous protein into mammalian cells. *J Gen Virol.* 83:1173-81.

14. Rothbard, J. B., and P. A. Wender. 2001. Compositions and methods for enhancing drug delivery across biological membranes and tissues. In U.S. Pat. No. 9,779,693.

15. Florkiewicz, R. Z., and A. Baird. 1998. U.S. Pat. No. 6,083,706: Inhibitors of leaderless protein export. In U.S. Pat. No. 6,083,706. Ciblex Corporation (San Diego, Calif.).

16. Anderson, D. C., C. A. Morgan, A. P. G., E. J. Nichols, and A. R. Fritzberg. 1988. Covalently-linked complexes and methods for enhanced cytotoxicity and imaging. In European patent EP 0359347. Neorx corporation.

17. Schwarze, S. R., and S. F. Dowdy. 2000, In vivo protein transduction: intracellular delivery of biologically active proteins, compounds and DNA, *Trends Pharmacol Sci.* 21:45-8.

18. Schwarze, S. R., A. Ho, A. Vocero-Akbani, and S. F. Dowdy, 1999, In vivo protein transduction: delivery of a biologically active protein into the mouse. *Science.* 285: 1569-72, 19. Zhong, G., P. Romagnoli, and R. N. Germain, 1997. Related leucine-based cytoplasmic targeting signals in invariant chain and major histocompatibility complex class II molecules control endocytic presentation of distinct determinants in a single protein. *J Exp Med.* 185:429-38.

20. Escola, J. M., M. J. Kleijmeer, W. Stoorvogel, J. M. Griffith, O. Yoshie, and H. J. Geuze. 1998. Selective enrichment of tetraspan proteins on the internal vesicles of multivesicular endosomes and on exosomes secreted by human B-lymphocytes. *J Biol Chem.* 273:20121-7.

21. August, T. J., D. M. Pardoll, and F. G. Guarnieri. 1993. Lysosomal targeting of immunogens. In U.S. Pat. No. 5,633,234. The Johns Hopkins University, Baltimore, Md., USA.

22. Sugita, M., R. M. Jackman, E. van Donselaar, S. M. Behar, R. A. Rogers, P. J. Peters, M. B. Brenner, and S. A. Porcelli. 1996. Cytoplasmic tail-dependent localization of CD1b antigen-presenting molecules to MIICs. *Science.* 273:349-52.

23. Pieters, J., O. Bakke, and B. Dobberstein. 1993. The MHC class II-associated invariant chain contains two endosomal targeting signals within its cytoplasmic tail. *J Cell Sci.* 106:831-46.

24. Kornfeld, S., and I. Mellman. 1989. The biogenesis of lysosomes, *Annu Rev Cell Biol.* 5:483-525.

25. Schluesener, H. J. 1996. Protection against experimental nervous system autoimmune diseases by a human immunodeficiency virus-1 Tat peptide-based polyvalent vaccine. *J Neurosci Res.* 46:258-62.

26. Larsen, J. N., and H. Lowenstein. 2000. Official list of allergens, IUIS Allergen Nomenclature Subcommittee. ftp://biobase.dk/pub/who-iuse/allergen.list.

27. Larsen, J. N., and H. Lowenstein. 2001. List of isoallergens and variants, IUIS Allergen Nomenclature Subcommittee. ftp://biobase.dk/pub/who-iuis/isoallergen.list.

28, Xenarios, I., L. Salwinski, X. J. Duan, P. Higney, S. M Kim, and D. Eisenberg. 2002. DIP, the Database of Interacting Proteins; a research tool for studying cellular networks of protein interactions. *Nucleic Acids Res.* 30.303-5

29. Barrett, A. J., J. D. Rawlings, and J. F. Woessner. 1998. Handbook of Proteolytic Enzymes. *Academic Press*, ISBN 0-12-079371-7.

30. Rawlings, N. D., E. O'Brien, and A. J. Barrett. 2002. MEROPS: the protease database. *Nucleic Acids Res.* 30:343-6.

31. Vlahovicek, K., J. Murval, E. Barta, and S. Pongor. 2002. The SBASE protein domain library, release 9.0: an online resource for protein domain identification, *Nucleic Acids Res.* 30:273-5.

32. Sheldon, K., D. Liu, J. Ferguson, and J. Gariepy. 1995. Loligomers: design of de novo peptide-based intracellular vehicles. *Proc Natl Acad Sci USA.* 92: 2056-60.

33. Dawson, P. E., and S. B. Kent. 2000. Synthesis of native proteins by chemical ligation. *Annu Rev Biochem.* 69:923-60.

34. Yan, L. Z., and P. E. Dawson. 2001. Synthesis of peptides and proteins without cysteine residues by native chemical ligation combined with desulfurization. *J Am Chem Soc.* 123:526-33.

35. Garavelli, J. S., Z. Hou, N. Pattabiraman, and R. M. Stephens. 2001. The RESID Database of protein structure modifications and the NRL-3D Sequence-Structure Database, *Nucleic Acids Res.* 29: 199-201.

36. Hruby, V. J., J. M. Ahn, and S. Liao. 1997. Synthesis of oligopeptide and peptidomimetic libraries. *Curr Opin Chem Biol.* 1:114-9.

37. Senderowitz, H., and R. Rosenfeld, 2001. Design of structural combinatorial libraries that mimic biologic motifs. *J Recept Signal Transduct Res.* 21: 489-506.

38. Sulyok, G. A., C. Gibson, S. L. Goodman, G. Holzemann, M. Wiesner, and H. Kessler. 2001. Solid-phase synthesis of a nonpeptide RGD mimetic library: new selective alphav-beta3 integrin antagonists. *J Med Chem.* 44:1938-50.

39. Invitrogen. Voyager™ NES Protein Production Kits: Rapid cloning and expression of VP22 fusion proteins in *E. coli* for translocation of purified recombinant protein into the cytoplasma of mammalian cells. *Invitrogen life technologies.* Version C 060302 25-0377.

40. Goodman, M., A. Felix, L, Moroder, and C. Toniolo. 2002. Houben-Weyl: Synthesis of Peptides and Peptidomimetics. Thieme Medical and Scientific Publishers. Vol. 22.

41. Hover, J. E. 1975. Remington's Pharmaceutical Sciences. Mack Publishing Co., Easton, Pa., USA.

42, Libermann, H. A., and L. Lachman. 1980. Pharmaceutical Dosage Forms, Marcel Decker Inc., New York, N.Y., USA.

43. Sambrook, J., and D. W. Russell. 2001. Molecular Cloning—A Laboratory Manual. Cold Spring Harbor Laboratory Press, Cold Spring Harbor, N.Y., USA. 3rd Edition, 44, Coligan, J. E, A. M. Kruisbeek, D. H. Margulies, E. M. Shevach, W. Strober, and (Editors). 2002. Current Protocols in Immunology. John Wiley & Son, Inc., Hoboken, N.J., USA.

45. Moser, M., R. Crameri, G. Menz, T. Schneider, T. Dudler, C. Virchow, M. Gmachl, K. Blaser, and M. Suter. 1992. Cloning and expression of recombinant *Aspergillus fumigatus* allergen I/a (rAsp f I/a with IgE binding and type I skin test activity. *J Immunol.* 149:454-60.

46. Mayer, C., S. Hemmann, A. Faith, K. Blaser, and R. Crameri. 1897. Cloning, production, characterization and IgE cross-reactivity of different manganese superoxide dismutases in individuals sensitized to *Aspergillus fumigatus. Int Arch Allergy Immunol* 113: 213-5.

47. Qiagen. 2001. The QIA expressionist: A handbook for high-level expression and purification of 6×His-tagged proteins. Qiagen GmbH, Hilden, Germany, Fifth Edition: 1-128.

48. Qiagen. 2001. QIAexpress Detection and Assay Handbook. Qiagen GmbH, Hilden Germany. Third Edition: 1-100.
49. Beers, M. H., R. Berkow, and (Editors). 1999. The Merck Manual of Diagnosis and Therapy, Merck Research Laboratories, Whitehous Station, N.J., USA. 17th Edition.
50. Coligan, J. E., B. M. Dunn, H. L Ploegh, D. W. Speicher, P. T. Wingfield, and (Editors). 2002. Current Protocols in Protein Science. John Wiley & Son, Inc., Hoboken, N.J., USA.
51, Enna, S. J., M. Williams, J. W. Ferkany, T. Kenakin, R. D Porsolt, J. P. Sullivan, and (Editors). 2002. Current Protocols in Pharmacology. John Wiley & Son, Inc., Hoboken, N.J., USA.
52. Bonifacino, J. S., M. Dasso, J. Lippincott-Schwartz, J. B. Harford, K. M. Yamada, and (Editors). 2002. Current Protocols in Cell Biology. John Wiley & Son, Inc., Hoboken, N.J., USA.

We claim:

1. A modular antigen transport molecule (MAT molecule) comprising
    at least one translocation module which brings about transport of the MAT molecule from an extracellular space into an interior of a cell,
    at least one targeting module which brings about transport of the MAT molecule intracellularly to organelles which are involved in processing of antigens or loading of major histocompatibility (MHC) molecules with antigens, and
    at least one antigen module which determines the specificity of an immune response modulated by the MAT molecule in an individual,
    wherein the modules are coupled to one another by covalent linkages; and wherein the MAT molecule is a protein or polypeptide having the sequence set forth in a SEQ ID NO: selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36.

2. The MAT molecule of claim 1, wherein the at least one antigen module is a fel d 1 antigen module and the MAT molecule is a protein or polypeptide having the sequence set forth in a SEQ ID NO: selected from the group consisting of SEQ ID NO: 21, SEQ ID NO: 22, SEQ ID NO:23 and SEQ ID NO: 24.

3. The MAT molecule of claim 1, wherein the at least one antigen module is a bet v 1 antigen module and the MAT molecule is a protein or polypeptide having the sequence set forth in a SEQ ID NO: selected from the group consisting of SEQ ID NO: 25 and SEQ ID NO: 26.

4. The MAT molecule of claim 1, wherein the at least one antigen module is a der p 1 antigen module and the MAT molecule is a protein or polypeptide having the sequence set forth in a SEQ ID NO: selected from the group consisting of SEQ ID NO: 27 and SEQ ID NO: 28.

5. The MAT molecule of claim 1, wherein the at least one antigen module is a api g 1 antigen module and the MAT molecule is a protein or polypeptide having the sequence set forth in a SEQ ID NO: selected from the group consisting of SEQ ID NO: 29, SEQ ID NO: 30, SEQ ID NO: 31, and SEQ ID NO: 32.

6. The MAT molecule of claim 1, wherein the at least one antigen module is a pla 2 antigen module and the MAT molecule is a protein or polypeptide having the sequence set forth in a SEQ ID NO: selected from the group consisting of SEQ ID NO: 33, SEQ ID NO: 34, SEQ ID NO: 35 and SEQ ID NO: 36.

* * * * *

SEQUENCE LISTING

<160> NUMBER OF SEQ ID NOS: 44

<210> SEQ ID NO 1
<211> LENGTH: 870
<212> TYPE: DNA
<213> ORGANISM: Human immunodeficiency virus + Homo sapiens + Aspergillus fumigatus

<400> SEQUENCE: 1

```
atgagaggat cgcatcacca tcaccatcac ggatctggtt acggtcgtaa aaagcgtcgc    60
cagcgtcgcc gtggatctat ggatgaccag cacgacctta tctccaacaa tgagcaactg   120
cccatgctgg gccggcgccc tggggccccg gagagcaagt gcagccgcgg agccctgtac   180
acaggctttt ccatcctggt gactctgctc ctcgctggcc aggccaccac cgcctacttc   240
ctgtaccagc agcagggccg gctggacaaa ctgacagtca cctcccagaa cttgcagctg   300
gagaacctgc gcatgaaact tcccaagcct cccaagcctg tgagcaagat gcgcatggcc   360
accccgctgc tgatgcaggc gctgcccatg ggagccctgc cccaggggac tagtggatcc   420
gcgacctgga catgcatcaa ccaacagctg aatcccaaga caaacaaatg ggaagacaag   480
cggcttctat acagtcaagc caaagccgaa agcaactccc accacgcacc tctttccgac   540
ggcaagaccg gtagcagcta cccgcactgg ttcactaacg gctacgacgg gaatggcaag   600
ctcatcaagg gtcgcacgcc catcaaattc ggaaaagccg actgtgaccg tcccccgaag   660
cgcagccaga acggcatggg caaggatgac cactacctgc tggagttccc gacttttcca   720
gatggccacg actataagtt tgactcgaag aaacccaagg aagacccggg cccagcgagg   780
gtcatctata cttatcccaa caaggtgttt tgcggcattg tggcccatca gcgggggaat   840
cagggagact tgagactgtg ttctcattag                                    870
```

<210> SEQ ID NO 2
<211> LENGTH: 289
<212> TYPE: PRT
<213> ORGANISM: Human immunodeficiency virus + Homo sapiens + Aspergillus fumigatus

<400> SEQUENCE: 2

```
Met Arg Gly Ser His His His His His His Gly Ser Gly Tyr Gly Arg
1               5                   10                  15

Lys Lys Arg Arg Gln Arg Arg Gly Ser Met Asp Asp Gln His Asp
            20                  25                  30

Leu Ile Ser Asn Asn Glu Gln Leu Pro Met Leu Gly Arg Arg Pro Gly
        35                  40                  45

Ala Pro Glu Ser Lys Cys Ser Arg Gly Ala Leu Tyr Thr Gly Phe Ser
    50                  55                  60

Ile Leu Val Thr Leu Leu Leu Ala Gly Gln Ala Thr Thr Ala Tyr Phe
```

```
                65                  70                  75                  80
Leu Tyr Gln Gln Gln Gly Arg Leu Asp Lys Leu Thr Val Thr Ser Gln
                    85                  90                  95
Asn Leu Gln Leu Glu Asn Leu Arg Met Lys Leu Pro Lys Pro Pro Lys
            100                 105                 110
Pro Val Ser Lys Met Arg Met Ala Thr Pro Leu Leu Met Gln Ala Leu
        115                 120                 125
Pro Met Gly Ala Leu Pro Gln Gly Thr Ser Gly Ser Ala Thr Trp Thr
    130                 135                 140
Cys Ile Asn Gln Gln Leu Asn Pro Lys Thr Asn Lys Trp Glu Asp Lys
145                 150                 155                 160
Arg Leu Leu Tyr Ser Gln Ala Lys Ala Glu Ser Asn Ser His His Ala
                165                 170                 175
Pro Leu Ser Asp Gly Lys Thr Gly Ser Ser Tyr Pro His Trp Phe Thr
            180                 185                 190
Asn Gly Tyr Asp Gly Asn Gly Lys Leu Ile Lys Gly Arg Thr Pro Ile
        195                 200                 205
Lys Phe Gly Lys Ala Asp Cys Asp Arg Pro Pro Lys Arg Ser Gln Asn
    210                 215                 220
Gly Met Gly Lys Asp Asp His Tyr Leu Leu Glu Phe Pro Thr Phe Pro
225                 230                 235                 240
Asp Gly His Asp Tyr Lys Phe Asp Ser Lys Lys Pro Lys Glu Asp Pro
                245                 250                 255
Gly Pro Ala Arg Val Ile Tyr Thr Tyr Pro Asn Lys Val Phe Cys Gly
            260                 265                 270
Ile Val Ala His Gln Arg Gly Asn Gln Gly Asp Leu Arg Leu Cys Ser
        275                 280                 285
His

<210> SEQ ID NO 3
<211> LENGTH: 1044
<212> TYPE: DNA
<213> ORGANISM: Human immunodeficiency virus + Homo sapiens +
      Aspergillus fumigatus

<400> SEQUENCE: 3
atgagaggat cgcatcacca tcaccatcac ggatctggtt acggtcgtaa aaagcgtcgc        60
cagcgtcgcc gtggatctat ggatgaccag cacgacctta tctccaacaa tgagcaactg       120
cccatgctgg gccggcgccc tggggccccg gagagcaagt gcagccgcgg agccctgtac       180
acaggctttt ccatcctggt gactctgctc ctcgctggcc aggccaccac cgcctacttc       240
ctgtaccagc agcagggccg gctggacaaa ctgacagtca cctcccagaa cttgcagctg       300
gagaacctgc gcatgaaact tcccaagcct cccaagcctg tgagcaagat gcgcatggcc       360
acccgctgct gatgcaggc gctgcccatg ggagccctgc ccagggggac tagtggatct       420
caatacacgc tcccacccct cccctacccc tacgatgccc tccaacccta catctcccaa       480
cagatcatga gctgcaccaa aaaagcac catcaaacct acgtcaatgg cctgaatgcc        540
gcactcgagg cgcagaagaa agcggcggaa gccaccgacg tccccaagct cgtctccgtg       600
cagcaagcga tcaaattcaa cggcgggggg cacatcaacc attccctctt ctggaagaat       660
ctggccccgg agaaatccgg gggtggcaag atcgatcagg caccggtcct caaagcagcc       720
atcgagcagc gttggggatc cttcgataag ttcaaggatg ctttcaacac gaccctgctg       780
ggcattcagg gcagcggatg gggttggtta gtgaccgacg acccaagggg aaagctagac       840
```

-continued

```
attaccacaa cccacgacca ggatccggtg accggggcgg ccccgtctt tggggtggat    900 atgtgggagc atgcttacta ccttcagtac ttgaacgaca aagcctcgta tgccaagggc    960
atctggaacg tgatcaactg ggctgaagcg gagaatcggt acatagcggg tgacaagggt   1020
ggacacccat tcatgaagct gtag                                          1044
```

<210> SEQ ID NO 4
<211> LENGTH: 347
<212> TYPE: PRT
<213> ORGANISM: Human immunodeficiency virus + Homo sapiens + Aspergillus fumigatus

<400> SEQUENCE: 4

```
Met Arg Gly Ser His His His His His His Gly Ser Gly Tyr Gly Arg
1               5                   10                  15

Lys Lys Arg Arg Gln Arg Arg Gly Ser Met Asp Asp Gln His Asp
            20                  25                  30

Leu Ile Ser Asn Asn Glu Gln Leu Pro Met Leu Gly Arg Arg Pro Gly
            35                  40                  45

Ala Pro Glu Ser Lys Cys Ser Arg Gly Ala Leu Tyr Thr Gly Phe Ser
        50                  55                  60

Ile Leu Val Thr Leu Leu Ala Gly Gln Ala Thr Thr Ala Tyr Phe
65              70                  75                  80

Leu Tyr Gln Gln Gln Gly Arg Leu Asp Lys Leu Thr Val Thr Ser Gln
                85                  90                  95

Asn Leu Gln Leu Glu Asn Leu Arg Met Lys Leu Pro Lys Pro Pro Lys
            100                 105                 110

Pro Val Ser Lys Met Arg Met Ala Thr Pro Leu Leu Met Gln Ala Leu
        115                 120                 125

Pro Met Gly Ala Leu Pro Gln Gly Thr Ser Gly Ser Gln Tyr Thr Leu
    130                 135                 140

Pro Pro Leu Pro Tyr Pro Tyr Asp Ala Leu Gln Pro Tyr Ile Ser Gln
145                 150                 155                 160

Gln Ile Met Glu Leu His His Lys His His Gln Thr Tyr Val Asn
                165                 170                 175

Gly Leu Asn Ala Ala Leu Glu Ala Gln Lys Lys Ala Ala Glu Ala Thr
            180                 185                 190

Asp Val Pro Lys Leu Val Ser Val Gln Gln Ala Ile Lys Phe Asn Gly
        195                 200                 205

Gly Gly His Ile Asn His Ser Leu Phe Trp Lys Asn Leu Ala Pro Glu
    210                 215                 220

Lys Ser Gly Gly Gly Lys Ile Asp Gln Ala Pro Val Leu Lys Ala Ala
225                 230                 235                 240

Ile Glu Gln Arg Trp Gly Ser Phe Asp Lys Phe Lys Asp Ala Phe Asn
                245                 250                 255

Thr Thr Leu Leu Gly Ile Gln Gly Ser Gly Trp Gly Trp Leu Val Thr
            260                 265                 270

Asp Gly Pro Lys Gly Lys Leu Asp Ile Thr Thr Thr His Asp Gln Asp
        275                 280                 285

Pro Val Thr Gly Ala Ala Pro Val Phe Gly Val Asp Met Trp Glu His
    290                 295                 300

Ala Tyr Tyr Leu Gln Tyr Leu Asn Asp Lys Ala Ser Tyr Ala Lys Gly
305                 310                 315                 320

Ile Trp Asn Val Ile Asn Trp Ala Glu Ala Glu Asn Arg Tyr Ile Ala
```

```
                  325                 330                 335
Gly Asp Lys Gly Gly His Pro Phe Met Lys Leu
            340                 345
```

<210> SEQ ID NO 5
<211> LENGTH: 903
<212> TYPE: DNA
<213> ORGANISM: Human immunodeficience virus + Homo sapiens + Betula verrucosa

```
Pro Met Gly Ala Leu Pro Gln Gly Thr Ser Gly Ser Met Gly Val Phe
    130                 135                 140

Asn Tyr Glu Thr Glu Thr Thr Ser Val Ile Pro Ala Ala Arg Leu Phe
145                 150                 155                 160

Lys Ala Phe Ile Leu Asp Gly Asp Asn Leu Phe Pro Lys Val Ala Pro
                165                 170                 175

Gln Ala Ile Ser Ser Val Glu Asn Ile Glu Gly Asn Gly Pro Gly
            180                 185                 190

Thr Ile Lys Lys Ile Ser Phe Pro Glu Gly Phe Pro Phe Lys Tyr Val
            195                 200                 205

Lys Asp Arg Val Asp Glu Val Asp His Thr Asn Phe Lys Tyr Asn Tyr
    210                 215                 220

Ser Val Ile Glu Gly Gly Pro Ile Gly Asp Thr Leu Glu Lys Ile Ser
225                 230                 235                 240

Asn Glu Ile Lys Ile Val Ala Thr Pro Asp Gly Gly Ser Ile Leu Lys
                245                 250                 255

Ile Ser Asn Lys Tyr His Thr Lys Gly Asp His Glu Val Lys Ala Glu
            260                 265                 270

Gln Val Lys Ala Ser Lys Glu Met Gly Glu Thr Leu Leu Arg Ala Val
            275                 280                 285

Glu Ser Tyr Leu Leu Ala His Ser Asp Ala Tyr Asn
    290                 295                 300

<210> SEQ ID NO 7
<211> LENGTH: 1089
<212> TYPE: DNA
<213> ORGANISM: Human immunodeficiency virus + Homo sapiens +
      Dermatophagoides pteronyssinus

<400> SEQUENCE: 7
atgagaggat cgcatcacca tcaccatcac ggatctggtt acggtcgtaa aaagcgtcgc      60
cagcgtcgcc gtggatctat ggatgaccag cacgacctta tctccaacaa tgagcaactg     120
cccatgctgg ccggcgcccc tggggccccg gagagcaagt gcagccgcgg agccctgtac     180
acaggctttt ccatcctggt gactctgctc ctcgctggcc aggccaccac cgcctacttc     240
ctgtaccagc agcagggccg gctggacaaa ctgacagtca cctcccagaa cttgcagctg     300
gagaacctgc gcatgaaact tcccaagcct cccaagcctg tgagcaagat cgcatggcc      360 accccgctgc tgatgcaggc gctgcccatg ggagccctgc ccaggggac tagtggatcc      420 actaacgcat gtagtatcaa tggaaatgct ccagctgaaa tcgatttgcg acaaatgcga     480
actgtcactc ccattcgtat gcaaggaggc tgtggttcat gttgggcttt ctctggtggt     540
gccgcaactg aatcagctta tttggctcac cgtaatcaat cattggatct tgctgaacaa     600
gaattagtcg attgtgcttc caacacggt tgtcatggtg ataccattcc acgtggtatt     660
gaatacatcc aacataatgg tgtcgtccaa gaaagctact atcgatacgt tgcacgagaa     720
caatcatgcc gacgaccaaa tgcacaacgt ttcggtatct caaactattg ccaaatttac     780
ccaccaaatg caaacaaaat tcgtgaagct ttggctcaaa cccacagcgc tattgccgtc     840
attattggca tcaaagattt agacgcattc cgtcattatg atggccgaac aatcattcaa     900
cgcgataatg ttaccaacc aaactatcac gctgtcaaca ttgttggtta cagtaacgca     960
caaggtgtcg attattggat cgtacgaaac agttgggata ccaattgggg tgataatggt    1020
tacggttatt ttgctgccaa catcgatttg atgatgattg aagaatatcc atatgttgtc    1080
attctctaa                                                            1089
```

<210> SEQ ID NO 8
<211> LENGTH: 362
<212> TYPE: PRT
<213> ORGANISM: Human immunodeficiency virus + Homo sapiens + Dermatophagoides pte
<210> SEQ ID NO 9
<211> LENGTH: 39
<212> TYPE: DNA
<213> ORGANISM: Human immunodeficiency virus

<400> SEQUENCE: 9
ggttacggtc gtaaaaagcg tcgccagcgt cgccgtgga                                39

<210> SEQ ID NO 10
<211> LENGTH: 13
<212> TYPE: PRT
<213> ORGANISM: Human immunodeficiency virus

<400> SEQUENCE: 10

Gly Tyr Gly Arg Lys Lys Arg Arg Gln Arg Arg Arg Gly
1               5                   10

<210> SEQ ID NO 11
<211> LENGTH: 429
<212> TYPE: DNA
<213> ORGANISM: Homo sapiens

<400> SEQUENCE: 11
atgagaggat cgcatcacca tcaccatcac ggatctggtt acggtcgtaa aaagcgtcgc        60
cagcgtcgcc gtggatctat ggatgaccag cacgacctta tctccaacaa tgagcaactg       120
cccatgctgg gccggcgccc tggggccccg gagagcaagt gcagccgcgg agccctgtac       180
acaggctttt ccatcctggt gactctgctc ctcgctggcc aggccaccac cgcctacttc       240
ctgtaccagc agcagggccg gctggacaaa ctgacagtca cctcccagaa cttgcagctg       300
gagaacctgc gcatgaaact tcccaagcct cccaagcctg tgagcaagat gcgcatggcc       360
accccgctgc tgatgcaggc gctgcccatg ggagccctgc ccagggggac tagtctgcag       420
aagcttaat                                                               429

<210> SEQ ID NO 12
<211> LENGTH: 143
<212> TYPE: PRT
<213> ORGANISM: Homo sapiens

<400> SEQUENCE: 12

Met Arg Gly Ser His His His His His His Gly Ser Gly Tyr Gly Arg
1               5                   10                  15

Lys Lys Arg Arg Gln Arg Arg Gly Ser Met Asp Asp Gln His Asp
            20                  25                  30

Leu Ile Ser Asn Asn Glu Gln Leu Pro Met Leu Gly Arg Arg Pro Gly
        35                  40                  45

Ala Pro Glu Ser Lys Cys Ser Arg Gly Ala Leu Tyr Thr Gly Phe Ser
    50                  55                  60

Ile Leu Val Thr Leu Leu Leu Ala Gly Gln Ala Thr Thr Ala Tyr Phe
65                  70                  75                  80

Leu Tyr Gln Gln Gln Gly Arg Leu Asp Lys Leu Thr Val Thr Ser Gln
                85                  90                  95

Asn Leu Gln Leu Glu Asn Leu Arg Met Lys Leu Pro Lys Pro Pro Lys
            100                 105                 110

Pro Val Ser Lys Met Arg Met Ala Thr Pro Leu Leu Met Gln Ala Leu
        115                 120                 125

Pro Met Gly Ala Leu Pro Gln Gly Thr Ser Leu Gln Lys Leu Asn
    130                 135                 140

<210> SEQ ID NO 13
<211> LENGTH: 450
<212> TYPE: DNA
<213> ORGANISM: Aspergillus fumigatus

<400> SEQUENCE: 13

```
gcgacctgga catgcatcaa ccaacagctg aatcccaaga caaacaaatg ggaagacaag      60
cggcttctat acagtcaagc caaagccgaa agcaactccc accacgcacc tctttccgac     120
ggcaagaccg gtagcagcta cccgcactgg ttcactaacg gctacgacgg gaatggcaag     180
ctcatcaagg gtcgcacgcc atcaaattc ggaaaagccg actgtgaccg tcccccgaag      240
cacagccaga acggcatggg caaggatgac cactacctgc tggagttccc gacttttcca     300
gatggccacg actataagtt tgactcgaag aaacccaagg aagacccggg cccagcgagg     360
gtcatctata cttatcccaa caaggtgttt tgcggcattg tggcccatca gcgggggaat     420
cagggagact tgagactgtg ttctcattag                                       450
```

<210> SEQ ID NO 14
<211> LENGTH: 149
<212> TYPE: PRT
<213> ORGANISM: Aspergillus fumigatus

<400> SEQUENCE: 14

```
Ala Thr Trp Thr Cys Ile Asn Gln Gln Leu Asn Pro Lys Thr Asn Lys
 1               5                  10                  15

Trp Glu Asp Lys Arg Leu Leu Tyr Ser Gln Ala Lys Ala Glu Ser Asn
            20                  25                  30

Ser His His Ala Pro Leu Ser Asp Gly Lys Thr Gly Ser Ser Tyr Pro
        35                  40                  45

His Trp Phe Thr Asn Gly Tyr Asp Gly Asn Gly Lys Leu Ile Lys Gly
    50                  55                  60

Arg Thr Pro Ile Lys Phe Gly Lys Ala Asp Cys Asp Arg Pro Pro Lys
65                  70                  75                  80

His Ser Gln Asn Gly Met Gly Lys Asp Asp His Tyr Leu Leu Glu Phe
                85                  90                  95

Pro Thr Phe Pro Asp Gly His Asp Tyr Lys Phe Asp Ser Lys Lys Pro
            100                 105                 110

Lys Glu Asp Pro Gly Pro Ala Arg Val Ile Tyr Thr Tyr Pro Asn Lys
        115                 120                 125

Val Phe Cys Gly Ile Val Ala His Gln Arg Gly Asn Gln Gly Asp Leu
    130                 135                 140

Arg Leu Cys Ser His
145
```

<210> SEQ ID NO 15
<211> LENGTH: 633
<212> TYPE: DNA
<213> ORGANISM: Aspergillus fumigatus

<400> SEQUENCE: 15

```
atgtcacagc aatacacgct cccacccctc ccctacccct acgatgccct ccaaccctac      60
atctcccaac agatcatgga gctgcaccac aaaaagcacc atcaaaccta cgtcaatggc     120
ctgaatgccg cactcgaggc gcagaagaaa gcggcggaag ccaccgacgt ccccaagctc     180
gtctccgtgc agcaagcgat caaattcaac ggcggggggc acatcaacca ttccctcttc     240
```

```
tggaagaatc tggccccgga gaaatccggg ggtggcaaga tcgatcaggc accggtcctc    300
aaagcagcca tcgagcagcg ttggggatcc ttcgataagt tcaaggatgc tttcaacacg    360
accctgctgg gcattcaggg cagcggatgg ggttggttag tgaccgacgg acccaaggga    420
aagctagaca ttaccacaac ccacgaccag gatccggtga ccggggcggc ccccgtcttt    480
ggggtggata tgtgggagca tgcttactac cttcagtact tgaacgacaa agcctcgtat    540
gccaagggca tctggaacgt gatcaactgg gctgaagcgg agaatcggta catagcgggt    600
gacaagggtg gacacccatt catgaagctg tag                                 633
```

```
<210> SEQ ID NO 16
<211> LENGTH: 210
<212> TYPE: PRT
<213> ORGANISM: Aspergillus fumigatus

<400> SEQUENCE: 16

Met Ser Gln Gln Tyr Thr Leu Pro Pro Leu Pro Tyr Pro Tyr Asp Ala
 1               5                  10                  15

Leu Gln Pro Tyr Ile Ser Gln Gln Ile Met Glu Leu His His Lys Lys
                20                  25                  30

His His Gln Thr Tyr Val Asn Gly Leu Asn Ala Ala Leu Glu Ala Gln
            35                  40                  45

Lys Lys Ala Ala Glu Ala Thr Asp Val Pro Lys Leu Val Ser Val Gln
 50                  55                  60

Gln Ala Ile Lys Phe Asn Gly Gly His Ile Asn His Ser Leu Phe
 65                  70                  75                  80

Trp Lys Asn Leu Ala Pro Glu Lys Ser Gly Gly Lys Ile Asp Gln
                85                  90                  95

Ala Pro Val Leu Lys Ala Ala Ile Glu Gln Arg Trp Gly Ser Phe Asp
            100                 105                 110

Lys Phe Lys Asp Ala Phe Asn Thr Thr Leu Leu Gly Ile Gln Gly Ser
            115                 120                 125

Gly Trp Gly Trp Leu Val Thr Asp Gly Pro Lys Gly Lys Leu Asp Ile
        130                 135                 140

Thr Thr Thr His Asp Gln Asp Pro Val Thr Gly Ala Ala Pro Val Phe
145                 150                 155                 160

Gly Val Asp Met Trp Glu His Ala Tyr Tyr Leu Gln Tyr Leu Asn Asp
                165                 170                 175

Lys Ala Ser Tyr Ala Lys Gly Ile Trp Asn Val Ile Asn Trp Ala Glu
            180                 185                 190

Ala Glu Asn Arg Tyr Ile Ala Gly Asp Lys Gly Gly His Pro Phe Met
        195                 200                 205

Lys Leu
    210
```

```
<210> SEQ ID NO 17
<211> LENGTH: 519
<212> TYPE: DNA
<213> ORGANISM: Betula verrucosa

<400> SEQUENCE: 17
atgagaggat cgcatcacca tcaccatcac ggatccatgg gtgttttcaa ctacgaaacc     60
gaaaccacct ccgttatccc ggctgctcgt ctgttcaagg ccttcatcct ggacggtgac    120
aacctgttcc ctaaggttgc tccgcaggct atctcctccg ttgaaaacat cgaaggtaac    180
ggtggcccgg gtaccatcaa gaaaatctcc ttcccggaag gtttcccatt taaatacgta    240
```

-continued

```
aaagaccgtg ttgacgaagt tgaccacacc aacttcaaat acaactactc cgttatcgaa    300
ggtggtccaa ttggtgacac cctggaaaaa atctccaacg aaatcaaaat cgtggcaacc    360
ccggacggtg gttccatcct taagatctcc aacaaatacc acaccaaagg tgaccacgaa    420
gttaaagctg aacaggttaa agcttcgaaa gaaatgggtg aaaccctgct gcgtgctgtt    480
gaatcctacc tgctggctca ctccgatgca tacaactaa                           519
```

<210> SEQ ID NO 18
<211> LENGTH: 172
<212> TYPE: PRT
<213> ORGANISM: Betula verrucosa

<400> SEQUENCE: 18

```
Met Arg Gly Ser His His His His His His Gly Ser Met Gly Val Phe
1               5                   10                  15

Asn Tyr Glu Thr Glu Thr Thr Ser Val Ile Pro Ala Ala Arg Leu Phe
            20                  25                  30

Lys Ala Phe Ile Leu Asp Gly Asp Asn Leu Phe Pro Lys Val Ala Pro
        35                  40                  45

Gln Ala Ile Ser Ser Val Glu Asn Ile Glu Gly Asn Gly Gly Pro Gly
    50                  55                  60

Thr Ile Lys Lys Ile Ser Phe Pro Glu Gly Phe Pro Phe Lys Tyr Val
65                  70                  75                  80

Lys Asp Arg Val Asp Glu Val Asp His Thr Asn Phe Lys Tyr Asn Tyr
                85                  90                  95

Ser Val Ile Glu Gly Gly Pro Ile Gly Asp Thr Leu Glu Lys Ile Ser
            100                 105                 110

Asn Glu Ile Lys Ile Val Ala Thr Pro Asp Gly Gly Ser Ile Leu Lys
        115                 120                 125

Ile Ser Asn Lys Tyr His Thr Lys Gly Asp His Glu Val Lys Ala Glu
    130                 135                 140

Gln Val Lys Ala Ser Lys Glu Met Gly Glu Thr Leu Leu Arg Ala Val
145                 150                 155                 160

Glu Ser Tyr Leu Leu Ala His Ser Asp Ala Tyr Asn
                165                 170
```

<210> SEQ ID NO 19
<211> LENGTH: 1099
<212> TYPE: DNA
<213> ORGANISM: Dermatophagoides pteronyssinus

<400> SEQUENCE: 19

```
gaattccttt ttttttcttt ctctctctaa aatctaaaat ccatccaaca tgaaaattgt     60
tttggccatc gcctcattgt tggcattgag cgctgtttat gctcgtccat catcgatcaa    120
aacttttgaa gaatacaaaa aagccttcaa caaaagttat gctaccttcg aagatgaaga    180
agctgcccgt aaaaactttt tggaatcagt aaaatatgtt caatcaaatg gaggtgccat    240
caaccatttg tccgatttgt cgttggatga attcaaaaac cgatttttga tgagtgcaga    300
agcttttgaa cacctcaaaa ctcaattcga tttgaatgct gaaactaacg cctgcagtat    360
caatggaaat gctccagctg aaatcgattt gcgacaaatg cgaactgtca ctcccattcg    420
tatgcaagga ggctgtggtt catgttgggc tttctctggt gttgccgcaa ctgaatcagc    480
ttatttggct taccgtaatc aatcattgga tcttgctgaa caagaattag tcgattgtgc    540
ttcccaacac ggttgtcatg gtgataccat tccacgtggt attgaataca tccaacataa    600
```

-continued

```
tggtgtcgtc caagaaagct actatcgata cgttgcacga aacaatcat gccgacgacc    660 aaatgcacaa cgtttcggta tctcaaacta ttgccaaatt tacccaccaa atgtaaacaa    720
aattcgtgaa gctttggctc aaacccacag cgctattgcc gtcattattg catcaaaga    780 tttagacgca ttccgtcatt atgatggccg aacaatcatt caacgcgata tggttacca    840 accaaactat cacgctgtca acattgttgg ttacagtaac gcacaaggtg tcgattattg    900
gatcgtacga aacagttggg ataccaattg gggtgataat ggttacggtt attttgctgc    960
caacatcgat ttgatgatga ttgaagaata tccatatgtt gtcattctct aaacaaaaag   1020
acaatttctt atatgattgt cactaattta tttaaaatca aaattttag aaaatgaata   1080 aattcattca caaaaatta                                                1099
```

<210> SEQ ID NO 20
<211> LENGTH: 320
<212> TYPE: PRT
<213> ORGANISM: Dermatophagoides pteronyssinus

<400> SEQUENCE: 20

```
Met Lys Ile Val Leu Ala Ile Ala Ser Leu Leu Ala Leu Ser Ala Val
1               5                   10                  15

Tyr Ala Arg Pro Ser Ser Ile Lys Thr Phe Glu Glu Tyr Lys Lys Ala
            20                  25                  30

Phe Asn Lys Ser Tyr Ala Thr Phe Glu Asp Glu Glu Ala Ala Arg Lys
        35                  40                  45

Asn Phe Leu Glu Ser Val Lys Tyr Val Gln Ser Asn Gly Gly Ala Ile
    50                  55                  60

Asn His Leu Ser Asp Leu Ser Leu Asp Glu Phe Lys Asn Arg Phe Leu
65                  70                  75                  80

Met Ser Ala Glu Ala Phe Glu His Leu Lys Thr Gln Phe Asp Leu Asn
                85                  90                  95

Ala Glu Thr Asn Ala Cys Ser Ile Asn Gly Asn Ala Pro Ala Glu Ile
            100                 105                 110

Asp Leu Arg Gln Met Arg Thr Val Thr Pro Ile Arg Met Gln Gly Gly
        115                 120                 125

Cys Gly Ser Cys Trp Ala Phe Ser Gly Val Ala Ala Thr Glu Ser Ala
    130                 135                 140

Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
            180                 185                 190

Arg Tyr Val Ala Arg Glu Gln Ser Cys Arg Arg Pro Asn Ala Gln Arg
        195                 200                 205

Phe Gly Ile Ser Asn Tyr Cys Gln Ile Tyr Pro Pro Asn Val Asn Lys
    210                 215                 220

Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr His Ala Val Asn Ile
            260                 265                 270

Val Gly Tyr Ser Asn Ala Gln Gly Val Asp Tyr Trp Ile Val Arg Asn
```

```
                275                 280                 285
Ser Trp Asp Thr Asn Trp Gly Asp Asn Gly Tyr Gly Tyr Phe Ala Ala
    290                 295                 300

Asn Ile Asp Leu Met Met Ile Glu Glu Tyr Pro Tyr Val Val Ile Leu
305                 310                 315                 320

<210> SEQ ID NO 21
<211> LENGTH: 876
<212> TYPE: DNA
<213> ORGANISM: Tat-Ii-fel d 1
<220> FEATURE:
<221> NAME/KEY: CDS
<222> LOCATION: (1)..(876)

<400> SEQUENCE: 21 atg ggt tac ggt cgt aaa aag cgt cgc cag cgt cgc cgt gga tct atg       48
Met Gly Tyr Gly Arg Lys Lys Arg Arg Gln Arg Arg Arg Gly Ser Met
1               5                   10                  15 gat gac cag cac gac ctt atc tcc aac aat gag caa ctg ccc atg ctg       96
Asp Asp Gln His Asp Leu Ile Ser Asn Asn Glu Gln Leu Pro Met Leu
                20                  25                  30 ggc cgg cgc cct ggg gcc ccg gag agc aag tgc agc cgc gga gcc ctg      144
Gly Arg Arg Pro Gly Ala Pro Glu Ser Lys Cys Ser Arg Gly Ala Leu
        35                  40                  45 tac aca ggc ttt tcc atc ctg gtg act ctg ctc ctc gct ggc cag gcc      192
Tyr Thr Gly Phe Ser Ile Leu Val Thr Leu Leu Leu Ala Gly Gln Ala
50                  55                  60 acc acc gcc tac ttc ctg tac cag cag cag ggc cgg ctg gac aaa ctg      240
Thr Thr Ala Tyr Phe Leu Tyr Gln Gln Gln Gly Arg Leu Asp Lys Leu
65                  70                  75                  80 aca gtc acc tcc cag aac ttg cag ctg gag aac ctg cgc atg aaa ctt      288
Thr Val Thr Ser Gln Asn Leu Gln Leu Glu Asn Leu Arg Met Lys Leu
                85                  90                  95 ccc aag cct ccc aag cct gtg agc aag atg cgc atg gcc acc ccg ctg      336
Pro Lys Pro Pro Lys Pro Val Ser Lys Met Arg Met Ala Thr Pro Leu
            100                 105                 110 ctg atg cag gcg ctg ccc atg gga gcc ctg ccc cag ggg act agt gga      384
Leu Met Gln Ala Leu Pro Met Gly Ala Leu Pro Gln Gly Thr Ser Gly
        115                 120                 125 tcc gtt aaa atg gct gaa acc tgc ccg atc ttc tac gac gtt ttc ttc      432
Ser Val Lys Met Ala Glu Thr Cys Pro Ile Phe Tyr Asp Val Phe Phe
    130                 135                 140 gct gtt gct aac ggt aac gaa ctg ctg ctg gac ctg tcc ctg acc aaa      480
Ala Val Ala Asn Gly Asn Glu Leu Leu Leu Asp Leu Ser Leu Thr Lys
145                 150                 155                 160 gtt aac gct acc gaa ccg gaa cgt acc gct atg aaa aaa atc cag gac      528
Val Asn Ala Thr Glu Pro Glu Arg Thr Ala Met Lys Lys Ile Gln Asp
                165                 170                 175 tgc tac gtt gaa aac ggt ctg atc tcc cgt gtt ctg gac ggt ctg gtt      576
Cys Tyr Val Glu Asn Gly Leu Ile Ser Arg Val Leu Asp Gly Leu Val
            180                 185                 190 atg acc acc atc tcc tcc tcc aaa gac tgc atg ggt gaa gct gtt cag      624
Met Thr Thr Ile Ser Ser Ser Lys Asp Cys Met Gly Glu Ala Val Gln
        195                 200                 205 aac acc gtt gaa gac ctg aaa ctg aac acc ctg ggt cgt gaa atc tgc      672
Asn Thr Val Glu Asp Leu Lys Leu Asn Thr Leu Gly Arg Glu Ile Cys
    210                 215                 220 ccg gct gtt aaa cgt gac gtt gac ctg ttc ctg acc ggt acc ccg gac      720
Pro Ala Val Lys Arg Asp Val Asp Leu Phe Leu Thr Gly Thr Pro Asp
225                 230                 235                 240
```

```
gaa tac gtt gaa cag gtt gct cag tac aaa gct ctg ccg gtt gtt ctg    768
Glu Tyr Val Glu Gln Val Ala Gln Tyr Lys Ala Leu Pro Val Val Leu
            245                 250                 255 gaa aac gct cgt atc ctg aaa aac tgc gtt gac gct aaa atg acc gaa    816
Glu Asn Ala Arg Ile Leu Lys Asn Cys Val Asp Ala Lys Met Thr Glu
        260                 265                 270 gaa gac aaa gaa aac gct ctg tcc ctg ctg gac aaa atc tac acc tcc    864
Glu Asp Lys Glu Asn Ala Leu Ser Leu Leu Asp Lys Ile Tyr Thr Ser
    275                 280                 285 ccg ctg tgc taa                                                    876
Pro Leu Cys
    290

<210> SEQ ID NO 22
<211> LENGTH: 291
<212> TYPE: PRT
<213> ORGANISM: Tat-Ii-fel d 1

<400> SEQUENCE: 22

Met Gly Tyr Gly Arg Lys Lys Arg Gln Arg Arg Gly Ser Met
1               5                   10                  15

Asp Asp Gln His Asp Leu Ile Ser Asn Asn Glu Gln Leu Pro Met Leu
            20                  25                  30

Gly Arg Arg Pro Gly Ala Pro Glu Ser Lys Cys Ser Arg Gly Ala Leu
        35                  40                  45

Tyr Thr Gly Phe Ser Ile Leu Val Thr Leu Leu Ala Gly Gln Ala
    50                  55                  60

Thr Thr Ala Tyr Phe Leu Tyr Gln Gln Gln Gly Arg Leu Asp Lys Leu
65                  70                  75                  80

Thr Val Thr Ser Gln Asn Leu Gln Leu Glu Asn Leu Arg Met Lys Leu
                85                  90                  95

Pro Lys Pro Pro Lys Pro Val Ser Lys Met Arg Met Ala Thr Pro Leu
            100                 105                 110

Leu Met Gln Ala Leu Pro Met Gly Ala Leu Pro Gln Gly Thr Ser Gly
        115                 120                 125

Ser Val Lys Met Ala Glu Thr Cys Pro Ile Phe Tyr Asp Val Phe Phe
    130                 135                 140

Ala Val Ala Asn Gly Asn Glu Leu Leu Leu Asp Leu Ser Leu Thr Lys
145                 150                 155                 160

Val Asn Ala Thr Glu Pro Glu Arg Thr Ala Met Lys Lys Ile Gln Asp
                165                 170                 175

Cys Tyr Val Glu Asn Gly Leu Ile Ser Arg Val Leu Asp Gly Leu Val
            180                 185                 190

Met Thr Thr Ile Ser Ser Lys Asp Cys Met Gly Glu Ala Val Gln
        195                 200                 205

Asn Thr Val Glu Asp Leu Lys Leu Asn Thr Leu Gly Arg Glu Ile Cys
    210                 215                 220

Pro Ala Val Lys Arg Asp Val Asp Leu Phe Leu Thr Gly Thr Pro Asp
225                 230                 235                 240

Glu Tyr Val Glu Gln Val Ala Gln Tyr Lys Ala Leu Pro Val Val Leu
                245                 250                 255

Glu Asn Ala Arg Ile Leu Lys Asn Cys Val Asp Ala Lys Met Thr Glu
            260                 265                 270

Glu Asp Lys Glu Asn Ala Leu Ser Leu Leu Asp Lys Ile Tyr Thr Ser
        275                 280                 285

Pro Leu Cys
```

-continued

290

<210> SEQ ID NO 23
<211> LENGTH: 909
<212> TYPE: DNA
<213> ORGANISM: his-tat-Ii-fel d 1
<220> FEATURE:
<221> NAME/KEY: CDS
<222> LOCATION: (1)..(876)

<400> SEQUENCE: 23

| | | | | | | | | | | | | | | | | |
|---|---|---|---|---|---|---|---|---|---|---|---|---|---|---|---|---|
| atg | aga | gga | tcg | cat | cac | cat | cac | cat | cac | gga | tct | ggt | tac | ggt | cgt | 48 |
| Met | Arg | Gly | Ser | His | His | His | His | His | His | Gly | Ser | Gly | Tyr | Gly | Arg | |
| 1 | | | | 5 | | | | | 10 | | | | | 15 | | |
| aaa | aag | cgt | cgc | cag | cgt | cgc | cgt | gga | tct | atg | gat | gac | cag | cac | gac | 96 |
| Lys | Lys | Arg | Arg | Gln | Arg | Arg | Arg | Gly | Ser | Met | Asp | Asp | Gln | His | Asp | |
| | | | 20 | | | | | 25 | | | | | 30 | | | |
| ctt | atc | tcc | aac | aat | gag | caa | ctg | ccc | atg | ctg | ggc | cgg | cgc | cct | ggg | 144 |
| Leu | Ile | Ser | Asn | Asn | Glu | Gln | Leu | Pro | Met | Leu | Gly | Arg | Arg | Pro | Gly | |
| | 35 | | | | | 40 | | | | | 45 | | | | | |
| gcc | ccg | gag | agc | aag | tgc | agc | cgc | gga | gcc | ctg | tac | aca | ggc | ttt | tcc | 192 |
| Ala | Pro | Glu | Ser | Lys | Cys | Ser | Arg | Gly | Ala | Leu | Tyr | Thr | Gly | Phe | Ser | |
| 50 | | | | | 55 | | | | | 60 | | | | | | |
| atc | ctg | gtg | act | ctg | ctc | ctc | gct | ggc | cag | gcc | acc | acc | gcc | tac | ttc | 240 |
| Ile | Leu | Val | Thr | Leu | Leu | Leu | Ala | Gly | Gln | Ala | Thr | Thr | Ala | Tyr | Phe | |
| 65 | | | | 70 | | | | | 75 | | | | | 80 | | |
| ctg | tac | cag | cag | cag | ggc | cgg | ctg | gac | aaa | ctg | aca | gtc | acc | tcc | cag | 288 |
| Leu | Tyr | Gln | Gln | Gln | Gly | Arg | Leu | Asp | Lys | Leu | Thr | Val | Thr | Ser | Gln | |
| | | | | 85 | | | | | 90 | | | | | 95 | | |
| aac | ttg | cag | ctg | gag | aac | ctg | cgc | atg | aaa | ctt | ccc | aag | cct | ccc | aag | 336 |
| Asn | Leu | Gln | Leu | Glu | Asn | Leu | Arg | Met | Lys | Leu | Pro | Lys | Pro | Pro | Lys | |
| | | | 100 | | | | | 105 | | | | | 110 | | | |
| cct | gtg | agc | aag | atg | cgc | atg | gcc | acc | ccg | ctg | ctg | atg | cag | gcg | ctg | 384 |
| Pro | Val | Ser | Lys | Met | Arg | Met | Ala | Thr | Pro | Leu | Leu | Met | Gln | Ala | Leu | |
| | | 115 | | | | | 120 | | | | | 125 | | | | |
| ccc | atg | gga | gcc | ctg | ccc | cag | ggg | act | agt | gga | tcc | gtt | aaa | atg | gct | 432 |
| Pro | Met | Gly | Ala | Leu | Pro | Gln | Gly | Thr | Ser | Gly | Ser | Val | Lys | Met | Ala | |
| | 130 | | | | | 135 | | | | | 140 | | | | | |
| gaa | acc | tgc | ccg | atc | ttc | tac | gac | gtt | ttc | ttc | gct | gtt | gct | aac | ggt | 480 |
| Glu | Thr | Cys | Pro | Ile | Phe | Tyr | Asp | Val | Phe | Phe | Ala | Val | Ala | Asn | Gly | |
| 145 | | | | | 150 | | | | | 155 | | | | | 160 | |
| aac | gaa | ctg | ctg | ctg | gac | ctg | tcc | ctg | acc | aaa | gtt | aac | gct | acc | gaa | 528 |
| Asn | Glu | Leu | Leu | Leu | Asp | Leu | Ser | Leu | Thr | Lys | Val | Asn | Ala | Thr | Glu | |
| | | | | 165 | | | | | 170 | | | | | 175 | | |
| ccg | gaa | cgt | acc | gct | atg | aaa | aaa | atc | cag | gac | tgc | tac | gtt | gaa | aac | 576 |
| Pro | Glu | Arg | Thr | Ala | Met | Lys | Lys | Ile | Gln | Asp | Cys | Tyr | Val | Glu | Asn | |
| | | | 180 | | | | | 185 | | | | | 190 | | | |
| ggt | ctg | atc | tcc | cgt | gtt | ctg | gac | ggt | ctg | gtt | atg | acc | acc | atc | tcc | 624 |
| Gly | Leu | Ile | Ser | Arg | Val | Leu | Asp | Gly | Leu | Val | Met | Thr | Thr | Ile | Ser | |
| | | 195 | | | | | 200 | | | | | 205 | | | | |
| tcc | tcc | aaa | gac | tgc | atg | ggt | gaa | gct | gtt | cag | aac | acc | gtt | gaa | gac | 672 |
| Ser | Ser | Lys | Asp | Cys | Met | Gly | Glu | Ala | Val | Gln | Asn | Thr | Val | Glu | Asp | |
| | 210 | | | | | 215 | | | | | 220 | | | | | |
| ctg | aaa | ctg | aac | acc | ctg | ggt | cgt | gaa | atc | tgc | ccg | gct | gtt | aaa | cgt | 720 |
| Leu | Lys | Leu | Asn | Thr | Leu | Gly | Arg | Glu | Ile | Cys | Pro | Ala | Val | Lys | Arg | |
| 225 | | | | | 230 | | | | | 235 | | | | | 240 | |
| gac | gtt | gac | ctg | ttc | ctg | acc | ggt | acc | ccg | gac | gaa | tac | gtt | gaa | cag | 768 |
| Asp | Val | Asp | Leu | Phe | Leu | Thr | Gly | Thr | Pro | Asp | Glu | Tyr | Val | Glu | Gln | |
| | | | | 245 | | | | | 250 | | | | | 255 | | |
| gtt | gct | cag | tac | aaa | gct | ctg | ccg | gtt | gtt | ctg | gaa | aac | gct | cgt | atc | 816 |
| Val | Ala | Gln | Tyr | Lys | Ala | Leu | Pro | Val | Val | Leu | Glu | Asn | Ala | Arg | Ile | |

-continued

```
                    260                 265                 270
ctg aaa aac tgc gtt gac gct aaa atg acc gaa gaa gac aaa gaa aac    864
Leu Lys Asn Cys Val Asp Ala Lys Met Thr Glu Glu Asp Lys Glu Asn
        275                 280                 285 gct ctg tcc ctg ctggacaaaa tctacacctc cccgctgtgc taa                909
Ala Leu Ser Leu
    290
```

<210> SEQ ID NO 24
<211> LENGTH: 292
<212> TYPE: PRT
<213> ORGANISM: his-tat-Ii-fel d 1

<400> SEQUENCE: 24

```
Met Arg Gly Ser His His His His His His Gly Ser Gly Tyr Gly Arg
1               5                   10                  15

Lys Lys Arg Arg Gln Arg Arg Gly Ser Met Asp Asp Gln His Asp
            20                  25                  30

Leu Ile Ser Asn Asn Glu Gln Leu Pro Met Leu Gly Arg Arg Pro Gly
        35                  40                  45

Ala Pro Glu Ser Lys Cys Ser Arg Gly Ala Leu Tyr Thr Gly Phe Ser
    50                  55                  60

Ile Leu Val Thr Leu Leu Leu Ala Gly Gln Ala Thr Thr Ala Tyr Phe
65                  70                  75                  80

Leu Tyr Gln Gln Gln Gly Arg Leu Asp Lys Leu Thr Val Thr Ser Gln
                85                  90                  95

Asn Leu Gln Leu Glu Asn Leu Arg Met Lys Leu Pro Lys Pro Pro Lys
            100                 105                 110

Pro Val Ser Lys Met Arg Met Ala Thr Pro Leu Leu Met Gln Ala Leu
        115                 120                 125

Pro Met Gly Ala Leu Pro Gln Gly Thr Ser Gly Ser Val Lys Met Ala
    130                 135                 140

Glu Thr Cys Pro Ile Phe Tyr Asp Val Phe Phe Ala Val Ala Asn Gly
145                 150                 155                 160

Asn Glu Leu Leu Leu Asp Leu Ser Leu Thr Lys Val Asn Ala Thr Glu
                165                 170                 175

Pro Glu Arg Thr Ala Met Lys Lys Ile Gln Asp Cys Tyr Val Glu Asn
            180                 185                 190

Gly Leu Ile Ser Arg Val Leu Asp Gly Leu Val Met Thr Thr Ile Ser
        195                 200                 205

Ser Ser Lys Asp Cys Met Gly Glu Ala Val Gln Asn Thr Val Glu Asp
    210                 215                 220

Leu Lys Leu Asn Thr Leu Gly Arg Glu Ile Cys Pro Ala Val Lys Arg
225                 230                 235                 240

Asp Val Asp Leu Phe Leu Thr Gly Thr Pro Asp Glu Tyr Val Glu Gln
                245                 250                 255

Val Ala Gln Tyr Lys Ala Leu Pro Val Val Leu Glu Asn Ala Arg Ile
            260                 265                 270

Leu Lys Asn Cys Val Asp Ala Lys Met Thr Glu Glu Asp Lys Glu Asn
        275                 280                 285

Ala Leu Ser Leu
    290
```

<210> SEQ ID NO 25
<211> LENGTH: 870
<212> TYPE: DNA

<213> ORGANISM: tat-Ii-bet v 1
<220> FEATURE:
<221> NAME/KEY: CDS
<222> LOCATION: (1)..(870)

<400> SEQUENCE: 25

| | | | | | | | | | | | | | | | | |
|---|---|---|---|---|---|---|---|---|---|---|---|---|---|---|---|---|
| atg | ggt | tac | ggt | cgt | aaa | aag | cgt | cgc | cag | cgt | cgc | cgt | gga | tct | atg | 48 |
| Met | Gly | Tyr | Gly | Arg | Lys | Lys | Arg | Arg | Gln | Arg | Arg | Arg | Gly | Ser | Met | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gat | gac | cag | cac | gac | ctt | atc | tcc | aac | aat | gag | caa | ctg | ccc | atg | ctg | 96 |
| Asp | Asp | Gln | His | Asp | Leu | Ile | Ser | Asn | Asn | Glu | Gln | Leu | Pro | Met | Leu | |
| | | | 20 | | | | 25 | | | | | 30 | | | | |

| | | | | | | | | | | | | | | | | |
|---|---|---|---|---|---|---|---|---|---|---|---|---|---|---|---|---|
| ggc | cgg | cgc | cct | ggg | gcc | ccg | gag | agc | aag | tgc | agc | cgc | gga | gcc | ctg | 144 |
| Gly | Arg | Arg | Pro | Gly | Ala | Pro | Glu | Ser | Lys | Cys | Ser | Arg | Gly | Ala | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| tac | aca | ggc | ttt | tcc | atc | ctg | gtg | act | ctg | ctc | ctc | gct | ggc | cag | gcc | 192 |
| Tyr | Thr | Gly | Phe | Ser | Ile | Leu | Val | Thr | Leu | Leu | Leu | Ala | Gly | Gln | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| acc | acc | gcc | tac | ttc | tac | cag | cag | cag | ggc | cgg | ctg | gac | aaa | ctg | | 240 |
| Thr | Thr | Ala | Tyr | Phe | Leu | Tyr | Gln | Gln | Gln | Gly | Arg | Leu | Asp | Lys | Leu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| aca | gtc | acc | tcc | cag | aac | ttg | cag | ctg | gag | aac | ctg | cgc | atg | aaa | ctt | 288 |
| Thr | Val | Thr | Ser | Gln | Asn | Leu | Gln | Leu | Glu | Asn | Leu | Arg | Met | Lys | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| ccc | aag | cct | ccc | aag | cct | gtg | agc | aag | atg | cgc | atg | gcc | acc | ccg | ctg | 336 |
| Pro | Lys | Pro | Pro | Lys | Pro | Val | Ser | Lys | Met | Arg | Met | Ala | Thr | Pro | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| ctg | atg | cag | gcg | ctg | ccc | atg | gga | gcc | ctg | ccc | cag | ggg | act | agt | gga | 384 |
| Leu | Met | Gln | Ala | Leu | Pro | Met | Gly | Ala | Leu | Pro | Gln | Gly | Thr | Ser | Gly | |
| | | 115 | | | | | 120 | | | | | 125 | | | | |

| | | | | | | | | | | | | | | | | |
|---|---|---|---|---|---|---|---|---|---|---|---|---|---|---|---|---|
| tcc | atg | ggt | gtt | ttc | aat | tac | gaa | act | gag | acc | acc | tct | gtt | atc | cca | 432 |
| Ser | Met | Gly | Val | Phe | Asn | Tyr | Glu | Thr | Glu | Thr | Thr | Ser | Val | Ile | Pro | |
| 130 | | | | | 135 | | | | | 140 | | | | | | |

| | | | | | | | | | | | | | | | | |
|---|---|---|---|---|---|---|---|---|---|---|---|---|---|---|---|---|
| gca | gct | cga | ctg | ttc | aag | gcc | ttt | atc | ctt | gat | ggc | gat | aat | ctc | ttt | 480 |
| Ala | Ala | Arg | Leu | Phe | Lys | Ala | Phe | Ile | Leu | Asp | Gly | Asp | Asn | Leu | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cca | aag | gtt | gca | ccc | caa | gcc | att | agc | agt | gtt | gaa | aac | att | gaa | gga | 528 |
| Pro | Lys | Val | Ala | Pro | Gln | Ala | Ile | Ser | Ser | Val | Glu | Asn | Ile | Glu | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| aat | gga | ggg | cct | gga | acc | att | aag | aag | atc | agc | ttt | ccc | gaa | ggc | ttc | 576 |
| Asn | Gly | Gly | Pro | Gly | Thr | Ile | Lys | Lys | Ile | Ser | Phe | Pro | Glu | Gly | Phe | |
| | | | 180 | | | | | 185 | | | | | 190 | | | |

| | | | | | | | | | | | | | | | | |
|---|---|---|---|---|---|---|---|---|---|---|---|---|---|---|---|---|
| cct | ttc | aag | tac | gtg | aag | gac | aga | gtt | gat | gag | gtg | gac | cac | aca | aac | 624 |
| Pro | Phe | Lys | Tyr | Val | Lys | Asp | Arg | Val | Asp | Glu | Val | Asp | His | Thr | Asn | |
| | | 195 | | | | | 200 | | | | | 205 | | | | |

| | | | | | | | | | | | | | | | | |
|---|---|---|---|---|---|---|---|---|---|---|---|---|---|---|---|---|
| ttc | aaa | tac | aat | tac | agc | gtg | atc | gag | ggc | ggt | ccc | ata | ggc | gac | aca | 672 |
| Phe | Lys | Tyr | Asn | Tyr | Ser | Val | Ile | Glu | Gly | Gly | Pro | Ile | Gly | Asp | Thr | |
| 210 | | | | | 215 | | | | | 220 | | | | | | |

| | | | | | | | | | | | | | | | | |
|---|---|---|---|---|---|---|---|---|---|---|---|---|---|---|---|---|
| ttg | gag | aag | atc | tcc | aac | gag | ata | aag | ata | gtg | gca | acc | cct | gat | gga | 720 |
| Leu | Glu | Lys | Ile | Ser | Asn | Glu | Ile | Lys | Ile | Val | Ala | Thr | Pro | Asp | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gga | tcc | atc | ttg | aag | atc | agc | aac | aag | tac | cac | acc | aaa | ggt | gac | cat | 768 |
| Gly | Ser | Ile | Leu | Lys | Ile | Ser | Asn | Lys | Tyr | His | Thr | Lys | Gly | Asp | His | |
| | | | | 245 | | | | | 250 | | | | | 255 | | |

| | | | | | | | | | | | | | | | | |
|---|---|---|---|---|---|---|---|---|---|---|---|---|---|---|---|---|
| gag | gtg | aag | gca | gag | cag | gtt | aag | gca | agt | aaa | gaa | atg | ggc | gag | aca | 816 |
| Glu | Val | Lys | Ala | Glu | Gln | Val | Lys | Ala | Ser | Lys | Glu | Met | Gly | Glu | Thr | |
| | | | 260 | | | | | 265 | | | | | 270 | | | |

| | | | | | | | | | | | | | | | | |
|---|---|---|---|---|---|---|---|---|---|---|---|---|---|---|---|---|
| ctt | ttg | agg | gcc | gtt | gag | agc | tac | ctc | ttg | gca | cac | tcc | gat | gcc | tac | 864 |
| Leu | Leu | Arg | Ala | Val | Glu | Ser | Tyr | Leu | Leu | Ala | His | Ser | Asp | Ala | Tyr | |
| | | 275 | | | | | 280 | | | | | 285 | | | | |

-continued

```
aac taa                                                              870
Asn <210> SEQ ID NO 26
<211> LENGTH: 289
<212> TYPE: PRT
<213> ORGANISM: tat-Ii-bet v 1

<400> SEQUENCE: 26

Met Gly Tyr Gly Arg Lys Lys Arg Arg Gln Arg Arg Arg Gly Ser Met
1               5                   10                  15

Asp Asp Gln His Asp Leu Ile Ser Asn Asn Glu Gln Leu Pro Met Leu
            20                  25                  30

Gly Arg Arg Pro Gly Ala Pro Glu Ser Lys Cys Ser Arg Gly Ala Leu
        35                  40                  45

Tyr Thr Gly Phe Ser Ile Leu Val Thr Leu Leu Leu Ala Gly Gln Ala
    50                  55                  60

Thr Thr Ala Tyr Phe Leu Tyr Gln Gln Gln Gly Arg Leu Asp Lys Leu
65                  70                  75                  80

Thr Val Thr Ser Gln Asn Leu Gln Leu Glu Asn Leu Arg Met Lys Leu
                85                  90                  95

Pro Lys Pro Pro Lys Pro Val Ser Lys Met Arg Met Ala Thr Pro Leu
            100                 105                 110

Leu Met Gln Ala Leu Pro Met Gly Ala Leu Pro Gln Gly Thr Ser Gly
        115                 120                 125

Ser Met Gly Val Phe Asn Tyr Glu Thr Glu Thr Thr Ser Val Ile Pro
    130                 135                 140

Ala Ala Arg Leu Phe Lys Ala Phe Ile Leu Asp Gly Asp Asn Leu Phe
145                 150                 155                 160

Pro Lys Val Ala Pro Gln Ala Ile Ser Ser Val Glu Asn Ile Glu Gly
                165                 170                 175

Asn Gly Gly Pro Gly Thr Ile Lys Lys Ile Ser Phe Pro Glu Gly Phe
            180                 185                 190

Pro Phe Lys Tyr Val Lys Asp Arg Val Asp Glu Val Asp His Thr Asn
        195                 200                 205

Phe Lys Tyr Asn Tyr Ser Val Ile Glu Gly Gly Pro Ile Gly Asp Thr
    210                 215                 220

Leu Glu Lys Ile Ser Asn Glu Ile Lys Ile Val Ala Thr Pro Asp Gly
225                 230                 235                 240

Gly Ser Ile Leu Lys Ile Ser Asn Lys Tyr His Thr Lys Gly Asp His
                245                 250                 255

Glu Val Lys Ala Glu Gln Val Lys Ala Ser Lys Glu Met Gly Glu Thr
            260                 265                 270

Leu Leu Arg Ala Val Glu Ser Tyr Leu Leu Ala His Ser Asp Ala Tyr
        275                 280                 285

Asn

<210> SEQ ID NO 27
<211> LENGTH: 1056
<212> TYPE: DNA
<213> ORGANISM: tat-Ii-der p 1
<220> FEATURE:
<221> NAME/KEY: CDS
<222> LOCATION: (1)..(1056)

<400> SEQUENCE: 27 atg ggt tac ggt cgt aaa aag cgt cgc cag cgt cgc cgt gga tct atg       48
```

```
Met Gly Tyr Gly Arg Lys Lys Arg Arg Gln Arg Arg Gly Ser Met
1               5                   10                  15 gat gac cag cac gac ctt atc tcc aac aat gag caa ctg ccc atg ctg        96
Asp Asp Gln His Asp Leu Ile Ser Asn Asn Glu Gln Leu Pro Met Leu
            20                  25                  30 ggc cgg cgc cct ggg gcc ccg gag agc aag tgc agc cgc gga gcc ctg       144
Gly Arg Arg Pro Gly Ala Pro Glu Ser Lys Cys Ser Arg Gly Ala Leu
        35                  40                  45 tac aca ggc ttt tcc atc ctg gtg act ctg ctc ctc gct ggc cag gcc       192
Tyr Thr Gly Phe Ser Ile Leu Val Thr Leu Leu Leu Ala Gly Gln Ala
    50                  55                  60 acc acc gcc tac ttc ctg tac cag cag cag ggc cgg ctg gac aaa ctg       240
Thr Thr Ala Tyr Phe Leu Tyr Gln Gln Gln Gly Arg Leu Asp Lys Leu
65                  70                  75                  80 aca gtc acc tcc cag aac ttg cag ctg gag aac ctg cgc atg aaa ctt       288
Thr Val Thr Ser Gln Asn Leu Gln Leu Glu Asn Leu Arg Met Lys Leu
                85                  90                  95 ccc aag cct ccc aag cct gtg agc aag atg cgc atg gcc acc ccg ctg       336
Pro Lys Pro Pro Lys Pro Val Ser Lys Met Arg Met Ala Thr Pro Leu
            100                 105                 110 ctg atg cag gcg ctg ccc atg gga gcc ctg ccc cag ggg act agt gga       384
Leu Met Gln Ala Leu Pro Met Gly Ala Leu Pro Gln Gly Thr Ser Gly
        115                 120                 125 tcc act aac gcc tgc agt atc aat gga aat gct cca gct gaa atc gat       432
Ser Thr Asn Ala Cys Ser Ile Asn Gly Asn Ala Pro Ala Glu Ile Asp
    130                 135                 140 ttg cga caa atg cga act gtc act ccc att cgt atg caa gga ggc tgt       480
Leu Arg Gln Met Arg Thr Val Thr Pro Ile Arg Met Gln Gly Gly Cys
145                 150                 155                 160 ggt tca tgt tgg gct ttc tct ggt gtt gcc gca act gaa tca gct tat       528
Gly Ser Cys Trp Ala Phe Ser Gly Val Ala Ala Thr Glu Ser Ala Tyr
                165                 170                 175 ttg gct cac cgt aat caa tca ttg gat ctt gct gaa caa gaa tta gtc       576
Leu Ala His Arg Asn Gln Ser Leu Asp Leu Ala Glu Gln Glu Leu Val
            180                 185                 190 gat tgt gct tcc caa cac ggt tgt cat ggt gat acc att cca cgt ggt       624
Asp Cys Ala Ser Gln His Gly Cys His Gly Asp Thr Ile Pro Arg Gly
        195                 200                 205 att gaa tac atc caa cat aat ggt gtc gtc caa gaa agc tac tat cga       672
Ile Glu Tyr Ile Gln His Asn Gly Val Val Gln Glu Ser Tyr Tyr Arg
    210                 215                 220 tac gtt gca cga gaa caa tca tgc cga cga cca aat gca caa cgt ttc       720
Tyr Val Ala Arg Glu Gln Ser Cys Arg Arg Pro Asn Ala Gln Arg Phe
225                 230                 235                 240 ggt atc tca aac tat tgc caa att tac cca cca aat gca aac aaa att       768
Gly Ile Ser Asn Tyr Cys Gln Ile Tyr Pro Pro Asn Ala Asn Lys Ile
                245                 250                 255 cgt gaa gct ttg gct caa cca cag cgc tat tgc cgt cat tat tgg acc       816
Arg Glu Ala Leu Ala Gln Pro Gln Arg Tyr Cys Arg His Tyr Trp Thr
            260                 265                 270 atc aaa gat tta gac gca ttc cgt cat tat gat ggc cga aca atc att       864
Ile Lys Asp Leu Asp Ala Phe Arg His Tyr Asp Gly Arg Thr Ile Ile
        275                 280                 285 caa cgc gat aat ggt tac caa cca aac tat cac gct gtc aac att gtt       912
Gln Arg Asp Asn Gly Tyr Gln Pro Asn Tyr His Ala Val Asn Ile Val
    290                 295                 300 ggt tac agt aac gca caa ggt gtc gat tat tgg atc gta cga aac agt       960
Gly Tyr Ser Asn Ala Gln Gly Val Asp Tyr Trp Ile Val Arg Asn Ser
305                 310                 315                 320
```

-continued

```
tgg gat acc aat tgg ggt gat aat ggt tac ggt tat ttt gct gcc aac   1008
Trp Asp Thr Asn Trp Gly Asp Asn Gly Tyr Gly Tyr Phe Ala Ala Asn
            325                 330                 335 atc gat ttg atg atg att gaa gaa tat cca tat gtt gtc att ctc taa   1056
Ile Asp Leu Met Met Ile Glu Glu Tyr Pro Tyr Val Val Ile Leu
340                 345                 350
```

<210> SEQ ID NO 28
<211> LENGTH: 351
<212> TYPE: PRT
<213> ORGANISM: tat-Ii-der p 1

<400> SEQUENCE: 28

Met Gly Tyr Gly Arg Lys Lys Arg Arg Gln Arg Arg Gly Ser Met
1               5                   10                  15

Asp Asp Gln His Asp Leu Ile Ser Asn Asn Glu Gln Leu Pro Met Leu
            20                  25                  30

Gly Arg Arg Pro Gly Ala Pro Glu Ser Lys Cys Ser Arg Gly Ala Leu
        35                  40                  45

Tyr Thr Gly Phe Ser Ile Leu Val Thr Leu Leu Ala Gly Gln Ala
50                  55                  60

Thr Thr Ala Tyr Phe Leu Tyr Gln Gln Gln Gly Arg Leu Asp Lys Leu
65                  70                  75                  80

Thr Val Thr Ser Gln Asn Leu Gln Leu Glu Asn Leu Arg Met Lys Leu
                85                  90                  95

Pro Lys Pro Pro Lys Pro Val Ser Lys Met Arg Met Ala Thr Pro Leu
            100                 105                 110

Leu Met Gln Ala Leu Pro Met Gly Ala Leu Pro Gln Gly Thr Ser Gly
        115                 120                 125

Ser Thr Asn Ala Cys Ser Ile Asn Gly Asn Ala Pro Ala Glu Ile Asp
130                 135                 140

Leu Arg Gln Met Arg Thr Val Thr Pro Ile Arg Met Gln Gly Gly Cys
145                 150                 155                 160

Gly Ser Cys Trp Ala Phe Ser Gly Val Ala Ala Thr Glu Ser Ala Tyr
                165                 170                 175

Leu Ala His Arg Asn Gln Ser Leu Asp Leu Ala Glu Gln Glu Leu Val
            180                 185                 190

Asp Cys Ala Ser Gln His Gly Cys His Gly Asp Thr Ile Pro Arg Gly
        195                 200                 205

Ile Glu Tyr Ile Gln His Asn Gly Val Val Gln Glu Ser Tyr Tyr Arg
210                 215                 220

Tyr Val Ala Arg Glu Gln Ser Cys Arg Arg Pro Asn Ala Gln Arg Phe
225                 230                 235                 240

Gly Ile Ser Asn Tyr Cys Gln Ile Tyr Pro Pro Asn Ala Asn Lys Ile
                245                 250                 255

Arg Glu Ala Leu Ala Gln Pro Arg Tyr Cys Arg His Tyr Trp Thr
            260                 265                 270

Ile Lys Asp Leu Asp Ala Phe Arg His Tyr Asp Gly Arg Thr Ile Ile
        275                 280                 285

Gln Arg Asp Asn Gly Tyr Gln Pro Asn Tyr His Ala Val Asn Ile Val
290                 295                 300

Gly Tyr Ser Asn Ala Gln Gly Val Asp Tyr Trp Ile Val Arg Asn Ser
305                 310                 315                 320

Trp Asp Thr Asn Trp Gly Asp Asn Gly Tyr Gly Tyr Phe Ala Ala Asn
                325                 330                 335

```
                Ile Asp Leu Met Met Ile Glu Glu Tyr Pro Tyr Val Val Ile Leu
                            340                 345                 350

<210> SEQ ID NO 29
<211> LENGTH: 885
<212> TYPE: DNA
<213> ORGANISM: his-tat-Ii-api g 1
<220> FEATURE:
<221> NAME/KEY: CDS
<222> LOCATION: (1)..(885)

<400> SEQUENCE: 29 atg aga gga tcg cat cac cat cac cat cac gga tct ggt tac ggt cgt      48
Met Arg Gly Ser His His His His His His Gly Ser Gly Tyr Gly Arg
1               5                   10                  15 aaa aag cgt cgc cag cgt cgc cgt gga tct atg gat gac cag cac gac      96
Lys Lys Arg Arg Gln Arg Arg Arg Gly Ser Met Asp Asp Gln His Asp
            20                  25                  30 ctt atc tcc aac aat gag caa ctg ccc atg ctg ggc cgg cgc cct ggg     144
Leu Ile Ser Asn Asn Glu Gln Leu Pro Met Leu Gly Arg Arg Pro Gly
        35                  40                  45 gcc ccg gag agc aag tgc agc cgc gga gcc ctg tac aca ggc ttt tcc     192
Ala Pro Glu Ser Lys Cys Ser Arg Gly Ala Leu Tyr Thr Gly Phe Ser
    50                  55                  60 atc ctg gtg act ctg ctc ctc gct ggc cag gcc acc acc gcc tac ttc     240
Ile Leu Val Thr Leu Leu Leu Ala Gly Gln Ala Thr Thr Ala Tyr Phe
65                  70                  75                  80 ctg tac cag cag cag ggc cgg ctg gac aaa ctg aca gtc acc tcc cag     288
Leu Tyr Gln Gln Gln Gly Arg Leu Asp Lys Leu Thr Val Thr Ser Gln
                85                  90                  95 aac ttg cag ctg gag aac ctg cgc atg aaa ctt ccc aag cct ccc aag     336
Asn Leu Gln Leu Glu Asn Leu Arg Met Lys Leu Pro Lys Pro Pro Lys
            100                 105                 110 cct gtg agc aag atg cgc atg gcc acc ccg ctg ctg atg cag gcg ctg     384
Pro Val Ser Lys Met Arg Met Ala Thr Pro Leu Leu Met Gln Ala Leu
        115                 120                 125 ccc atg gga gcc ctg ccc cag ggg act agt gga tcc atg gga gtg cag     432
Pro Met Gly Ala Leu Pro Gln Gly Thr Ser Gly Ser Met Gly Val Gln
    130                 135                 140 aca cat gtg ttg gag ctc acc tcc tca gtc tca gct gag aaa ata ttc     480
Thr His Val Leu Glu Leu Thr Ser Ser Val Ser Ala Glu Lys Ile Phe
145                 150                 155                 160 cag ggc ttt gtc att gat gtt gac aca gtc ctt ccc aag gct gcg cct     528
Gln Gly Phe Val Ile Asp Val Asp Thr Val Leu Pro Lys Ala Ala Pro
                165                 170                 175 gga gct tac aag agt gtc gaa atc aag gga gat ggt gga cct gga acc     576
Gly Ala Tyr Lys Ser Val Glu Ile Lys Gly Asp Gly Gly Pro Gly Thr
            180                 185                 190 ctc aaa att att act ctt ccc gat ggt ggc ccg att acc aca atg acc     624
Leu Lys Ile Ile Thr Leu Pro Asp Gly Gly Pro Ile Thr Thr Met Thr
        195                 200                 205 ctt aga att gat gga gtt aac aag gag gca ttg aca ttt gat tac agc     672
Leu Arg Ile Asp Gly Val Asn Lys Glu Ala Leu Thr Phe Asp Tyr Ser
    210                 215                 220 gtg atc gac gga gac atc ctc ttg gga ttt atc gaa tcc att gaa aac     720
Val Ile Asp Gly Asp Ile Leu Leu Gly Phe Ile Glu Ser Ile Glu Asn
225                 230                 235                 240 cat gtt gta cta gtg cca act gct gat gga gga agc att tgc aag acc     768
His Val Val Leu Val Pro Thr Ala Asp Gly Gly Ser Ile Cys Lys Thr
                245                 250                 255 act gcc atc ttt cac acc aaa ggt gat gct gtg gtt cca gaa gag aat     816
Thr Ala Ile Phe His Thr Lys Gly Asp Ala Val Val Pro Glu Glu Asn
```

-continued

```
Thr Ala Ile Phe His Thr Lys Gly Asp Ala Val Val Pro Glu Glu Asn
            260                 265                 270 atc aag tat gcc aat gag cag aac act gct ctt ttc aag gct ctc gag      864
Ile Lys Tyr Ala Asn Glu Gln Asn Thr Ala Leu Phe Lys Ala Leu Glu
        275                 280                 285 gcc tat ctc atc gct aat taa                                          885
Ala Tyr Leu Ile Ala Asn
        290
```

<210> SEQ ID NO 30
<211> LENGTH: 294
<212> TYPE: PRT
<213> ORGANISM: his-tat-Ii-api g 1

<400> SEQUENCE: 30

```
Met Arg Gly Ser His His His His His His Gly Ser Gly Tyr Gly Arg
1               5                   10                  15

Lys Lys Arg Arg Gln Arg Arg Gly Ser Met Asp Asp Gln His Asp
            20                  25                  30

Leu Ile Ser Asn Asn Glu Gln Leu Pro Met Leu Gly Arg Arg Pro Gly
        35                  40                  45

Ala Pro Glu Ser Lys Cys Ser Arg Gly Ala Leu Tyr Thr Gly Phe Ser
    50                  55                  60

Ile Leu Val Thr Leu Leu Leu Ala Gly Gln Ala Thr Thr Ala Tyr Phe
65                  70                  75                  80

Leu Tyr Gln Gln Gln Gly Arg Leu Asp Lys Leu Thr Val Thr Ser Gln
                85                  90                  95

Asn Leu Gln Leu Glu Asn Leu Arg Met Lys Leu Pro Lys Pro Pro Lys
            100                 105                 110

Pro Val Ser Lys Met Arg Met Ala Thr Pro Leu Leu Met Gln Ala Leu
        115                 120                 125

Pro Met Gly Ala Leu Pro Gln Gly Thr Ser Gly Ser Met Gly Val Gln
    130                 135                 140

Thr His Val Leu Glu Leu Thr Ser Ser Val Ser Ala Glu Lys Ile Phe
145                 150                 155                 160

Gln Gly Phe Val Ile Asp Val Asp Thr Val Leu Pro Lys Ala Ala Pro
                165                 170                 175

Gly Ala Tyr Lys Ser Val Glu Ile Lys Gly Asp Gly Pro Gly Thr
            180                 185                 190

Leu Lys Ile Ile Thr Leu Pro Asp Gly Gly Pro Ile Thr Thr Met Thr
        195                 200                 205

Leu Arg Ile Asp Gly Val Asn Lys Glu Ala Leu Thr Phe Asp Tyr Ser
    210                 215                 220

Val Ile Asp Gly Asp Ile Leu Leu Gly Phe Ile Glu Ser Ile Glu Asn
225                 230                 235                 240

His Val Leu Val Pro Thr Ala Asp Gly Gly Ser Ile Cys Lys Thr
                245                 250                 255

Thr Ala Ile Phe His Thr Lys Gly Asp Ala Val Val Pro Glu Glu Asn
            260                 265                 270

Ile Lys Tyr Ala Asn Glu Gln Asn Thr Ala Leu Phe Lys Ala Leu Glu
        275                 280                 285

Ala Tyr Leu Ile Ala Asn
        290
```

<210> SEQ ID NO 31
<211> LENGTH: 852

```
<212> TYPE: DNA
<213> ORGANISM: tat-Ii-api g 1
<220> FEATURE:
<221> NAME/KEY: CDS
<222> LOCATION: (1)..(852)

<400> SEQUENCE: 31 atg ggt tac ggt cgt aaa aag cgt cgc cag cgt cgc cgt gga tct atg      48
Met Gly Tyr Gly Arg Lys Lys Arg Arg Gln Arg Arg Arg Gly Ser Met
1               5                   10                  15 gat gac cag cac gac ctt atc tcc aac aat gag caa ctg ccc atg ctg      96
Asp Asp Gln His Asp Leu Ile Ser Asn Asn Glu Gln Leu Pro Met Leu
                20                  25                  30 ggc cgg cgc cct ggg gcc ccg gag agc aag tgc agc cgc gga gcc ctg     144
Gly Arg Arg Pro Gly Ala Pro Glu Ser Lys Cys Ser Arg Gly Ala Leu
            35                  40                  45 tac aca ggc ttt tcc atc ctg gtg act ctg ctc ctc gct ggc cag gcc     192
Tyr Thr Gly Phe Ser Ile Leu Val Thr Leu Leu Leu Ala Gly Gln Ala
        50                  55                  60 acc acc gcc tac ttc ctg tac cag cag cag ggc cgg ctg gac aaa ctg     240
Thr Thr Ala Tyr Phe Leu Tyr Gln Gln Gln Gly Arg Leu Asp Lys Leu
65                  70                  75                  80 aca gtc acc tcc cag aac ttg cag ctg gag aac ctg cgc atg aaa ctt     288
Thr Val Thr Ser Gln Asn Leu Gln Leu Glu Asn Leu Arg Met Lys Leu
                85                  90                  95 ccc aag cct ccc aag cct gtg agc aag atg cgc atg gcc acc ccg ctg     336
Pro Lys Pro Pro Lys Pro Val Ser Lys Met Arg Met Ala Thr Pro Leu
                100                 105                 110 ctg atg cag gcg ctg ccc atg gga gcc ctg ccc cag ggg act agt gga     384
Leu Met Gln Ala Leu Pro Met Gly Ala Leu Pro Gln Gly Thr Ser Gly
            115                 120                 125 tcc atg gga gtg cag aca cat gtg ttg gag ctc acc tcc tca gtc tca     432
Ser Met Gly Val Gln Thr His Val Leu Glu Leu Thr Ser Ser Val Ser
        130                 135                 140 gct gag aaa ata ttc cag ggc ttt gtc att gat gtt gac aca gtc ctt     480
Ala Glu Lys Ile Phe Gln Gly Phe Val Ile Asp Val Asp Thr Val Leu
145                 150                 155                 160 ccc aag gct gcg cct gga gct tac aag agt gtc gaa atc aag gga gat     528
Pro Lys Ala Ala Pro Gly Ala Tyr Lys Ser Val Glu Ile Lys Gly Asp
                165                 170                 175 ggt gga cct gga acc ctc aaa att att act ctt ccc gat ggt ggc ccg     576
Gly Gly Pro Gly Thr Leu Lys Ile Ile Thr Leu Pro Asp Gly Gly Pro
                180                 185                 190 att acc aca atg acc ctt aga att gat gga gtt aac aag gag gca ttg     624
Ile Thr Thr Met Thr Leu Arg Ile Asp Gly Val Asn Lys Glu Ala Leu
            195                 200                 205 aca ttt gat tac agc gtg atc gac gga gac atc ctc ttg gga ttt atc     672
Thr Phe Asp Tyr Ser Val Ile Asp Gly Asp Ile Leu Leu Gly Phe Ile
        210                 215                 220 gaa tcc att gaa aac cat gtt gta cta gtg cca act gct gat gga gga     720
Glu Ser Ile Glu Asn His Val Val Leu Val Pro Thr Ala Asp Gly Gly
225                 230                 235                 240 agc att tgc aag acc act gcc atc ttt cac acc aaa ggt gat gct gtg     768
Ser Ile Cys Lys Thr Thr Ala Ile Phe His Thr Lys Gly Asp Ala Val
                245                 250                 255 gtt cca gaa gag aat atc aag tat gcc aat gag cag aac act gct ctt     816
Val Pro Glu Glu Asn Ile Lys Tyr Ala Asn Glu Gln Asn Thr Ala Leu
                260                 265                 270 ttc aag gct ctc gag gcc tat ctc atc gct aat taa                     852
Phe Lys Ala Leu Glu Ala Tyr Leu Ile Ala Asn
            275                 280
```

<210> SEQ ID NO 32
<211> LENGTH: 283
<212> TYPE: PRT
<213> ORGANISM: tat-Ii-api g 1

<400> SEQUENCE: 32

Met Gly Tyr Gly Arg Lys Lys Arg Arg Gln Arg Arg Gly Ser Met
1               5                   10                  15

Asp Asp Gln His Asp Leu Ile Ser Asn Asn Glu Gln Leu Pro Met Leu
            20                  25                  30

Gly Arg Arg Pro Gly Ala Pro Glu Ser Lys Cys Ser Arg Gly Ala Leu
        35                  40                  45

Tyr Thr Gly Phe Ser Ile Leu Val Thr Leu Leu Leu Ala Gly Gln Ala
    50                  55                  60

Thr Thr Ala Tyr Phe Leu Tyr Gln Gln Gln Gly Arg Leu Asp Lys Leu
65                  70                  75                  80

Thr Val Thr Ser Gln Asn Leu Gln Leu Glu Asn Leu Arg Met Lys Leu
                85                  90                  95

Pro Lys Pro Pro Lys Pro Val Ser Lys Met Arg Met Ala Thr Pro Leu
            100                 105                 110

Leu Met Gln Ala Leu Pro Met Gly Ala Leu Pro Gln Gly Thr Ser Gly
        115                 120                 125

Ser Met Gly Val Gln Thr His Val Leu Glu Leu Thr Ser Ser Val Ser
    130                 135                 140

Ala Glu Lys Ile Phe Gln Gly Phe Val Ile Asp Val Asp Thr Val Leu
145                 150                 155                 160

Pro Lys Ala Ala Pro Gly Ala Tyr Lys Ser Val Glu Ile Lys Gly Asp
                165                 170                 175

Gly Gly Pro Gly Thr Leu Lys Ile Ile Thr Leu Pro Asp Gly Gly Pro
            180                 185                 190

Ile Thr Thr Met Thr Leu Arg Ile Asp Gly Val Asn Lys Glu Ala Leu
        195                 200                 205

Thr Phe Asp Tyr Ser Val Ile Asp Gly Asp Ile Leu Leu Gly Phe Ile
    210                 215                 220

Glu Ser Ile Glu Asn His Val Val Leu Val Pro Thr Ala Asp Gly Gly
225                 230                 235                 240

Ser Ile Cys Lys Thr Thr Ala Ile Phe His Thr Lys Gly Asp Ala Val
                245                 250                 255

Val Pro Glu Glu Asn Ile Lys Tyr Ala Asn Glu Gln Asn Thr Ala Leu
            260                 265                 270

Phe Lys Ala Leu Glu Ala Tyr Leu Ile Ala Asn
        275                 280

<210> SEQ ID NO 33
<211> LENGTH: 825
<212> TYPE: DNA
<213> ORGANISM: his-tat-Ii-pla2
<220> FEATURE:
<221> NAME/KEY: CDS
<222> LOCATION: (1)..(825)

<400> SEQUENCE: 33 atg aga gga tcg cat cac cat cac cat cac gga tct ggt tac ggt cgt        48
Met Arg Gly Ser His His His His His His Gly Ser Gly Tyr Gly Arg
1               5                   10                  15 aaa aag cgt cgc cag cgt cgc cgt gga tct atg gat gac cag cac gac        96

|         |     |     |     |     |     |     |     |     |     |     |     |     |     |     |     |     |
|---------|-----|-----|-----|-----|-----|-----|-----|-----|-----|-----|-----|-----|-----|-----|-----|-----|

Lys Lys Arg Arg Gln Arg Arg Gly Ser Met Asp Asp Gln His Asp
         20                25                30

```
ctt atc tcc aac aat gag caa ctg ccc atg ctg ggc cgg cgc cct ggg      144
Leu Ile Ser Asn Asn Glu Gln Leu Pro Met Leu Gly Arg Arg Pro Gly
         35                  40                  45 gcc ccg gag agc aag tgc agc cgc gga gcc ctg tac aca ggc ttt tcc      192
Ala Pro Glu Ser Lys Cys Ser Arg Gly Ala Leu Tyr Thr Gly Phe Ser
 50                  55                  60 atc ctg gtg act ctg ctc ctc gct ggc cag gcc acc acc gcc tac ttc      240
Ile Leu Val Thr Leu Leu Leu Ala Gly Gln Ala Thr Thr Ala Tyr Phe
 65                  70                  75                  80 ctg tac cag cag cag ggc cgg ctg gac aaa ctg aca gtc acc tcc cag      288
Leu Tyr Gln Gln Gln Gly Arg Leu Asp Lys Leu Thr Val Thr Ser Gln
             85                  90                  95 aac ttg cag ctg gag aac ctg cgc atg aaa ctt ccc aag cct ccc aag      336
Asn Leu Gln Leu Glu Asn Leu Arg Met Lys Leu Pro Lys Pro Pro Lys
        100                 105                 110 cct gtg agc aag atg cgc atg gcc acc ccg ctg ctg atg cag gcg ctg      384
Pro Val Ser Lys Met Arg Met Ala Thr Pro Leu Leu Met Gln Ala Leu
            115                 120                 125 ccc atg gga gcc ctg ccc cag ggg act agt gga tcc ata ata tat cca      432
Pro Met Gly Ala Leu Pro Gln Gly Thr Ser Gly Ser Ile Ile Tyr Pro
130                 135                 140 gga acg tta tgg tgc ggg cat ggt aac aag tcg tcc ggc ccg aac gag      480
Gly Thr Leu Trp Cys Gly His Gly Asn Lys Ser Ser Gly Pro Asn Glu
145                 150                 155                 160 cta ggt cgg ttc aag cac acg gat gca tgc tgt cga acc cac gac atg      528
Leu Gly Arg Phe Lys His Thr Asp Ala Cys Cys Arg Thr His Asp Met
                165                 170                 175 tgc ccg gac gtg atg tca gct ggt gaa tcg aag cac ggc ctg acc aac      576
Cys Pro Asp Val Met Ser Ala Gly Glu Ser Lys His Gly Leu Thr Asn
            180                 185                 190 acg gcc tcc cac acc agg ttg tcg tgc gac tgc gac gac aag ttc tat      624
Thr Ala Ser His Thr Arg Leu Ser Cys Asp Cys Asp Asp Lys Phe Tyr
            195                 200                 205 gat tgt ctt aaa aat tcg gcg gac acg att agc tcg tat ttc gta ggg      672
Asp Cys Leu Lys Asn Ser Ala Asp Thr Ile Ser Ser Tyr Phe Val Gly
210                 215                 220 aag atg tac ttc aat ctg ata gac acg aag tgt tac aaa ctg gag cat      720
Lys Met Tyr Phe Asn Leu Ile Asp Thr Lys Cys Tyr Lys Leu Glu His
225                 230                 235                 240 cct gtc acc ggg tgc ggt gag aga acc gag ggt cgt tgt ctt cac tac      768
Pro Val Thr Gly Cys Gly Glu Arg Thr Glu Gly Arg Cys Leu His Tyr
                245                 250                 255 acc gtg gac aaa agc aaa ccg aaa gtg tac caa tgg ttc gat ctt cgc      816
Thr Val Asp Lys Ser Lys Pro Lys Val Tyr Gln Trp Phe Asp Leu Arg
            260                 265                 270 aag tat tga                                                          825
Lys Tyr
```

<210> SEQ ID NO 34
<211> LENGTH: 274
<212> TYPE: PRT
<213> ORGANISM: his-tat-Ii-pla2

<400> SEQUENCE: 34

Met Arg Gly Ser His His His His His His Gly Ser Gly Tyr Gly Arg
1               5                   10                  15

Lys Lys Arg Gln Arg Arg Gly Ser Met Asp Asp Gln His Asp
                20                  25                  30

Leu Ile Ser Asn Asn Glu Gln Leu Pro Met Leu Gly Arg Arg Pro Gly
            35                  40                  45

Ala Pro Glu Ser Lys Cys Ser Arg Gly Ala Leu Tyr Thr Gly Phe Ser
 50                  55                  60

Ile Leu Val Thr Leu Leu Ala Gly Gln Ala Thr Thr Ala Tyr Phe
65                  70                  75                  80

Leu Tyr Gln Gln Gln Gly Arg Leu Asp Lys Leu Thr Val Thr Ser Gln
                85                  90                  95

Asn Leu Gln Leu Glu Asn Leu Arg Met Lys Leu Pro Lys Pro Pro Lys
            100                 105                 110

Pro Val Ser Lys Met Arg Met Ala Thr Pro Leu Leu Met Gln Ala Leu
        115                 120                 125

Pro Met Gly Ala Leu Pro Gln Gly Thr Ser Gly Ser Ile Ile Tyr Pro
    130                 135                 140

Gly Thr Leu Trp Cys Gly His Gly Asn Lys Ser Ser Gly Pro Asn Glu
145                 150                 155                 160

Leu Gly Arg Phe Lys His Thr Asp Ala Cys Cys Arg Thr His Asp Met
                165                 170                 175

Cys Pro Asp Val Met Ser Ala Gly Glu Ser Lys His Gly Leu Thr Asn
            180                 185                 190

Thr Ala Ser His Thr Arg Leu Ser Cys Asp Cys Asp Lys Phe Tyr
        195                 200                 205

Asp Cys Leu Lys Asn Ser Ala Asp Thr Ile Ser Ser Tyr Phe Val Gly
    210                 215                 220

Lys Met Tyr Phe Asn Leu Ile Asp Thr Lys Cys Tyr Lys Leu Glu His
225                 230                 235                 240

Pro Val Thr Gly Cys Gly Glu Arg Thr Glu Gly Arg Cys Leu His Tyr
                245                 250                 255

Thr Val Asp Lys Ser Lys Pro Lys Val Tyr Gln Trp Phe Asp Leu Arg
            260                 265                 270

Lys Tyr

<210> SEQ ID NO 35
<211> LENGTH: 792
<212> TYPE: DNA
<213> ORGANISM: tat-Ii-pla2
<220> FEATURE:
<221> NAME/KEY: CDS
<222> LOCATION: (1)..(792)

<400> SEQUENCE: 35

```
atg ggt tac ggt cgt aaa aag cgt cgc cag cgt cgc cgt gga tct atg     48
Met Gly Tyr Gly Arg Lys Lys Arg Arg Gln Arg Arg Arg Gly Ser Met
1               5                   10                  15 gat gac cag cac gac ctt atc tcc aac aat gag caa ctg ccc atg ctg     96
Asp Asp Gln His Asp Leu Ile Ser Asn Asn Glu Gln Leu Pro Met Leu
            20                  25                  30 ggc cgg cgc cct ggg gcc ccg gag agc aag tgc agc cgc gga gcc ctg    144
Gly Arg Arg Pro Gly Ala Pro Glu Ser Lys Cys Ser Arg Gly Ala Leu
        35                  40                  45 tac aca ggc ttt tcc atc ctg gtg act ctg ctc ctc gct ggc cag gcc    192
Tyr Thr Gly Phe Ser Ile Leu Val Thr Leu Leu Leu Ala Gly Gln Ala
    50                  55                  60 acc acc gcc tac ttc ctg tac cag cag cag ggc cgg ctg gac aaa ctg    240
Thr Thr Ala Tyr Phe Leu Tyr Gln Gln Gln Gly Arg Leu Asp Lys Leu
65                  70                  75                  80
```

-continued

```
aca gtc acc tcc cag aac ttg cag ctg gag aac ctg cgc atg aaa ctt      288
Thr Val Thr Ser Gln Asn Leu Gln Leu Glu Asn Leu Arg Met Lys Leu
             85                  90                  95 ccc aag cct ccc aag cct gtg agc aag atg cgc atg gcc acc ccg ctg      336
Pro Lys Pro Pro Lys Pro Val Ser Lys Met Arg Met Ala Thr Pro Leu
        100                 105                 110 ctg atg cag gcg ctg ccc atg gga gcc ctg ccc cag ggg act agt gga      384
Leu Met Gln Ala Leu Pro Met Gly Ala Leu Pro Gln Gly Thr Ser Gly
        115                 120                 125 tcc ata ata tat cca gga acg tta tgg tgc ggg cat ggt aac aag tcg      432
Ser Ile Ile Tyr Pro Gly Thr Leu Trp Cys Gly His Gly Asn Lys Ser
130                 135                 140 tcc ggc ccg aac gag cta ggt cgg ttc aag cac acg gat gca tgc tgt      480
Ser Gly Pro Asn Glu Leu Gly Arg Phe Lys His Thr Asp Ala Cys Cys
145                 150                 155                 160 cga acc cac gac atg tgc ccg gac gtg atg tca gct ggt gaa tcg aag      528
Arg Thr His Asp Met Cys Pro Asp Val Met Ser Ala Gly Glu Ser Lys
                165                 170                 175 cac ggc ctg acc aac acg gcc tcc cac acc agg ttg tcg tgc gac tgc      576
His Gly Leu Thr Asn Thr Ala Ser His Thr Arg Leu Ser Cys Asp Cys
            180                 185                 190 gac gac aag ttc tat gat tgt ctt aaa aat tcg gcg gac acg att agc      624
Asp Asp Lys Phe Tyr Asp Cys Leu Lys Asn Ser Ala Asp Thr Ile Ser
        195                 200                 205 tcg tat ttc gta ggg aag atg tac ttc aat ctg ata gac acg aag tgt      672
Ser Tyr Phe Val Gly Lys Met Tyr Phe Asn Leu Ile Asp Thr Lys Cys
        210                 215                 220 tac aaa ctg gag cat cct gtc acc ggg tgc ggt gag aga acc gag ggt      720
Tyr Lys Leu Glu His Pro Val Thr Gly Cys Gly Glu Arg Thr Glu Gly
225                 230                 235                 240 cgt tgt ctt cac tac acc gtg gac aaa agc aaa ccg aaa gtg tac caa      768
Arg Cys Leu His Tyr Thr Val Asp Lys Ser Lys Pro Lys Val Tyr Gln
                245                 250                 255 tgg ttc gat ctt cgc aag tat tga                                      792
Trp Phe Asp Leu Arg Lys Tyr
                260
```

<210> SEQ ID NO 36
<211> LENGTH: 263
<212> TYPE: PRT
<213> ORGANISM: tat-Ii-pla2

<400> SEQUENCE: 36

```
Met Gly Tyr Gly Arg Lys Lys Arg Arg Gln Arg Arg Gly Ser Met
1               5                  10                  15

Asp Asp Gln His Asp Leu Ile Ser Asn Asn Glu Gln Leu Pro Met Leu
            20                  25                  30

Gly Arg Arg Pro Gly Ala Pro Glu Ser Lys Cys Ser Arg Gly Ala Leu
        35                  40                  45

Tyr Thr Gly Phe Ser Ile Leu Val Thr Leu Leu Ala Gly Gln Ala
    50                  55                  60

Thr Thr Ala Tyr Phe Leu Tyr Gln Gln Gln Gly Arg Leu Asp Lys Leu
65                  70                  75                  80

Thr Val Thr Ser Gln Asn Leu Gln Leu Glu Asn Leu Arg Met Lys Leu
             85                  90                  95

Pro Lys Pro Pro Lys Pro Val Ser Lys Met Arg Met Ala Thr Pro Leu
        100                 105                 110

Leu Met Gln Ala Leu Pro Met Gly Ala Leu Pro Gln Gly Thr Ser Gly
        115                 120                 125
```

```
Ser Ile Ile Tyr Pro Gly Thr Leu Trp Cys Gly His Gly Asn Lys Ser
    130                 135                 140

Ser Gly Pro Asn Glu Leu Gly Arg Phe Lys His Thr Asp Ala Cys Cys
145                 150                 155                 160

Arg Thr His Asp Met Cys Pro Asp Val Met Ser Ala Gly Glu Ser Lys
                165                 170                 175

His Gly Leu Thr Asn Thr Ala Ser His Thr Arg Leu Ser Cys Asp Cys
            180                 185                 190

Asp Asp Lys Phe Tyr Asp Cys Leu Lys Asn Ser Ala Asp Thr Ile Ser
        195                 200                 205

Ser Tyr Phe Val Gly Lys Met Tyr Phe Asn Leu Ile Asp Thr Lys Cys
    210                 215                 220

Tyr Lys Leu Glu His Pro Val Thr Gly Cys Gly Glu Arg Thr Glu Gly
225                 230                 235                 240

Arg Cys Leu His Tyr Thr Val Asp Lys Ser Lys Pro Lys Val Tyr Gln
                245                 250                 255

Trp Phe Asp Leu Arg Lys Tyr
            260

<210> SEQ ID NO 37
<211> LENGTH: 16
<212> TYPE: PRT
<213> ORGANISM: Artificial
<220> FEATURE:
<223> OTHER INFORMATION: the W/R peptide

<400> SEQUENCE: 37

Arg Arg Trp Arg Arg Trp Trp Arg Arg Trp Trp Arg Arg Trp Arg Arg
1               5                   10                  15

<210> SEQ ID NO 38
<211> LENGTH: 11
<212> TYPE: PRT
<213> ORGANISM: Artificial
<220> FEATURE:
<223> OTHER INFORMATION: modified TAT peptide

<400> SEQUENCE: 38

Gly Arg Arg Arg Arg Arg Arg Arg Arg Arg Gln
1               5                   10

<210> SEQ ID NO 39
<211> LENGTH: 11
<212> TYPE: PRT
<213> ORGANISM: Human immunodeficiency virus

<400> SEQUENCE: 39

Tyr Gly Arg Lys Lys Arg Arg Gln Arg Arg Arg
1               5                   10

<210> SEQ ID NO 40
<211> LENGTH: 34
<212> TYPE: PRT
<213> ORGANISM: herpes simplex virus 7

<400> SEQUENCE: 40

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30
```

Val Glu

<210> SEQ ID NO 41
<211> LENGTH: 16
<212> TYPE: PRT
<213> ORGANISM: Drosophila melanogaster

<400> SEQUENCE: 41

Arg Gln Ile Lys Ile Trp Phe Gln Asn Arg Arg Met Lys Trp Lys Lys
1               5                   10                  15

<210> SEQ ID NO 42
<211> LENGTH: 4
<212> TYPE: PRT
<213> ORGANISM: Artificial
<220> FEATURE:
<223> OTHER INFORMATION: partial sequence form calreticulin

<400> SEQUENCE: 42

Lys Asp Glu Leu
1

<210> SEQ ID NO 43
<211> LENGTH: 4
<212> TYPE: PRT
<213> ORGANISM: Artificial
<220> FEATURE:
<223> OTHER INFORMATION: motif from beta-chain of HLA-DM

<400> SEQUENCE: 43

Tyr Thr Pro Leu
1

<210> SEQ ID NO 44
<211> LENGTH: 12
<212> TYPE: PRT
<213> ORGANISM: Human immunodeficiency virus

<400> SEQUENCE: 44

Gly Tyr Gly Arg Lys Lys Arg Arg Gln Arg Arg Arg
1               5                   10